(12) United States Patent
Pu et al.

(10) Patent No.: US 11,739,136 B2
(45) Date of Patent: Aug. 29, 2023

(54) INDUCIBLE DOMINANT NEGATIVE PD-1 AND USES IN ADOPTIVE CELL THERAPY

(71) Applicant: Innovative Cellular Therapeutics Holdings, Ltd., Grand Cayman (KY)

(72) Inventors: Chengfei Pu, Shanghai (CN); Zhiyuan Cao, Shanghai (CN); Lei Xiao, Shanghai (CN)

(73) Assignee: Innovative Cellular Therapeutics Holdings, Ltd., George Town (KY)

( * ) Notice: Subject to any disclaimer, the term of this patent is extended or adjusted under 35 U.S.C. 154(b) by 653 days.

(21) Appl. No.: 16/822,497

(22) Filed: Mar. 18, 2020

(65) Prior Publication Data
US 2020/0299354 A1 Sep. 24, 2020

Related U.S. Application Data

(60) Provisional application No. 62/819,970, filed on Mar. 18, 2019.

(51) Int. Cl.
| | | |
|---|---|---|
| *C07K 14/705* | (2006.01) |
| *C12N 5/0783* | (2010.01) |
| *C07K 14/725* | (2006.01) |
| *C07K 16/30* | (2006.01) |

(52) U.S. Cl.
CPC .... *C07K 14/70521* (2013.01); *C07K 14/7051* (2013.01); *C07K 16/30* (2013.01); *C12N 5/0636* (2013.01); *C07K 2319/03* (2013.01); *C12N 2510/00* (2013.01)

(58) Field of Classification Search
CPC .............. C12N 5/0636; C12N 2510/00; C12N 2501/51; C07K 2319/03; C07K 16/30; C07K 16/3092; C07K 2317/622; A61K 2039/5158; A61K 39/00111; A61K 2039/5156

See application file for complete search history.

(56) References Cited

U.S. PATENT DOCUMENTS

2016/0256488 A1 * 9/2016 Wu .................. C07K 14/70521

FOREIGN PATENT DOCUMENTS

| WO | WO-2010126766 A1 * | 11/2010 | ......... C07K 14/4702 |
| WO | WO-2017040945 A1 * | 3/2017 | ............. A61K 35/17 |
| WO | WO-2018165228 A1 * | 9/2018 | ......... A61K 39/0011 |

\* cited by examiner

*Primary Examiner* — Hong Sang
(74) *Attorney, Agent, or Firm* — Lee & Hayes, P.C.

(57) ABSTRACT

Embodiments relate to a modified cell comprising a chimeric antigen receptor (CAR) and a dominant negative form of PD-1, wherein the dominant negative form of PD-1 lacks a functional PD-1 intracellular domain for PD-1/PD-L1 signal transduction, and the CAR comprises an antigen binding domain, a transmembrane domain, a co-stimulatory domain, and a CD3 zeta domain. The dominant negative form of PD-1 is regulated by an inducible gene expression system.

11 Claims, 19 Drawing Sheets

Specification includes a Sequence Listing.

INDUCIBLE DOMINANT NEGATIVE PD-1 AND USES IN ADOPTIVE CELL THERAPY

CROSS REFERENCE TO RELATED PATENT APPLICATIONS

This application claims the benefit of U.S. Provisional Application 62/819,970, filed Mar. 18, 2019, which is hereby incorporated by reference in their entirety.

SEQUENCE LISTING INFORMATION

A computer readable textfile, entitled "Sequence_Listing_ST25.txt," created on or about Mar. 10, 2020 with a file size of about 139 KB, contains the sequence listing for this application and is hereby incorporated by reference in its entirety.

BACKGROUND

In immune therapy, effective T-cell response plays an important role against infection and cancer. It has been reported that checkpoint molecules such as PD-1/PD-L1 signaling may suppress T-cell response in immune therapy; therefore, blocking PD-1/PD-L1 may enhance T-cell response. However, it has been shown that the deletion or genetic absence of PD-1 or other such molecules in T-cells in vivo may negatively impact the long-lived memory compartment either by preventing reprogramming or persistence to effect long-term efficacy of T-cell based therapy. Thus, there is a need to modulate the deletion or genetic absence of PD-1 or other such molecules in T-cells.

SUMMARY

Embodiments relate to modified cell comprising a plurality of nucleic acid sequences encoding a binding molecule and a dominant negative form of an inhibitory immune checkpoint molecule or a receptor thereof, wherein expression of the dominant negative form of the inhibitory immune checkpoint molecule is regulated by an inducible gene expression system. Embodiments relate to a modified cell comprising a binding molecule, and a dominant negative form of an inhibitory immune checkpoint molecule, wherein expression of the dominant negative form of the inhibitory immune checkpoint molecule is regulated by an inducible gene expression system. Embodiments relate to a polynucleotide encoding the binding molecule and/or the dominant negative form of the inhibitory immune checkpoint molecule. Embodiments relate to a pharmaceutical composition comprising the population of the modified cell. Embodiments relate to a kit comprising an effective amount of vector-free nucleic acids encoding the binding molecule and/or the dominant negative form of the inhibitory immune checkpoint molecule to render a population of immune cells specific for a tumor antigen expressed on the surface of the cells of a subject. Embodiments relate to a method of eliciting or enhancing T cell response, treating a subject in need thereof or enhancing cancer treatment thereof, the method comprising administering an effective amount of the composition or the kit to the subject.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
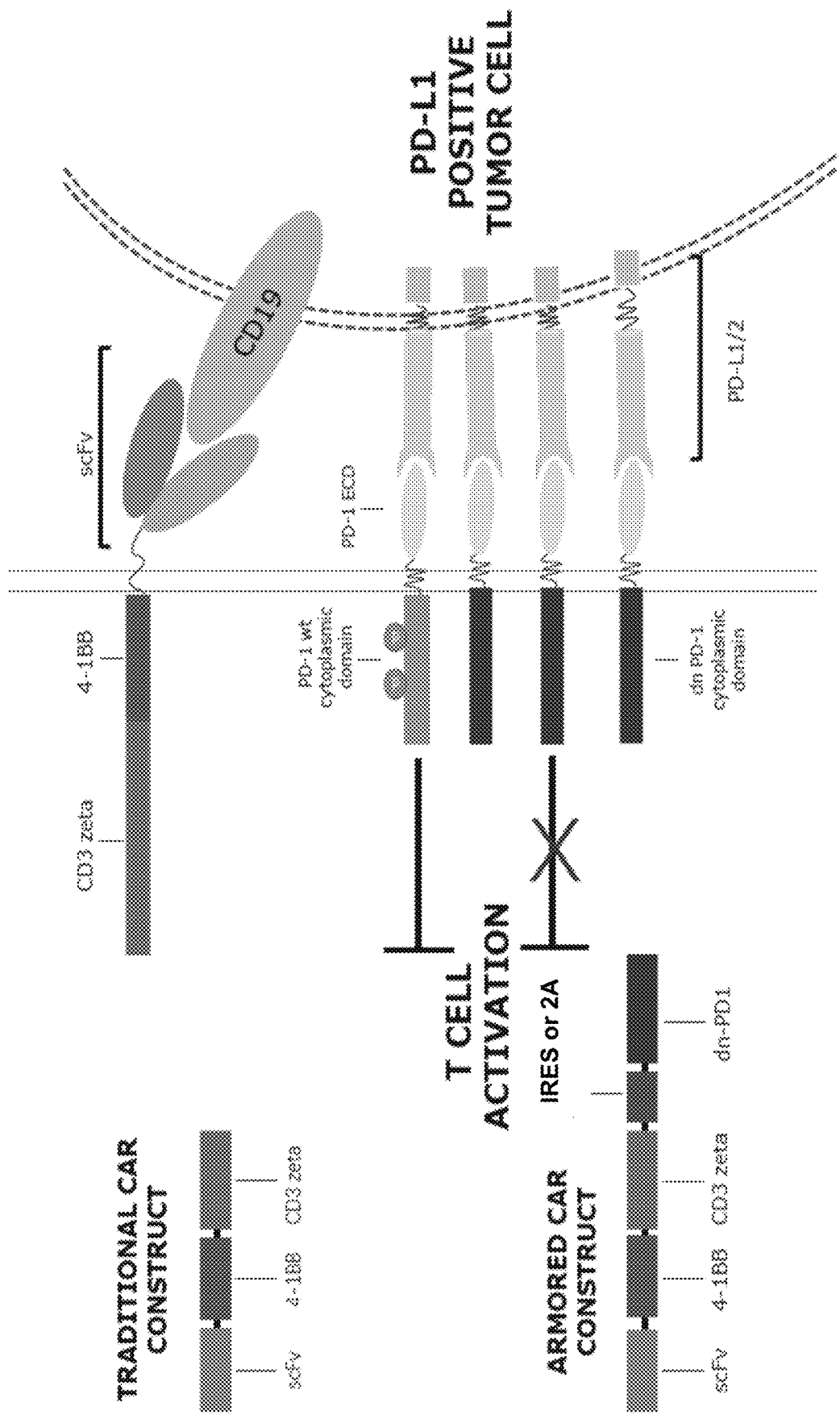
FIG. 1 is a schematic diagram showing an exemplary structure of hCD19CAR+dnPD-1 on surface of a T-cell.
Figure 2:
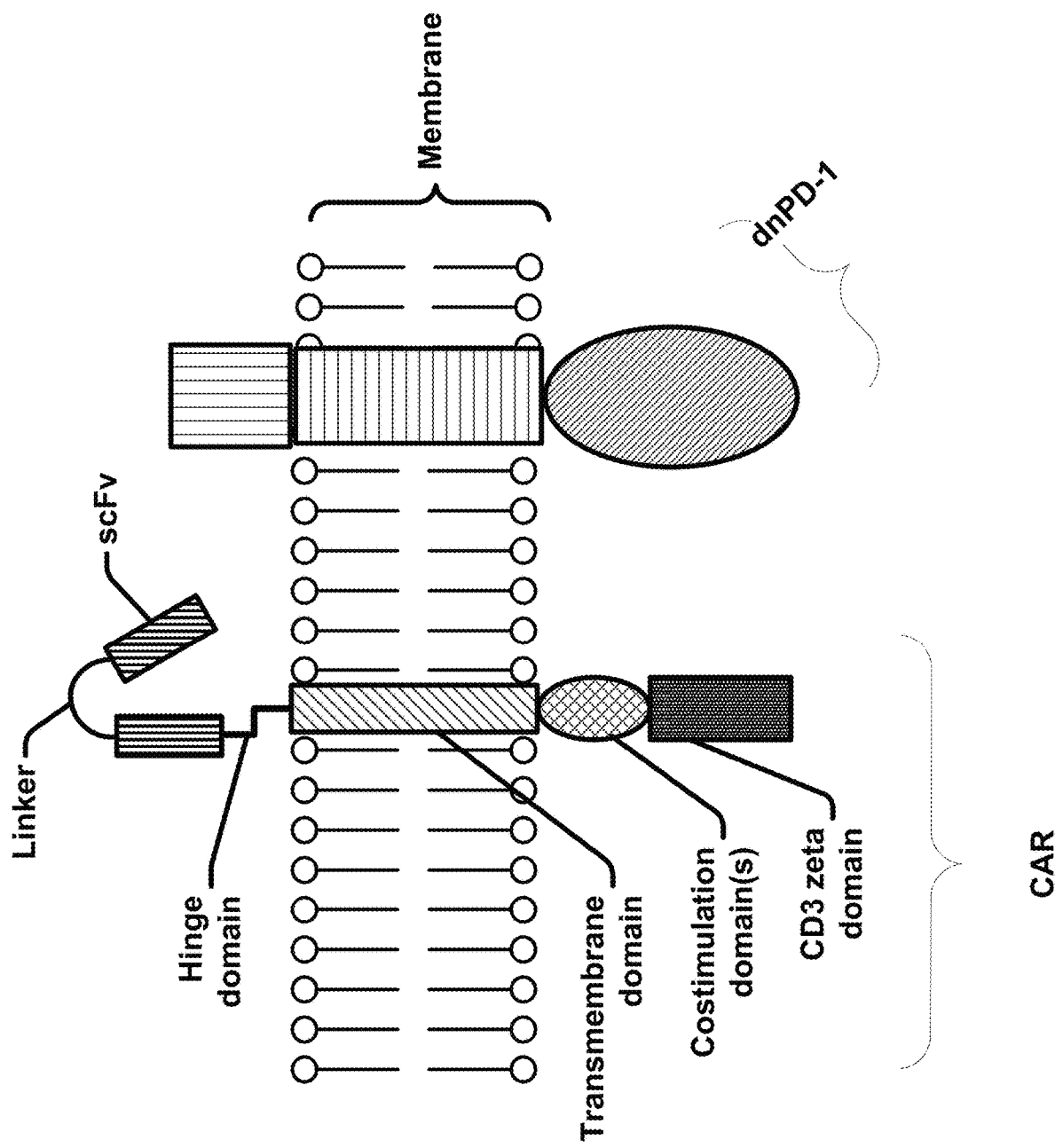
FIG. 2 is a schematic diagram showing an exemplary portion of a cell membrane comprising a CAR molecule and dnPD-1.
Figure 3:
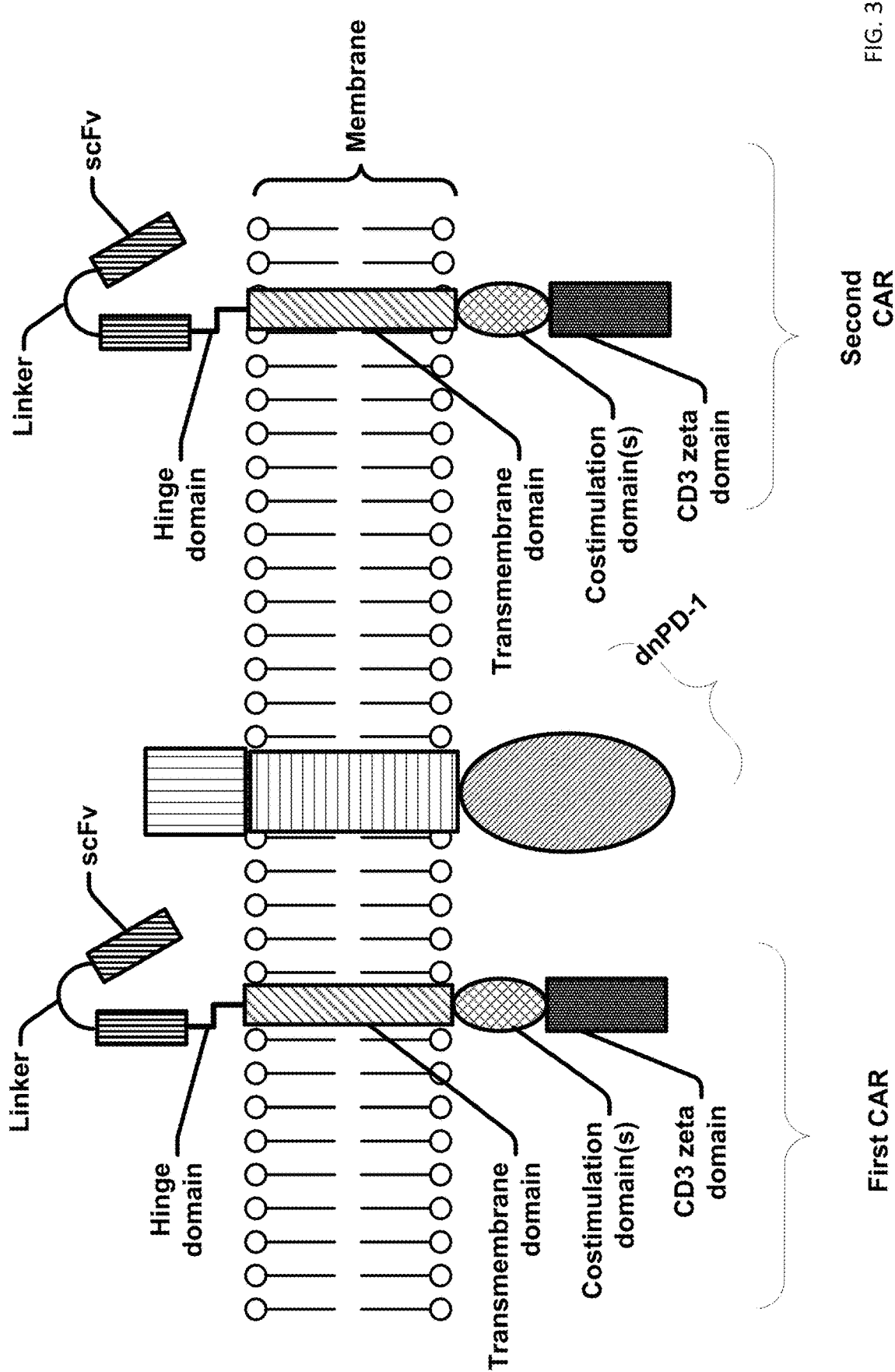
FIG. 3 is a schematic diagram showing an exemplary portion of a cell membrane comprising two CAR molecules and dnPD-1.
Figure 4:
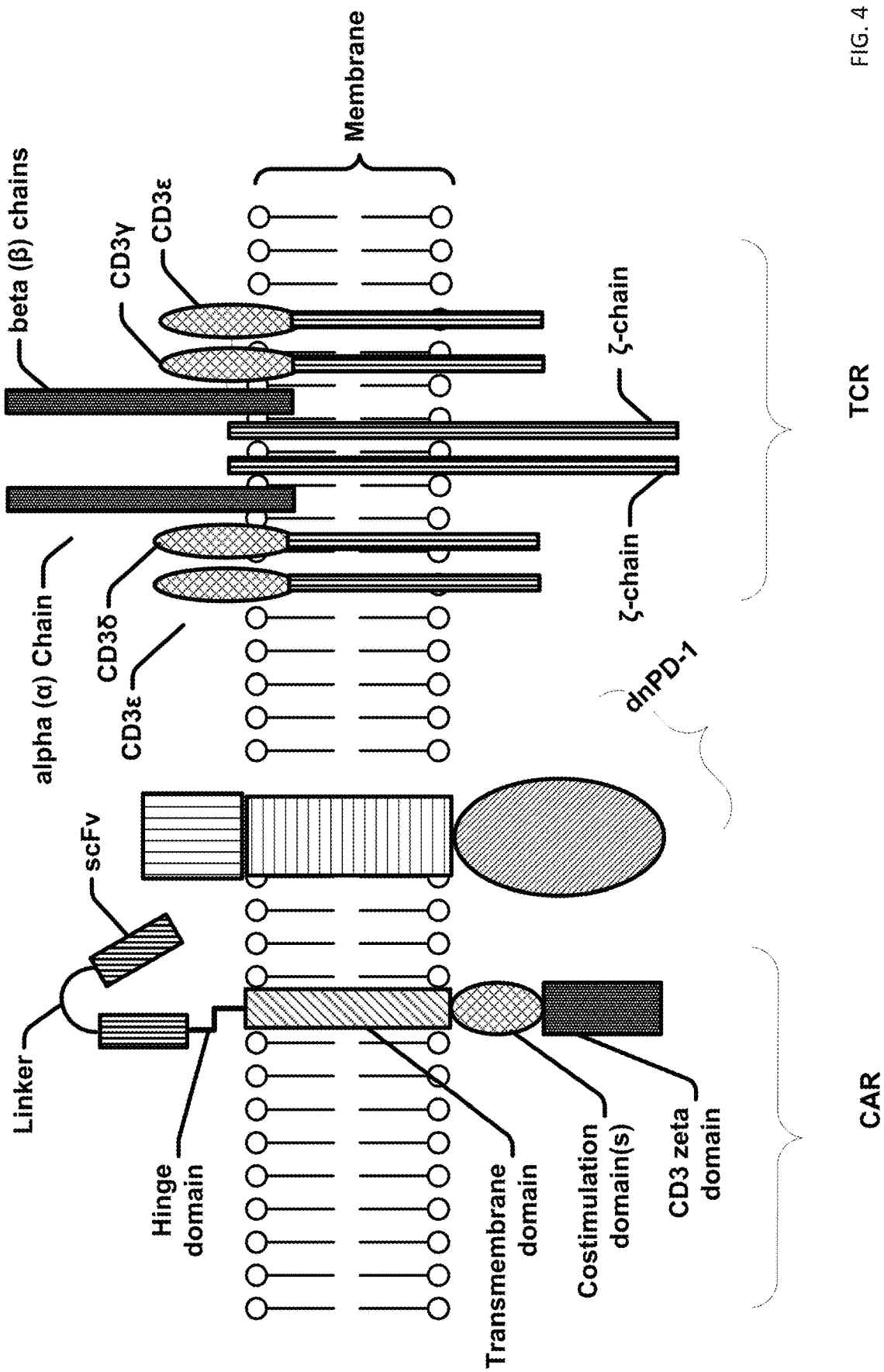
FIG. 4 is a schematic diagram showing an exemplary portion of a cell membrane comprising a CAR molecule, a T cell receptor (TCR), and dnPD-1.
Figure 5:
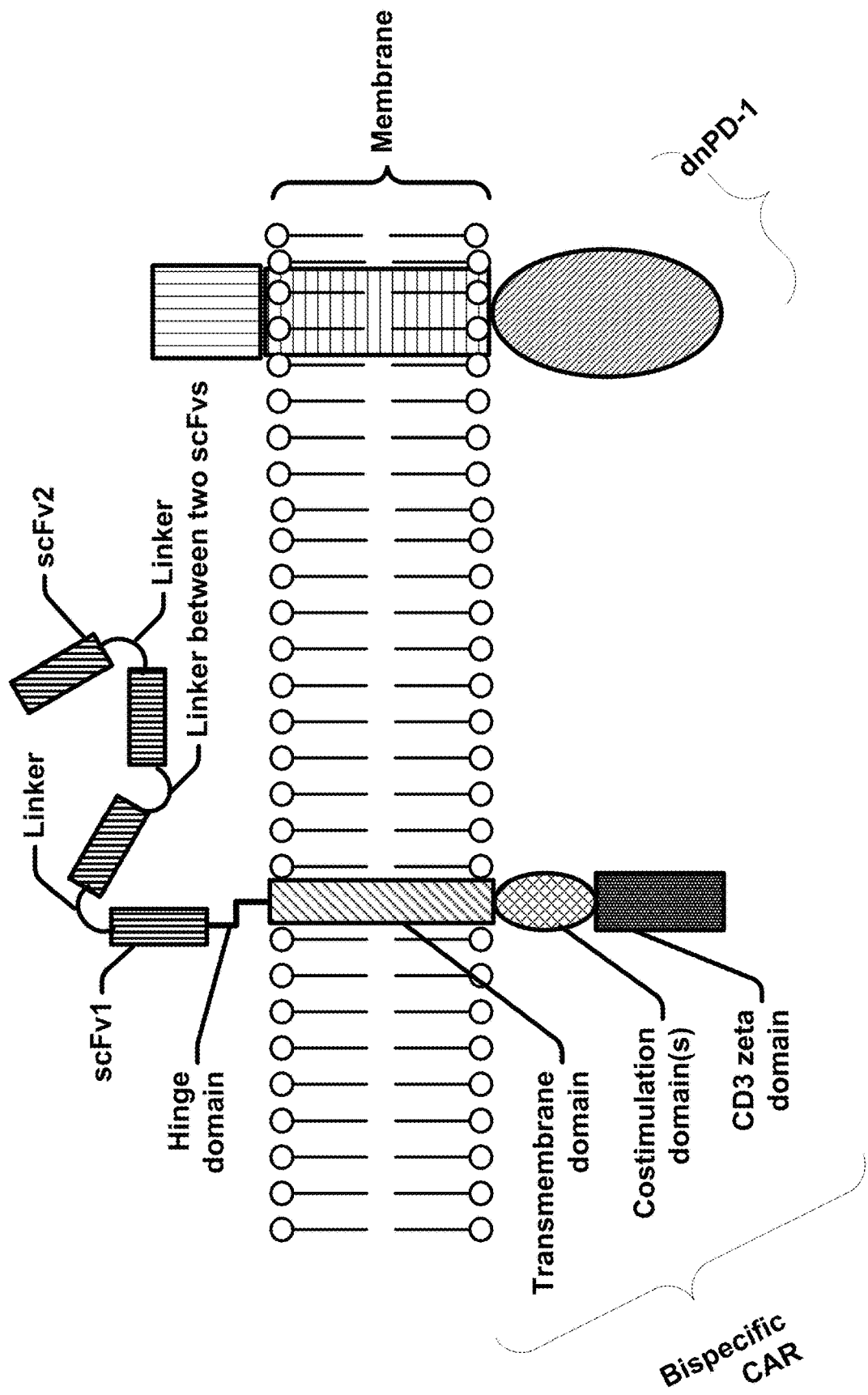
FIG. 5 is a schematic diagram showing an exemplary portion of a cell membrane comprising a bispecific CAR molecule and dnPD-1.
Figure 6:
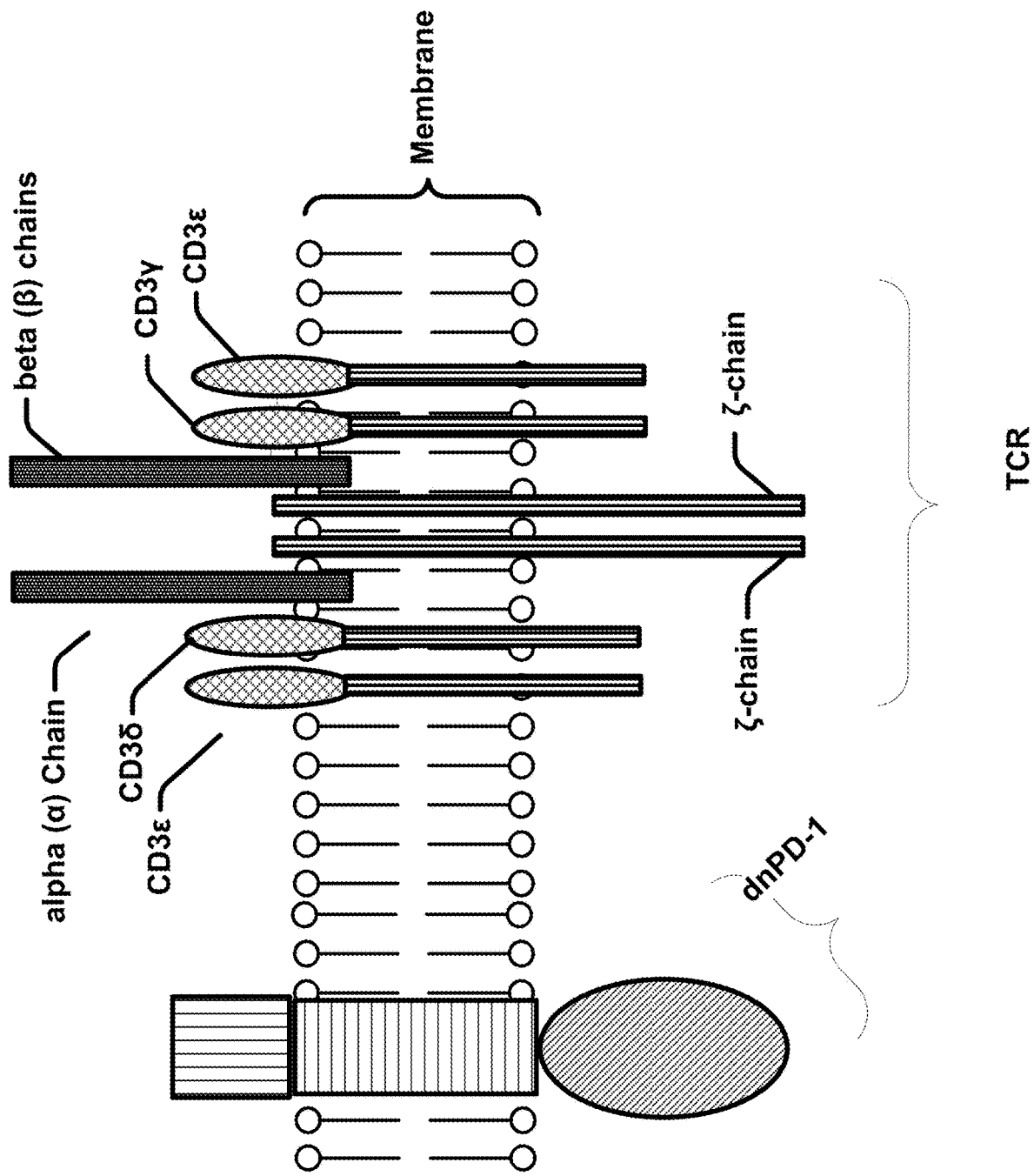
FIG. 6 is a schematic diagram showing an exemplary portion of a cell membrane comprising a TCR molecule and dnPD-1.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T-cells" refers to, among other things, T-cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated or recipient subject, but the donor subject has immune system markers which are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" as used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any elements listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T-cell, thereby providing a signal which, in addition to the primary signal provided by, for instance, binding of a TCR/CD3 complex with an MHC molecule loaded with peptide, mediates a T-cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T-cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T-cell that specifically binds with a co-stimulatory ligand, thereby mediating a co-stimulatory response by the T-cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T-cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially from components that normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In other embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein, and refer to any human, animal, or living organism, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals such as dogs, cats, mice, rats, and transgenic species thereof.

A subject in need of a treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a particular second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Further, a Zinc finger binding domain may be fused a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes), as illustrated in FIG. 1.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease. Exemplary target sites for various targeted ZFPs are shown in Table 1.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures. CD3 zeta is not the only suitable primary signaling domain for a CAR construct with respect to the primary response. For example, back in 1993, both CD3 zeta and FcR gamma were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T-cell receptors" PNAS, 1993 Jan. 15; 90(2):720-4, showed that two CAR constructs in which an scFv was fused to "either the FcR y chain or the CD3 complex s chain" triggered T-cell activation and target cell. Notably, as demonstrated in Eshhar et al., CAR constructs containing only the primary signaling domain CD3 zeta or FcR gamma are functional without the co-presence of costimulatory domains. Additional non-CD3 zeta based CAR constructs have been developed over the years. For example, Wang et al., "A Chimeric Antigen Receptor (CARs) Based Upon a Killer Immunoglobulin-Like Receptor (KIR) Triggers Robust Cytotoxic Activity in Solid Tumors" Molecular Therapy, vol. 22, no. Suppl. 1, May 2014, page S57, tested a CAR molecule in which an scFv was fused to "the transmembrane and cytoplasmic domain of" a killer immunoglobulin-like receptor (KIR). Wang et al. states that, "a KIR-based CAR targeting mesothelin (SS 1-KIR) triggers antigen-specific cytotoxic activity and cytokine production that is comparable to CD3~-based CARs." A second publication from the same group, Wang et al., "Generation of Potent T-cell Immunotherapy for Cancer Using DAP12-Based, Multichain, Chimeric Immunoreceptors" Cancer Immunol Res. 2015 July; 3(7):815-26, showed that a CAR molecule in which "a single-chain variable fragment for antigen recognition [was fused] to the transmembrane and cytoplasmic domains of KIR2DS2, a stimulatory killer immunoglobulin-like receptor (KIR)" functioned both in vitro and in vivo "when introduced into human T-cells with DAP12, an immunotyrosine-based activation motifs-containing adaptor."

The term "stimulatory molecule" refers to a molecule on a T-cell that specifically binds a cognate stimulatory ligand present on an antigen presenting cell. For example, a functional signaling domain derived from a stimulatory molecule is the zeta chain associated with the T-cell receptor complex.

The term "stimulatory ligand" refers to a ligand that when present on an antigen presenting cell (e.g., an APC, a dendritic cell, a B-cell, and the like) can specifically bind with a cognate binding partner (referred to herein as a "stimulatory molecule") on a cell, for example a T-cell, thereby mediating a primary response by the T-cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate transfer of nucleic acid into cells, such as, for example, polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV.

Lentiviral vectors have been generated by multiply attenuating the HIV virulence genes, for example, the genes env, vif, vpr, vpu, and nef are deleted making the vector biologically safe. Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Embodiments relate to a method for increasing a number or ratio of an immune cell subpopulation and/or increasing or extending persistence of the immune cell subpopulation in a subject having cancer, the method comprising: administering an effective amount of a composition comprising T-cells to the subject, the T-cells including an antigen binding molecule (e.g., a chimeric antigen receptor (CAR)) and a modified PD-1, the modified PD-1 lacking a functional PD-1 intracellular domain; and monitoring the T-cell response in the subject, the immune cell subpopulation comprising naive T-cells, stem cell memory T-cells, and/or central memory T-cells, the number or ration of the immune cell subpopulation in the subject increased as compared to corresponding T-cells that do not include the modified PD-1 or the persistence of the immune cell subpopulation in the subject increased or extended as compared to the corresponding T-cells that do not include the modified PD-1.

In embodiments, the immune cell subpopulation may have improved expansion and viability; and/or improved capability in tumor clearance and persistence. In embodiments, the immune cell subpopulation may have increased gene expression in at least one of CD27, CCR7, and CD62L; decreased gene expression in at least one of PD-1 and Tim-3; increased central memory T-cell subpopulation; and/or decreased effector T-cell subpopulation as comparison to T-cells that do not include the modified PD-1.

In embodiments, the monitoring the T-cell response in the subject comprises at least one of: detecting mRNA of the modified PD-1; detecting a number of one or more white blood cells; detecting a number of at least one of naive T-cells, stem cell memory T-cells, and central memory T-cells; detecting a CAR copy number; detecting CD3 positive cell number; detecting a number of T-cells expressing CAR; and detecting a level of one or more cytokines. In embodiments, the monitoring the T-cell response in the subject comprises monitoring the T-cell response in peripheral blood, bone marrow, lymph node tissue, cord blood, thymus tissue, tissue from a site of infection, ascites, pleural effusion, spleen tissue, or tumors of the subject. For example, the monitoring the T-cell response in the subject comprises monitoring the T-cell response in peripheral blood of the subject.

As used herein, the terms "T lymphocyte" and "T-cell" are used interchangeably and refer to a principal type of white blood cell that completes maturation in the thymus and that has various roles in the immune system, including the identification of specific foreign antigens in the body and the activation and deactivation of other immune cells A T-cell can be any T-cell, such as a cultured T-cell, e.g., a primary T-cell, or a T-cell from a cultured T-cell line, e.g., Jurkat, SupT 1, etc., or a T-cell obtained from a mammal. The T-cell can be CD3+ cells. The T-cell can be any type of T-cell and can be of any developmental stage, including but not limited to, CD4+/CD8+ double positive T-cells, CD4+ helper T-cells (e.g., Th1 and Th2 cells), CD8+ T-cells (e.g., cytotoxic T-cells), a T-cell present among peripheral blood mononuclear cells (PBMCs), peripheral blood leukocytes (PBLs), a T-cell that is among tumor infiltrating lymphocytes (TILs), memory T-cells, naive T-cells, regulatory T-cells, gamma delta T-cells (76 T-cells). Additional types of helper T-cells include cells such as Th3, Th17, Th9, or Tfh cells. Additional types of memory T-cells include cells such as central memory T-cells (Tcm cells), effector memory T-cells (Tem cells and TEIVIRA cells). The T-cell can also refer to a genetically engineered T-cell, such as a T-cell modified to express a T-cell receptor (TCR) or a chimeric antigen receptor (CAR). The T-cell can also be differentiated from a stem cell or progenitor cell.

As used herein, the term "naive T-cell" or Tn, refers to mature T-cells that, unlike activated or memory T-cells, have not encountered their cognate antigen within the periphery. Naive T-cells are commonly characterized by the surface expression of Lselectin (CD62L); the absence of the activation markers CD25, CD44 or CD69; and the absence of the memory CD45RO isoform They also express functional IL-7 receptors, consisting of subunits IL-7 receptor-u, CD127, and common-7 chain, CD132. In the naive state, T-cells are thought to be quiescent and non-dividing, requiring the common gamma chain cytokines IL-7 and IL-15 for homeostatic survival mechanisms.

As used herein, the term "central memory T-cells" or Tcm, refers to a subgroup or subpopulation of T-cells that express CD45RO and CD25 but do not express CD45RA Tcm also express genes associated with trafficking to secondary lymphoid organs, including CD62L, CXCR3, CCR7, unlike effector memory T-cells, or Tem that lose expression of these gene products.

As used herein, the term "stem memory T-cells," or "stem cell memory T-cells", or Tscm, refers to a subgroup or subpopulation of T-cells that are capable of self-renewing and generating Tcm, Tem and Teff (effector T-cells) Tscm have an expression pattern similar to Tn but unlike Tn, also express CD95.

As used herein, the term "population" when used with reference to T-cells raters to a group of cells including two or more T-cells, respectively. Using T-cell as an example, the isolated, or enriched, population of T-cells may include only one type of T-cell or may include a mixture of two or more types of T-cell. The isolated population of T-cells can be a homogeneous population of one type of T-cell or a heterogeneous population of two or more types of T-cell. The isolated population of T-cells can also be a heterogeneous population having T-cells and at least a cell other than a T-cell, e.g., a B cell, a macrophage, a neutrophil, an erythrocyte, a hepatocyte, an endothelial cell, an epithelial cell, a muscle cell, a brain cell, etc. The heterogeneous population can have from 0.01% to about 100% T-cell. Accordingly, an isolated population of T-cells can have at least 50%, 60% 70%, 80%, 90%, 95%, 98%, 99% T-cells. The isolated population of T-cells can include one or more, or all of, the different types of T-cells, including but not limited to those disclosed herein. In an isolated population of T-cells that includes more than one type of T-cells, the relative ratio of each type of T-cell can range from 0.01% to 99.99% The isolated population also can be a clonal population of T-cells, in which all the T-cells of the population are clones of a single T-cell.

An isolated population of T-cells may be obtained from a natural source, such as human peripheral blood or cord blood. Various ways of dissociating cells from tissues or cell mixtures to separate the various cell types have been developed in the art. In some cases, these manipulations result in a relatively homogeneous population of cells. The T-cells can be isolated by a sorting or selection process as described herein or by other methods known in the art. The proportion of T-cells in the isolated population may be higher than the proportion of T-cells in the natural source by at least about 10%, about 20%, about 305%, about 405%, about 505%, about 605%, about 705%, about 805%, about 85%, about 905%, or about 955%. The isolated population of T-cells can be for T-cells in general, or one or more specific types of T-cells. As used herein, the term "subpopulation" when used in reference to T-cells refers to a population of T-cells that includes less than all types of T-cells, respectively, that are found in nature.

In embodiments, the method may comprise monitoring phenotypes and other parameters (e.g., FIGS. 13 and 15-18) of CAR T-cells after the administration of the T-cells. In embodiments, the T-cells has more memory T-cells in the subject than those of T-cells that are introduced with the CAR and do not include the modified PD-1. In embodiments, the modified PD-1 comprise one sequences of SEQ ID: 36-40 or the modified PD-1 do not include SEQ ID: 41 and 42. In embodiments, the T-cells comprise a dominant negative variant of PD-1.

In embodiments, the CAR comprises an extracellular domain, a transmembrane domain, and an intracellular domain, the extracellular domain binds an antigen. In embodiments, the extracellular domain comprises one or more of SEQ ID: 5-17 or 30-35. In embodiments, the T-cells comprise one of SEQ ID: 18-29. In embodiments, the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

In embodiments, the T-cells comprise a CAR binding to a solid tumor antigen and a CAR binding a white cell antigen. In embodiments, the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, or EGFR, and the B cell antigen is CD19, CD20, CD22, or BCMA. In embodiments, the white cell antigen is a B cell antigen. In embodiments, the B cell antigen is CD19, CD20, CD22, or BCMA.

Embodiments relate to a pharmaceutical composition comprising human T-cells, wherein the human T-cells comprising: a first nucleic acid sequence that encodes truncated CTLA4 that reduces an inhibitory effect of CTLA4 ligand 1 on the human T-cells, the truncated CTLA4 lacking a functional CTLA4 intracellular domain; and a second nucleic acid sequence that encodes a chimeric antigen receptor (CAR) comprising an extracellular domain that recognizes a tumor antigen of the target cell, a transmembrane domain, and an intracellular domain comprising a CD3-zeta signaling domain and a signaling domain of a costimulatory molecule, and wherein the truncated CTLA4 and the CAR are expressed as gene products that are separate polypeptides. Embodiments relate to population of CAR cells comprising the first and second nucleic acid sequences. Embodiments relate a pharmaceutical composition comprising the population of the CAR cells. Embodiments relate a method of cause T-cell response in a subject in need thereof and/or treating a tumor of the subject, the method comprising administering an effective amount of the composition to the subject.

In embodiments, the truncated CTLA4 interferes with a pathway between CTLA4 of a human T-cell of the human cells and CTLA4 ligand of a target cell. In embodiments, the truncated CTLA4 comprises a CTLA4 extracellular domain or a CTLA4 transmembrane domain, or a combination thereof. In embodiments, the truncated CTLA4 comprises the amino acid sequences of SEQ ID: 43-51.

Embodiments relate to a method for increasing a number or ratio of an immune cell subpopulation and/or increasing or extending persistence of the immune cell subpopulation, the method comprising: introducing T-cells with a nucleic acid sequence encoding a chimeric antigen receptor (CAR); and introducing with the T-cells a nucleic acid sequence encoding a modified PD-1, the modified PD-1 lacking a functional PD-1 intracellular domain, the immune cell subpopulation comprising naive T-cells, stem cell memory T-cells, and/or central memory T-cells, the number or ration of the immune cell subpopulation increased as compared to corresponding T-cells that do not include the modified PD-1 or the persistence of the immune cell subpopulation increased or extended as compared to the corresponding T-cells that do not include the modified PD-1.

In embodiments, the antigen binding molecule is a chimeric antigen receptor (CAR) or a T-cell Receptor (TCR). The term "Chimeric Antigen Receptor" or alternatively a "CAR" refers to a recombinant polypeptide construct comprising at least an extracellular antigen binding domain, a transmembrane domain and an intracellular signaling domain (e.g., cytoplasmic domain). In embodiments, the domains in the CAR polypeptide construct are in the same polypeptide chain (e.g., comprising a chimeric fusion protein) or not contiguous with each other (e.g., in different polypeptide chains).

In embodiments, the intracellular signaling domain may include a functional signaling domain derived from a stimulatory molecule and/or a co-stimulatory molecule as described above. In embodiments, the intracellular signaling domain includes a functional signaling domain derived from a primary signaling domain (e.g., a primary signaling domain of CD3-zeta). In other embodiments, the intracellular signaling domain further includes one or more functional signaling domains derived from at least one co-stimulatory molecule. The co-stimulatory signaling region refers to a portion of the CAR including the intracellular domain of a co-stimulatory molecule. Co-stimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may include up to 300 amino acids, preferably 10 to 100 amino acids, and most preferably 25 to 50 amino acids.

The extracellular domain of a CAR may include an antigen binding domain (e.g., an scFv, a single domain antibody, or TCR (e.g., a TCR alpha binding domain or TCR beta binding domain)) that targets a specific tumor marker (e.g., a tumor antigen). Tumor antigens are proteins that are produced by tumor cells that elicit an immune response, particularly T-cell mediated immune responses. Tumor antigens are well known in the art and include, for example, a glioma-associated antigen, carcinoembryonic antigen (CEA), 3-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. For example, the tumor antigen is CD19, and the CAR thereof may be referred as CD19CAR.

In embodiments, the extracellular ligand-binding domain comprises an scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID NO: 75), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can, in turn, be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor.

In embodiments, the antigen binding molecule is a T-cell Receptor (TCR). In embodiments, the TCR is modified TCR. In embodiments, the TCR is derived from spontaneously occurring tumor-specific T-cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains. In embodiments, a T-cell clone that expresses a TCR with high affinity for the target antigen may be isolated. In embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T-cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ Chains are identified and isolated by molecular cloning. For example, for TCRα and TCRβ chains, the TCRα and TCRβ gene sequences are then used to generate an expression construct that ideally promotes stable, high-level expression of both TCR chains in human T-cells. The transduction vehicle (e.g., a gammaretrovirus or lentivirus) may be then generated and tested for functionality (antigen specificity and functional avidity) and used to produce a clinical lot of the vector. An aliquot of the final product is then used to transduce the target T-cell population (generally purified from patient PBMCs), which is expanded before infusion into the patient.

In embodiments, the binding element of the CAR may include any antigen binding moiety that when bound to its cognate antigen, affects a tumor cell such that the tumor cell fails to grow, or is promoted to die or diminish.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional information related to expression synthetic nucleic acids encoding CARs and gene transfer into mammalian cells is provided in U.S. Pat. No. 8,906,682, incorporated by reference in its entirety.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T-cells described herein may be administered at a dosage of $10^4$ to $10^9$ cells/kg body weight, preferably $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In embodiments, it may be desired to administer activated T-cells to a subject and then subsequently redraw the blood (or have apheresis performed), collect the activated and expanded T-cells, and reinfuse the patient with these activated and expanded T-cells. This process can be carried out multiple times every few weeks. In embodiments, T-cells can be activated from blood draws of from 10 cc to 400 cc. In embodiments, T-cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T-cells.

The administration of the pharmaceutical compositions described herein may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In embodiments, the T-cell compositions of the present disclosure are administered to a patient by intradermal or subcutaneous injection. In another embodiment, the T-cell compositions of the present disclosure are preferably administered by i.v. injection. The compositions of T-cells may be injected directly into a tumor, lymph node, or site of infection. In embodiments of the present disclosure, cells activated and expanded using the methods described herein, or other methods known in the art where T-cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T-cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In some embodiments, the cell compositions of the present disclosure are administered to a patient in conjunction with (e.g., before, simultaneously or following) bone marrow transplantation, T-cell ablative therapy using either chemotherapy agents such as, fludarabine, external-beam radiation therapy (XRT), cyclophosphamide, or antibodies such as OKT3 or CAMPATH. In other embodiments, the cell compositions of the present disclosure are administered following B-cell ablative therapy such as agents that react with CD20, e.g., Rituxan. For example, In embodiments, subjects may undergo standard treatment with high dose chemotherapy followed by peripheral blood stem cell transplantation. In embodiments, following the transplant, subjects receive an infusion of the expanded immune cells of the present disclosure. In other embodiments, expanded cells are administered before or following surgery.

The dosage of the above treatments to be administered to a patient will vary with the precise nature of the condition being treated and the recipient of the treatment. The scaling of dosages for human administration can be performed according to art-accepted practices by a physician depending on various factors.

Additional information on the methods of cancer treatment using engineered or modified T-cells is provided in U.S. Pat. No. 8,906,682, incorporated by reference in its entirety.

Embodiments relate to a modified cell comprising a binding molecule, and a dominant negative form of an inhibitory immune checkpoint molecule, wherein expression of the dominant negative form of the inhibitory immune checkpoint molecule is regulated by an inducible gene expression system. Embodiments relate to a polynucleotide encoding the binding molecule and/or the dominant negative form of the inhibitory immune checkpoint molecule. Embodiments relate to a pharmaceutical composition comprising the population of the modified cell. Embodiments relate to a kit comprising an effective amount of vector-free nucleic acids encoding the binding molecule and/or the dominant negative form of the inhibitory immune checkpoint molecule to render a population of immune cells specific for a tumor antigen expressed on the surface of the cells of a subject. Embodiments relate to a method of eliciting or enhancing T cell response, treating a subject in need thereof or enhancing cancer treatment thereof, the method comprising administering an effective amount of the composition or the kit to the subject.

Embodiments relate to a pharmaceutical composition comprising a population of the modified cells and a population of additional modified cells, wherein the modified cells bind a first antigen, and the additional modified cells bind a second antigen, which is different form the first antigen. In embodiments, the first antigen is a white blood cell antigen, and the second antigen is a solid tumor antigen. In embodiments, the second antigen is a white blood cell antigen, and the first antigen is a solid tumor antigen. In embodiments, the white blood cell antigen is CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the blood cell antigen is CD19, CD20, CD22, or BCMA. In embodiments, the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR. In embodiments, the solid tumor antigen comprises tumor associated MUC1, ACPP, TSHR, GUCY2C, UPK2, CLDN18.2, PSMA, DPEP3, CXCR5, B7-H3, MUC16, SIGLEC-15, CLDN6, Muc17, PRLR, and FZD10.

Embodiments relate to a method or use of polynucleotide, the method comprising providing a viral particle (e.g., AAV, lentivirus or their variants) comprising a vector genome, the vector genome comprising the polynucleotide encoding the binding molecule and/or the dominant negative form of the inhibitory immune checkpoint molecule, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity. In embodiments, the AAV preparation may include AAV vector particles, empty capsids and host cell impurities, thereby providing an AAV product substantially free of AAV empty capsids.

In embodiments, expression of the one or more molecules may be regulated by an inducible expression system. The inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis. In embodiments, the modified cells comprise a nucleic acid sequence encoding a reverse tetracycline transactivator (rtTA). In embodiments, expression of the one or more molecules is regulated by the rtTA, such that the one or more molecules are expressed in the presence of tetracycline. In embodiments, a concentration of tetracycline in the cell culture medium is not less than about 2 μg/ml. In embodiments, the tetracycline is selected from the group consisting of tetracycline, demeclocycline, meclocycline, doxycycline, lymecycline, methacycline, minocycline, oxytetracycline, rolitetracycline, and chlortetracycline. In embodiments, the tetracycline is doxycycline. In embodiments, the inducible suicide system is an HSV-TK system or an inducible caspase-9 system. In embodiments, the modified cells comprise a nucleic acid sequence encoding a suicide gene, such that when the modified cells are in the presence of a nucleoside analogue in a manner permitting expression of the suicide gene, to render the nucleoside analogue cytotoxic to the modified cells. In embodiments, the suicide gene is selected from the group consisting of thymidine kinase of herpes simplex virus, thymidine kinase of varicella zoster virus, and bacterial cytosine deaminase. In embodiments, the suicide gene is thymidine kinase of herpes simplex virus. In embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2, 5'-dideoxyuridine, idoxuridine, AZT, AIU, dideoxycytidine, and araC. In embodiments, the nucleoside analogue is ganciclovir.

In embodiments, expression of the one or more molecules is regulated by one or more promoters. In embodiments, the polynucleotide comprises a promoter comprising a binding site for a transcription modulator that modulates the expression and/or secretion of the one or more molecules in the cell. For example, the transcription modulator is or includes Hif1a, NFAT, FOXP3, and/or NFkB. For example, the one or more molecules comprise at least one cytokine associated with an oxygen-sensitive polypeptide domain, and the oxygen-sensitive polypeptide domain comprises HIF VHL binding domain.

In embodiments, the polynucleotide may integrate into the genome of the modified cell and descendants of the modified cell will also express the polynucleotide, resulting in a stably transfected modified cell. In embodiments, the modified cell may express the polynucleotide encoding the CAR but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

Embodiments relate to a method or use of polynucleotide. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation may include AAV vector particles, empty capsids and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) 22 May 2019, which are incorporated herein by reference.

In embodiments, the bioreactor may be inoculated at a cell density of approximately 0.5×106 cells/mL with viability greater than 95%. When the cell density reaches approximately 1.0×106 cells/mL, the cells may be transfected with the PEI/DNA complexes (polyplexes) with a PEI to DNA ratio of 2:1. At the time of harvest, AAV from the cell culture in the bioreactor may be released using the Triton X-100 method. All solutions may be added directly to the bioreactor, and the lysate was centrifuged at 4000×g for 20 min. The supernatant may be stored at −80° C. for further processing. AAV may be further purified. For example, AAV samples (12.3 mL) may be purified by overlaying them on top of series of step gradients using 15, 25, 40 and 54% iodixanol concentrations containing 1, 5, 7 and 5 mL, respectively. The 15% iodixanol concentration also contains 1 M NaCl to avoid aggregation of AAV with other cellular proteins and negatively charged nuclear components. After the completion of centrifugation, 5 mL may be withdrawn from 2 mm below the 40/54 interface marked before starting the ultracentrifugation at 385,000×g for 1 h 45 min in Sorvall T-865 rotor in Sorvall Ultracentrifuge. The viral vectors may be then quantified. For example, vectors AAV infectivity may be determined by the gene transfer assay (GTA) using GFP as a reporter gene in all cases. AAV infectivity assay where sample may be diluted before addition to the cells to have the GFP positive cells in the range of 2-20% to assure that only single virus has entered the cell for GFP expression. The GFP-positive cells may be quantified by FACS using HEK293 cells in suspension. The AAV may be then administrated to a subject. For example, AAV may be diluted in 0.9% sterile NaCl saline solution (supplemented with 0.25% human serum albumin [HSA]) for infusion in patients and the final volume of infusion will be calculated based on the patient's weight as 3 mL/kg.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, the term "expression" refers to expression or overexpression.

In embodiments, a T cell clone that expresses a TCR with a high affinity for the target antigen may be isolated. Tumor-infiltrating lymphocytes (TILs) or peripheral blood mononuclear cells (PBMCs) can be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle, for example, a gammaretrovirus or lentivirus, can then be generated and tested for functionality (antigen specificity and functional avidity) and used to produce a clinical lot of the vector. An aliquot of the final product can then be used to transduce the target T cell population (generally purified from patient PBMCs), which is expanded before infusion into the patient.

Various methods may be implemented to obtain genes encoding tumor-reactive TCR. More information is provided in Kershaw et al., Clin Transl Immunology. 2014 May; 3(5): e16. In embodiments, specific TCR can be derived from spontaneously occurring tumor-specific T cells in patients. Antigens included in this category include the melanocyte differentiation antigens MART-1 and gp100, as well as the MAGE antigens and NY-ESO-1, with expression in a broader range of cancers. TCRs specific for viral-associated malignancies can also be isolated, as long as viral proteins are expressed by transformed cells. Malignancies in this category include liver and cervical cancer, associated with hepatitis and papilloma viruses, and Epstein-Barr virus-associated malignancies. In embodiments, target antigens of the TCR may include CEA (e.g., for colorectal cancer), gp100, MART-1, p53 (e.g., for Melanoma), MAGE-A3 (e.g., Melanoma, esophageal and synovial sarcoma), NY-ESO-1 (e.g., for Melanoma and sarcoma as well as Multiple myelomas).

In embodiments, preparation and transfusion of tumor infiltrating lymphocytes (TIL) may be implemented by the following. For example, tumor tissue comes from surgical or biopsy specimens, may be obtained under aseptic conditions and transported to the cell culture chamber in ice box. Necrotic tissue and adipose tissue may be removed. The tumor tissue may be cut into small pieces of about 1-3 cubic millimeter. Collagenase, hyaluronidase and DNA enzyme may be added, and digested overnight at 4° C. Filtering with 0.2 um filter, cells may be separated and collected by lymphocyte separation fluid, 1500 rpm for 5 min. Expanding the cells with a culture medium comprising PHA, 2-mercaptoethanol and CD3 monoclonal antibody, a small dose of IL-2 (10-20 IU/ml) may be added to induce activation and proliferation. According to the growth situation, the cell density may be carefully detected and maintained within the range of 0.5-2*10^6/ml under the condition of 37° C. and 5% CO2 for 7-14 days. TIL positive cells have the ability to kill homologous cancer cell may be screened out by co-culture. The positive cells may be amplified in a serum-free medium containing a high dose of IL2 (5000-6000 IU/ml) until greater than 1*10 TILs may be obtained. To administer TILs, they may be first collected in saline using continuous-flow centrifugation and then filtered through a platelet-administration set into a volume of 200-300 mL containing 5% albumin and 450 000 IU of IL-2. The TILs may be infused into patients through a central venous catheter over a period of 30-60 minutes. In embodiments, TILs may be often infused in two to four separate bags; the infusions may be separated by several hours.

In embodiments, expression of the polynucleotide is regulated or modulated by a synthetic Notch receptor comprising, from N-terminal to C-terminal and in covalent linkage: a) an extracellular domain comprising an antibody (e.g., a single-chain Fv (scFv) or a nanobody) that specifically binds to an antigen; b) a Notch regulatory region (NRR) and c) an intracellular domain comprising a transcriptional activator comprising a DNA binding domain. In embodiments, the Notch regulatory region comprises a Lin 12-Notch repeat, a heterodimerization domain comprising an S2 proteolytic cleavage site and a transmembrane domain comprising an S3 proteolytic cleavage site. The intracellular domain is heterologous to the Notch regulatory region. In embodiments, the transcriptional activator replaces a naturally-occurring intracellular notch domain, and binding of the antibody to the antigen induces cleavage at the S2 and S3 proteolytic cleavage sites, thereby releasing the intracellular domain. The release of the intracellular domain causes the transcriptional activator to induce expression of the polynucleotide encoding one or more target proteins in the modified cell. In embodiments, the modified cell comprises a polynucleotide encoding the synthetic Notch receptor and a polynucleotide encoding a transcriptional control element that is responsive to the transcriptional activator and operably linked to the polynucleotide encoding one or more target proteins (e.g., CAR and scFv targeting M2).

"Suicide gene" is a nucleic acid coding for a product, wherein the product causes cell death by itself or in the presence of other compounds. A representative example of such a therapeutic nucleic acid (suicide gene) is one which codes for thymidine kinase of herpes simplex virus (HSV-TK). Additional examples are thymidine kinase of varicella zoster virus and the bacterial gene cytosine deaminase which can convert 5-fluorocytosine to the highly toxic compound 5-fluorouracil.

In embodiment, the modified cell of claim 1, wherein the inducible gene expression system comprises or is a lac system, a tetracycline system, or a galactose system. In embodiment, the expression of the dominant negative form of the inhibitory immune checkpoint molecule is regulated by Hif1a, NFAT, FOXP3, and/or NFkB.

In embodiment, the modified cell comprises a polynucleotide encoding the binding molecule and a dominant negative form of the inhibitory immune checkpoint molecule or a receptor thereof, wherein expression of the dominant negative form of the inhibitory immune checkpoint molecule is regulated by an inducible gene expression system.

In embodiment, the modified cell comprises a polynucleotide encoding the dominant negative form of the inhibitory immune checkpoint molecule or the receptor thereof, wherein expression of the dominant negative form of the inhibitory immune checkpoint molecule is regulated by an inducible gene expression system. In embodiments, the modified cell comprises a sequence listed in Table 7.

In embodiment, the polynucleotide comprises a polynucleotide encoding a NFAT promoter operatively associated with a nucleotide sequence encoding the inhibitory immune checkpoint molecule or the receptor thereof.

In embodiment, the polynucleotide encoding the NFAT promoter comprises the SEQ ID NO: 67. In embodiment, the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160. In embodiment, the inhibitory immune checkpoint molecule is PD-1. In embodiment, the modified cell comprises at least one of the SEQ ID NOS: 36-42, 45-52, 55-59, 64 and 65. In embodiment, the modified cell comprises a polynucleotide comprising at least one of SEQ ID NOS: 68 and 69. In embodiment, the modified cell comprises a polynucleotide comprising at least one of SEQ ID NOS: 69 and 70.

In embodiment, the binding molecule is a modified TCR or a CAR.

In embodiment, the TCR is derived from spontaneously occurring tumor-specific T cells in patients, the TCR binds to a tumor antigen that comprises CEA, gp100, MART-1, p53, MAGE-A3, or NY-ESO-, or the TCR comprises TCRγ and TCRδ Chains or TCRα and TCRβ chains, or a combination thereof. In embodiment, the CAR comprises an antigen binding domain, a transmembrane domain, and a co-stimulatory domain.

In embodiment, the antigen binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Rα2, Mesothelin, IL-11Rα, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-1 receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, VVT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In embodiment, the transmembrane domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In embodiments, the modified cell is a T cell or an NK cell. In embodiments, the modified cell is engineered to express and secrete a therapeutic agent. In embodiments, the therapeutic agent is or comprises IL-12, IL-6, or IFN-γ. 28. In embodiments, the therapeutic agent is or comprises G-CSF or GM-CSF, or a combination thereof. In embodiments, the therapeutic agent is or comprises at least one of a receptor of G-CSF or GM-CSF, or a combination thereof. In embodiments, the therapeutic agent is or comprises at least one of IL-33, IL-1β, TNFα, MALP-2, IL1, and IL17.

Embodiments relate to an in vitro method for preparing modified cells. The method may include obtaining a sample of cells from the subject. For example, the sample may include T-cells or T-cell progenitors. The method may further include transfecting the cells with a DNA encoding at least a CAR, culturing the population of CAR cells ex vivo in a medium that selectively enhances proliferation of CAR-expressing T-cells.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T-cells.

Embodiments relate to a modified cell comprising a plurality of nucleic acid sequences encoding a first antigen binding molecule, a second antigen binding molecule, and a dominant negative form of an immune checkpoint molecule. Embodiments relate to a modified cell comprising a first binding molecule, a second binding molecule, and a dominant negative form of an immune checkpoint molecule. Embodiments relate to a method of preparing modified cells, the method comprising: administering an effective amount of modified cells. Embodiments relate to a method of causing T cell response, treating a subject having cancer, enhancing cellular treatment on a subject having cancer, or inhibiting growth of tumor cells, the method comprising: intruding into a cell with a plurality of nucleic acid sequences encoding a first antigen binding molecule, a second antigen binding molecule, and a dominant negative form of an immune checkpoint molecule.

Modified cells (e.g., T-cells) may be derived from a stem cell. The stem cells may be adult stem cells, embryonic stem cells, more particularly non-human stem cells, cord blood stem cells, progenitor cells, bone marrow stem cells, induced pluripotent stem cells, totipotent stem cells or hematopoietic stem cells. A modified cell may also be a dendritic cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, Modified cells may be derived from the group consisting of CD4+ T-lymphocytes and CD8+ T-lymphocytes. Prior to expansion and genetic modification of the cells described herein, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art, may be used. In embodiments, modified cells may be derived from a healthy donor, from a patient diagnosed with cancer or from a patient diagnosed with an infection. In embodiments, modified cell is part of a mixed population of cells which present different phenotypic characteristics.

The term "stem cell" refers to any of certain types of cell which have the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cell may be distinguished on the basis of their origin and/or on the extent of their capacity for differentiation into other types of cell. For example, stem cell may include embryonic stem (ES) cells (i.e., pluripotent stem cells), somatic stem cells, Induced pluripotent stem cells, and any other types stem cells.

The pluripotent embryonic stem cells may be found in the inner cell mass of a blastocyst and have high innate capacity for differentiation. For example, pluripotent embryonic stem cells may have the potential to form any type of cell in the body. When grown in vitro for long periods of time, ES cells maintain pluripotency: progeny cells retain the potential for multilineage differentiation.

Somatic stem cells may include the fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited range of types of cell and have been described as multipotent. The 'tissue-specific' stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing a expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells may be made from adult stomach, liver, skin cells and blood cells.

An antigen binding molecule refers to a molecule and/or domain binding a target molecule. In embodiments, the antigen binding molecule may comprise or be a CAR or a TCR (See FIGS. 31 and 32). In embodiments, the antigen binding molecule may comprise or be a binding domain of a bispecific CAR, which includes two binding antigen molecules/domains (See FIG. 33).

An immune checkpoint molecule refers to a molecule that is associated with the T cells and regulates T cell response. In embodiments, the immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160.

Dominant negative mutations have an altered gene product that acts antagonistically to the wild-type allele. These mutations usually result in an altered molecular function (often inactive) and are characterized by a dominant or semi-dominant phenotype. In embodiments, an immune checkpoint molecule is a dominant negative variant of the immune checkpoint molecule is capable of blocking a functional signaling pathway of the immune checkpoint. In embodiments, the immune checkpoint molecule is a receptor of T cells. For example, the dominant negative form of the receptor may include one or more additions, deletions, or substitutions of the wide-type intracellular domain of the receptor such that a signaling pathway of the receptor may be blocked.

In embodiments, the first binding molecule, the second binding molecule, and the dominant negative of the immune checkpoint molecule are expressed as gene products that are separate polypeptides. In embodiments, the first binding molecule is a chimeric antigen receptor (CAR) binding CD19, the second binding molecule is a CAR binding tMUC1, and the dominant negative form of the immune checkpoint molecule is modified PD-1 lacking a functional PD-1 intracellular domain for PD-1/PD-L1 signal transduction. In embodiments, the modified cell comprises a bispecific chimeric antigen receptor (CAR) comprising the first binding molecule and the second binding molecule, the bispecific CAR and the dominant negative of the immune checkpoint molecule are expressed as gene products that are separate polypeptides. In embodiments, the first antigen binding molecule is a first CAR.

In embodiments, the first antigen binding molecule binds a molecule associated with the blood of the subject. In embodiments, the first antigen binding molecule binds a surface molecule of a blood cell or a white blood cell. In embodiments, the first antigen binding molecule binds an antigen of a white blood cell (WBC). In embodiments, the antigen of white blood cell comprises or is CD19, CD22, CD20, BCMA, CD5, CD7, CD2, CD16, CD56, CD30, CD14, CD68, CD11b, CD18, CD169, CD1c, CD33, CD38, CD138, CD13, B7, CAIX, CD123, CD133, CD171, CD171/L1-CAM, CEA, Claudin 18.2, cMet, CS1, CSPG4, Dectin1, EGFR, EGFR vII, EphA2, ERBB receptors, ErbB T4, ERBB2, FAP, Folate receptor 1, FITC, Folate receptor 1, FSH, GD2, GPC3, HA-1 H/HLA-A2, HER2, IL-11Rα, IL13 receptor a2, IL13R, IL13Rα2 (zetakine), Kappa, Leukemia, LewisY, Mesothelin, MUC1, NKG2D, NY-ESO-1, PSMA, ROR-1, TRAIL-receptor1, or VEGFR2. In embodiments, the WBC is a granulocyte, a monocyte and or lymphocyte. In embodiments, the WBC is a B cell. In embodiments, the cell surface molecule of the WBC is CD19.

Blood cells refer to red blood cells (RBCs), white blood cells (WBCs), platelets, or other blood cells. For example, RBCs are blood cells of delivering oxygen (O2) to the body tissues via the blood flow through the circulatory system. Platelets are cells that are involved in hemostasis, leading to the formation of blood clots. WBCs are cells of the immune system involved in defending the body against both infectious disease and foreign materials. There are a number of different types and sub-types of WBCs and each has a different role to play. For example, granulocytes, monocytes, and lymphocytes are 3 major types of white blood cell. There are three different forms of granulocytes: Neutrophils, Eosinophils, Basophils.

A cell surface molecule of a WBC refers to a molecule expressed on the surface of the WBC. For example, the cell surface molecule of a lymphocyte may include CD19, CD22, CD20, BCMA, CD5, CD7, CD2, CD16, CD56, and CD30. The cell surface molecule of a B cell may include CD19, CD20, CD22, BCMA. The cell surface molecule of a monocyte may include CD14, CD68, CD1b, CD18, CD169, and CD1c. The cell surface molecule of granulocyte may include CD33, CD38, CD138, and CD13.

In embodiments, the first binding molecule binds to CD19, CD22, CD20, BCMA, CD5, CD7, CD2, CD16, CD56, CD30, CD14, CD68, CD11b, CD18, CD169, CD1c, CD33, CD38, CD138, or CD13, or the cell surface molecule of the WBC is CD19, CD20, CD22, or BCMA.

In embodiments, the second binding molecule and the first binding molecule bind to different antigens. In embodiments, the second binding molecule binds a solid tumor antigen. In embodiments, the solid tumor antigen comprises or is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, or EGFR. In embodiments, the solid tumor antigen comprises or is B7, CAIX, CD123, CD133, CD171, CD171/L1-CAM, CEA, Claudin 18.2, cMet, CS1, CSPG4, Dectin1, EGFR, EGFR vIII, EphA2, ERBB receptors, ErbB T4, ERBB2, FAP, Folate receptor 1, FITC, Folate receptor 1, FSH, GD2, GPC3, HA-1 H/HLA-A2, HER2, IL-11Rα, IL13 receptor a2, IL13R, IL13Rα2 (zetakine), Kappa, Leukemia, LewisY, Mesothelin, MUC1, NKG2D, NY-ESO-1, PSMA, ROR-1, TRAIL-receptor1, or VEGFR2. In embodiments, the MUC1 is a tumor form of human MUC1 (tMUC1). In embodiments, the MUC1 is a tumor-exclusive epitope of a human MUC1, and the first CAR and the second CAR are expressed as polypeptides.

In embodiments, the MUC1 is a tumor-exclusive epitope of a human MUC1, and the first CAR and the second CAR or the TCR are expressed as separate polypeptides.

In embodiments, the MUC1 is a tumor form of human MUC1 (tMUC1). In embodiments, the first CAR includes a co-stimulatory domain without a signaling domain, such as the CD3 zeta domain, and the MUC1 CAR (second CAR) comprises the MUC1 binding domain, a transmembrane domain, a co-stimulatory, and a CD3 zeta domain.

As used herein, the term "MUC1" refers to a molecule defined as follows. MUC1 is one of the epithelial mucin family of molecules. MUC1 is a transmembrane mucin glycoprotein that is normally expressed on all glandular epithelial cells of the major organs. In normal cells, MUC1 is only expressed on the apical surface and is heavily glycosylated with its core proteins sequestered by the carbohydrates. As cells transform to a malignant phenotype, expression of MUC1 increases several folds, and the expression is no longer restricted to the apical surface, but it is found all around the cell surface and in the cytoplasm. In addition, the glycosylation of tumor associated MUC1 is aberrant, with greater exposure of the peptide core than is found on MUC1 expressed in normal tissues. Little is known regarding the specifics of the aberrant glycosylation.

MUC1 is widely expressed on a large number of epithelial cancers and is aberrantly glycosylated making it structurally and antigenically distinct from that expressed by non-malignant cells (see, e.g., Barratt-Boyes, 1996; Price et al., 1998; Peterson et al., 1991). The dominant form of MUC1 is a high molecular weight molecule comprising a large highly immunogenic extracellular mucin-like domain with a large number of twenty amino acid tandem repeats, a transmembrane region, and a cytoplasmic tail (Quin et al., 2000; McGucken et al., 1995; Dong et al., 1997).

In most epithelial adenocarcinomas including breast and pancreas, MUC1 is overexpressed and aberrantly glycosylated. Adenocarcinoma of the breast and pancreas not only overexpress MUC1 but also shed MUC1 into the circulation. High MUC1 serum levels are associated with progressive disease. MUC1 has been exploited as a prospective biomarker because of the complex and heterogeneous nature of the epitopes expressed within the antigen. MUC1 synthesized by cancerous tissues (e.g., tumor associated MUC1) usually displays an aberrant oligosaccharide profile, which gives rise to the expression of neomarkers such as sialyl-Lea (assayed in the CA19-9 test), sialyl-Lex, and sialyl-Tn (TAG-72), as well as the cryptic epitopes such as Tn.

Several antibodies are being developed against MUC1 for therapeutic use. Pemtumomab (also known as HMFG1) is in Phase III clinical trials as a carrier to deliver the radioisotope Yttrium-90 into tumors in ovarian cancer (reviewed in Scott et al., 2012). CA15-3 (also the HMFG1 antibody), CA27-29, and CA19-9 are all antibodies to MUC1 that are used to assess levels of circulating MUC1 in patients with cancer. However, these antibodies have shown limited utility as therapeutic agents or as biomarkers because they cannot distinguish effectively between MUC1 expressed on normal versus transformed tumor epithelia. In other words, none of these antibodies appear to be targeted to a tumor-specific MUC1 epitope.

A new antibody that is highly specific for a tumor-specific form of MUC1 (tMUC) is designated TAB-004 and is described in U.S. Pat. No. 8,518,405 (see also Curry et al., 2013). While Pemtumomab (HMFG1) was developed using human milk fat globules as the antigen (Parham et al., 1988), TAB-004 was developed using tumors expressing an altered form of MUC1 (Tinder et al., 2008). TAB-004 recognizes the altered glycosylated epitope within the MUC1 tandem repeat sequence. This area is accessible for antigenic detection in tMUC but is blocked from antigenic detection in normal MUC1 by large branches of glycosylation (Gendler, 2001; Mukherjee et al., 2003b; Hollingsworth & Swanson, 2004; Kufe, 2009). Importantly, TAB-004 is different from the epitopes recognized by other MUC1 antibody and has unique complementary determinant regions (CDRs) of the heavy and light chains. The antibody binds the target antigen with a high binding affinity at 3 ng/ml (20 pM) and does not bind unrelated antigens (Curry et al., 2013). Thus, TAB-004 distinguishes between normal and tumor form of MUC1 while HMFG1 (Pemtumomab) does not (see U.S. Pat. No. 8,518,405).

In embodiments, the first antigen binding molecule is a chimeric antigen receptor (CAR) and the second antigen binding molecule is a T Cell Receptor (TCR). In embodiments, the TCR is modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1, or the TCR comprises TCRγ and TCRδ Chains or TCRα and TCRβ chains, or a combination thereof.

In embodiments, the CAR comprises an antigen binding domain, a transmembrane domain, and a co-stimulatory domain. In embodiments, the co-stimulatory domain comprises the intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or a combination thereof. In embodiments, the CAR comprises an antigen binding domain, a transmembrane domain, a co-stimulatory domain, and a CD3 zeta domain. In embodiments, the first and second antigen binding domain is a Fab or an scFv.

In embodiments, the modified cell is a T cell, NK cell, or dendritic cells. In embodiments, the modified cell is a T cell.

In embodiments, immune checkpoint molecule is modified PD-1. In embodiments, the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell. In embodiments, an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1.

In embodiments, the modified cell is engineered to express and secrete a therapeutic agent such as a cytokine. In embodiments, the therapeutic agent that is or comprises IFN-γ. In embodiments, the therapeutic agent that is or comprises IL-6 or IFN-γ, or a combination thereof. In embodiments, the therapeutic agent that is or comprises IL-15 or IL-12, or a combination thereof. In embodiments, the small protein or the therapeutic agent is or comprises a recombinant or native cytokine. In embodiments, the therapeutic agent comprises an FC fusion protein associated with a small protein. In embodiments, the small protein is or comprises IL-12, IL-15, IL-6 or IFN-γ. In embodiments, the therapeutic agent is regulated by Hif1a, NFAT, FOXP3, and/or NFkB.

In embodiments, the therapeutic agent is or includes an antibody reagent (e.g., a single chain antibody (e.g., scFv), a single domain antibody (e.g., a camelid antibody), or a bispecific antibody reagent (e.g., a bispecific T cell engager (BiTE)). In other embodiments, the therapeutic agent is or includes a cytokine. Examples of the cytokines include IL-1β, IL-2, IL-4, IL-5, IL-6, IL-8, IL-10, IL-12, IL-13, IL-15, IL-17, IL-1Rα, IL-2R, IFN-γ, IFN-γ, MIP-In, MIP-IP, MCP-1, TNFα, GM-CSF, GCSF, CXCL9, CXCL10, CXCR factors, VEGF, RANTES, EOTAXIN, EGF, HGF, FGF-P, CD40, CD40L, ferritin, and any combination thereof. In embodiments, the cytokines may include proinflammatory cytokines such as: IFN-γ, IL-15, IL-4, IL-10, TNFα, IL-8, IL-5, IL-6, GM-CSF, and MIP-Iα. For example, IFN-γ has been approved by FDA to treat patients with malignant osteoporosis (e.g., Journal of Pediatrics 121(1):119-24—August 1992).

In embodiments, the modified cell comprises a first targeting vector and a second targeting vector, the first targeting vector comprising a nucleic acid sequence encoding a CAR binding a blood antigen and the therapeutic agent, and the second targeting vector comprises a nucleic acid sequence encoding a CAR biding solid tumor antigen and a dominant negative form of the immune checkpoint molecule. In embodiments, the modified cell comprises a first targeting vector and a second targeting vector, the first targeting vector comprising a nucleic acid sequence encoding a CAR binding CD19 and the therapeutic agent, and the second targeting vector comprises a nucleic acid sequence encoding a CAR biding tMUC1 and a dominant negative form of PD-1. An example of the target vectors is provided in FIG. 36. In these instances, dnPD-1 may enhance persistence of tMUC1 CAR to infiltrate tumor, and the therapeutic agent (e.g., IL-6, IL-12, or IFN-γ) may trigger, cause, and/or enhance immune responses of the subject, together leading enhanced tMUC1 CAR T treatment on solid tumor.

In embodiments, the modified cell is derived form a healthy donor or the subject having the cancer. In embodiments the modified cell has a reduced expression of endogenous TRAC gene. In embodiments, the modified cell further the endogenous TRAC gene that has been inactivated in the CAR T cell to avoid GVHD and rejection. For example, the CAR T cell has a reduced expression of endogenous TRAC gene. In embodiments, the CAR T cell lacks expression of a functional endogenous TCR and/or produces substantially impaired endogenous TCR on its surface such that the endogenous TCR will not substantially elicit an adverse immune reaction in a host, e.g., a GVHD reaction. In some instances, progeny of the CAR T cell may also be reasonably expected to lack expression of a functional endogenous TCR and/or produces substantially impaired endogenous TCR on their surface such that the progeny of the endogenous TCR will not substantially elicit an adverse immune reaction in a host, e.g., a GVHD reaction. In embodiments, the TCR is or is derived from a healthy human donor having HLA type that matches the recipient. Typically, matching is performed on the basis of variability at three or more loci of the HLA gene, and a perfect match at these loci is preferred. In some instances, allogeneic transplant donors may be related (usually a closely HLA matched sibling), syngeneic (a monozygotic 'identical' twin of the patient) or unrelated (donor who is not related and found to have very close degree of HLA matching). The HLA genes fall in two categories (Type I and Type II). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease. In other embodiments, endogenous HLA I gene of the CAR T cell may be further inactivated to avoid recipient's rejection of the donor's CAR T cell.

Embodiments relate to a modified cell comprising a plurality of nucleic acid sequences encoding a binding molecule and a molecule associated with T cell modulation, wherein expression of the molecule is regulated by an inducible gene expression system. Embodiments relate to a modified cell comprising a plurality of nucleic acid sequences encoding a binding molecule and a molecule associated with T cell modulation, wherein expression of the molecule or disruption of the corresponding gene is regulated by an inducible gene expression system.

Embodiments relate to a method of preparing modified cells, the method comprising: intruding into cells with a plurality of nucleic acid sequences encoding a binding molecule and a molecule associated with T cell modulation, wherein expression of the molecule or disruption of the corresponding gene is regulated by an inducible gene expression system. Embodiments relate to a method of causing T cell response, treating a subject having cancer, enhancing cellular treatment on a subject having cancer, or inhibiting growth of tumor cells, the method comprising: administering an effective amount of modified cells of one of claims 1 and 2 to the subject. In embodiments, the method further comprises monitoring cytokine releases of the subject in response to the CAR infusion; and administering an effective amount of an inducer corresponding to the modified cells in a predetermined condition (e.g., in response to determination that a level of one or more cytokines increases and/or reaches a peak level). In embodiments, the method further comprises administering an effective amount of an inducer corresponding to the modified cells in a predetermined condition. In embodiments, administering an effective amount of an inducer corresponding to the modified cells after or when the modified cells are infused to the subject.

In embodiments, the modified cell comprises disruption of one or more genes associated with the molecule. For example, the disruption may include deletion, addition, knockout of the one or more genes or interference with expression of the one or more genes. Various techniques (e.g., Cre-Lox recombination) may be implemented to generate modified T cells having inducible disruption of the gene associated with the biosynthesis or transportation of the molecule in the T cells. For example, the molecule is or comprises LRCH1, PD-1, PD-L1, YAP, Foxo1, Spry1/2, IL-35, CXCR2, and TIGIT. The conditional gene disruption may be implemented by the techniques described in, for example, Inducible Genome Editing with Conditional CRISPR/Cas9 Mice 2018 May 4; 8(5):1627-1635. doi: 10.1534/g3.117.300327, which is hereby incorporated by reference in its entirety.

In embodiments, the molecule is or comprises a therapeutic agent. In embodiments, the molecule is selected from a group consist of FBXO38, DOCK8, CDC42, Bcl6, HS-CD6, Pck1, and TLR9. In embodiments, overexpression of the molecule on T cells enhances T cell response, reduces inhibitory effect on the T cells, increases proliferative and/or reconstitute capacities of the T cells, enhances killing functions of the T cells, enhances mobility of the T cells, or helps development of follicular helper T cells. For example, the proliferative and/or reconstitute capacities of T cells are measured based on expression of one or more markers of the T cells. FBXO38 is an E3 ubiquitin ligase of PD-1 that mediates the ubiquitination of PD-1 to ensure that PD-1 maintains normal levels and normal T cell function. In Fbxo38 knockout mice, high expression of PD-1 in tumor infiltrating lymphocytes resulted in rapid tumor growth in mice. Designed to overexpress FBXO38 molecules in T cells. LRCH1 can inhibit the migration and killing of T cells, and DOCK8 can promote T cell migration and killing. One of the genes upregulated in IL-2 producing CD4+ T cells is Bcl6, which is important for Tfh cell development and is designed to overexpress the Bcl6 gene in T cells. HS-CD6 on the surface of T cells enhances adhesion between T cells and endothelial cells expressing ALCAM, thereby promoting migration. Engineered T cells (carrying HS-CD6+CAR) can significantly reduce tumor volume. TLR9 contributes to tumor regression by inducing cytotoxic T cell response (CTL), reducing the numbers of myeloid-derived suppressor cells (MDSCs), the tumor-associated macrophages (TAMs) and the regulatory T cells (T regs).

In embodiments, the expression of the one or more markers of the T cell without the presence of an antigen that the T cell recognizes is greater or lower than a T cells without modulation and the one or more markers are provided in Table 1. In embodiments, the expression of the one or more markers of the T cell in response to the presence of an antigen that the T cell recognizes is greater or lower than a T cells without modulation and the one or more markers are provided in Table 2.

TABLE 1

| | |
|---|---|
| CD45RO | lower |
| CCR7 | greater |
| CD45RA | greater |
| CD62L | greater |
| CD27 | greater |
| CD28 | greater |

TABLE 1-continued

| | |
|---|---|
| IL-7Rα | greater |
| CD95 | greater |
| IL-2Rβ | greater |
| CXCR3 | greater |
| LFA-1 | greater |
| CD25 | lower |
| KLRG1 | lower |

TABLE 2

| | |
|---|---|
| CD25 | lower |
| CD69 | lower |
| CD107α | lower |
| CD137 | lower |
| CD40L | lower |
| OX40 | lower |
| CD27 | greater |
| CD28 | greater |
| Erk phosphorylation | lower |
| Akt phosphorylation | lower |

In embodiments, the proliferative and/or reconstitute capacities of T cells are measured based on release and/or expression of one or more proteins of the T cells. In embodiments, the one or more proteins are one or more cytokines released and/or expressed by the T cells. In embodiments, the release and/or expression of one or more cytokines by the T cells in response to the presence of an antigen that the T cell recognizes is greater or lower than a T cells without modulation and the one or more markers are provided in Table 3.

TABLE 3

| | |
|---|---|
| IL2 | lower |
| IL4 | lower |
| IL6 | lower |
| IL10 | lower |
| TNFα | lower |
| IFNγ | lower |

In embodiments, the inhibitory capacities of T cells are measured based on expression of one or more markers of the T cells. In embodiments, the expression of the one or more markers of the T cell without the presence of an antigen that the T cell recognizes is greater or lower than a T cells without modulation and the one or more markers are provided in Table 4. In embodiments, the expression of the one or more markers of the T cell in response to the presence of an antigen that the T cell recognizes is greater or lower than a T cells without modulation and the one or more markers are provided in Table 5.

TABLE 4

| | |
|---|---|
| CD45RO | greater |
| CCR7 | lower |
| CD45RA | lower |
| CD62L | lower |
| CD27 | lower |
| CD28 | lower |
| IL-7Rα | lower |
| CD95 | lower |
| IL-2Rβ | lower |
| CXCR3 | lower |
| LFA-1 | lower |
| CD25 | greater |
| KLRG1 | greater |

TABLE 5

| | |
|---|---|
| CD25 | greater |
| CD69 | greater |
| CD107α | greater |
| CD137 | greater |
| CD40L | greater |
| OX40 | greater |
| CD27 | lower |
| CD28 | lower |
| Erk phosphorylation | greater |
| Akt phosphorylation | greater |

In embodiments, the proliferative and/or reconstitute capacities of T cells are measured based on release and/or expression of one or more proteins of the T cells. In embodiments, the one or more proteins are one or more cytokines released and/or expressed by the T cells. In embodiments, the release and/or expression of one or more cytokines by the T cells in response to the presence of an antigen that the T cell recognizes is greater or lower than a T cells without modulation and the one or more markers are provided in Table 6.

TABLE 6

| | |
|---|---|
| IL2 | greater |
| IL4 | greater |
| IL6 | greater |
| IL10 | greater |
| TNFα | greater |
| IFNγ | greater |

Embodiments relate to a modified cell comprising a plurality of nucleic acid sequences encoding a binding molecule and a dominant negative form of an inhibitory immune checkpoint molecule or a receptor thereof, wherein expression of the dominant negative form of the inhibitory immune checkpoint molecule is regulated by an inducible gene expression system. Embodiments relate to a modified cell comprising a binding molecule, and a dominant negative form of an inhibitory immune checkpoint molecule, wherein expression of the dominant negative form of the inhibitory immune checkpoint molecule is regulated by an inducible gene expression system. Embodiments relate to a method of preparing modified cells, the method comprising: administering an effective amount of modified cells. Embodiments relate to a method of causing T cell response, treating a subject having cancer, enhancing cellular treatment on a subject having cancer, or inhibiting growth of tumor cells, the method comprising: intruding into cells with a plurality of nucleic acid sequences encoding a binding molecule and a dominant negative form of an inhibitory immune checkpoint molecule to obtain modified cells, expression of the dominant negative form of the inhibitory immune checkpoint molecule regulated by an inducible gene expression system; and administering an effective amount of modified cells to the subject. In embodiments, the binding molecule and the dominant negative of the inhibitory immune checkpoint molecule are expressed as gene products that are separate polypeptides.

Figure 7:
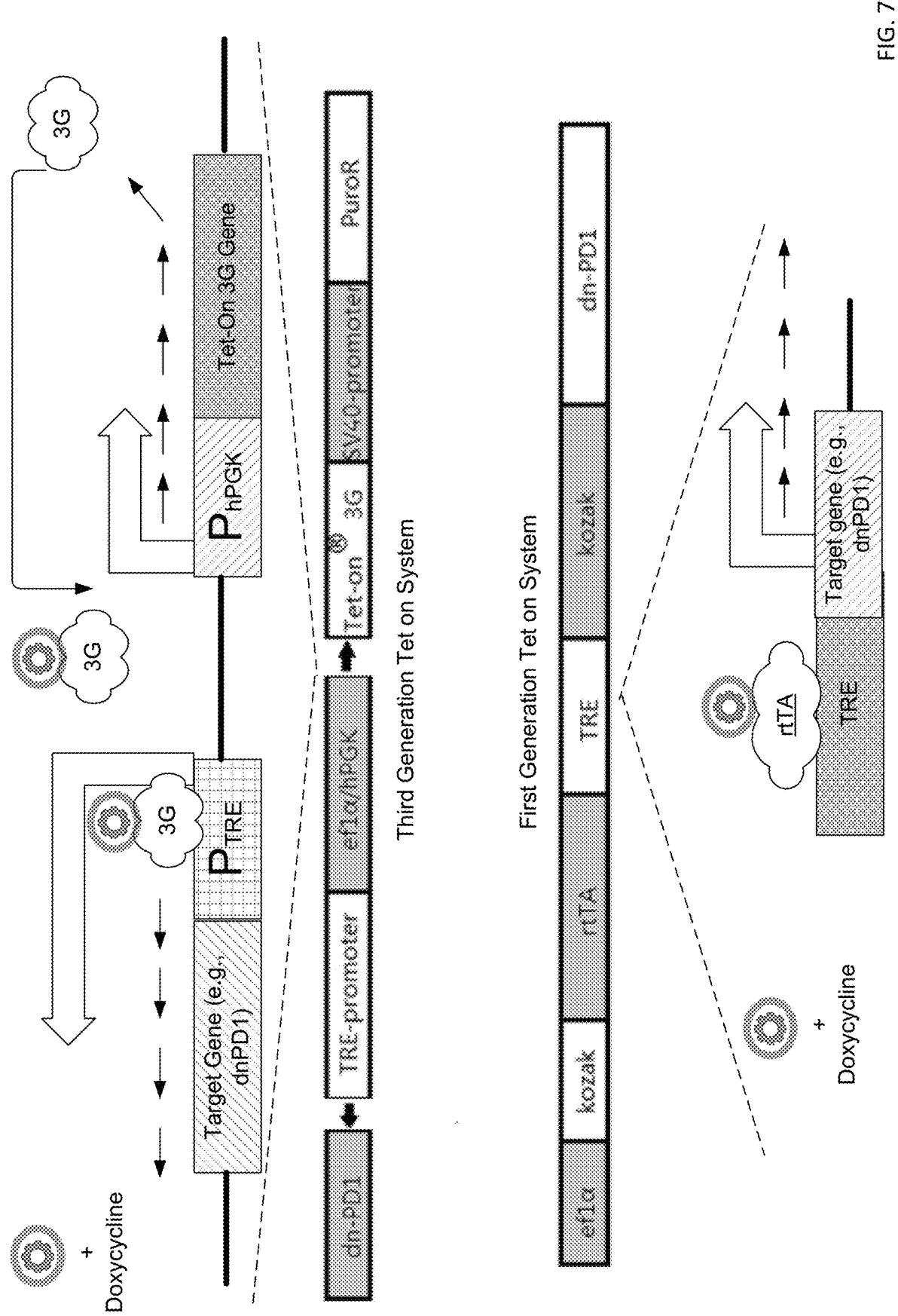
FIG. 7 is schematic diagrams showing two constructs of inducible gene expression systems that control expression of dnPD-1.

In embodiments, the inducible gene expression system comprises or is a lac system, a tetracycline system, or a galactose system. In embodiments, the inducible gene expression system comprises or is a tetracycline system. Inducible gene expression may be implemented by an inducible system including an inducible promoter capable of controlling gene expression in Eukaryotic cells (e.g., T cells). In embodiments, the inducible gene expression system comprises or is a tetracycline on system, and an agent (e.g., inducer) is tetracycline, doxycycline, or an analog thereof. Thus, in the present of the inducer (e.g., tetracycline, doxycycline or minocycline), the transactivator rtTA is activated as to drive the expression of dnPD-1 (See FIG. 7). Examples of the inducible system include lac system, tet system. For example, the tet system includes a TRE, which is 7 repeats of a 19 nucleotide tetracycline operator (tetO) sequence, and is recognized by the tetracycline repressor (tetR). In the endogenous bacterial system, if tetracycline, or one of its analogs like doxycycline, are present, tetR will bind to tetracycline and not to the TRE, permitting transcription. Tetracycline-dependent promoters are developed by placing a TRE upstream of a minimal promoter. There are two types of tet systems: tetracycline off system and tetracycline on system. As for tetracycline off system, in the absence of tetracycline, the tetR portion of tTA will bind these tetO sequences and the activation domain promotes expression. In the presence of tetracycline, tetracycline binds to tetR. This precludes tTA binding to the tetO sequences and subsequent increase in expression by the activation domain, resulting in reduced gene expression. This idea of a hybrid transactivator was initially used with the lac system. Tetracycline off is also known as the tTA-dependent system. As for tetracycline on system, random mutagenesis was used to identify which amino acid residues of tetR were important for tetracycline-dependent repression. Mutating these residues led to the development of a reverse Tet repressor, or rTetR, which reversed the phenotype and created a reliance on the presence of tetracycline for induction, rather than repression. The new transactivator rtTA (reverse tetracycline-controlled transactivator) was created by fusing rTetR with VP16. The tetracycline on system is also known as the rtTA-dependent system. Based on the transcriptional regulators described by Gossen and Bujard, 1992; Gossen et al. 1995; and Urlinger et al. 2000, Tet-On 3G is a modified form of the Tet-Advanced transactivator protein which has been altered to display far higher sensitivity to doxycycline (Dox) (Zhou et al. 2006). Tet-One systems typically reach maximum expression with only 10 ng/ml Dox, approximately two orders of magnitude lower than required for the first generation of Tet-On systems.

In embodiments, the method further comprises intruding into cells with a plurality of nucleic acid sequences encoding the binding molecule and the dominant negative form of the inhibitory immune checkpoint molecule to obtain the modified cells. In embodiments, the method further comprises monitoring cytokine releases of the subject in response to the CAR infusion; and wherein the administering the effective amount of the inhibitor of the inhibitory immune checkpoint molecule or the receptor thereof in response to the predetermined condition comprises administering the effective amount of an inducer corresponding to the inducible gene expression system to express the inhibitory immune checkpoint molecule on the modified cells in response to a predetermined condition.

In embodiments, the method further comprises monitoring cytokine releases of the subject in response to the CAR infusion; and wherein the administering the effective amount of the inhibitor of the inhibitory immune checkpoint molecule or the receptor thereof in response to the predetermined condition comprises administering the effective amount of an inducer corresponding to the inducible gene expression system to express the inhibitory immune checkpoint molecule on the modified cells in response to determination that a level of one or more cytokines increases and/or reaches a peak level. In embodiments, the method further comprises terminating the administering of the inducer in response to determination that the level drops to a base level.

Figure 8:
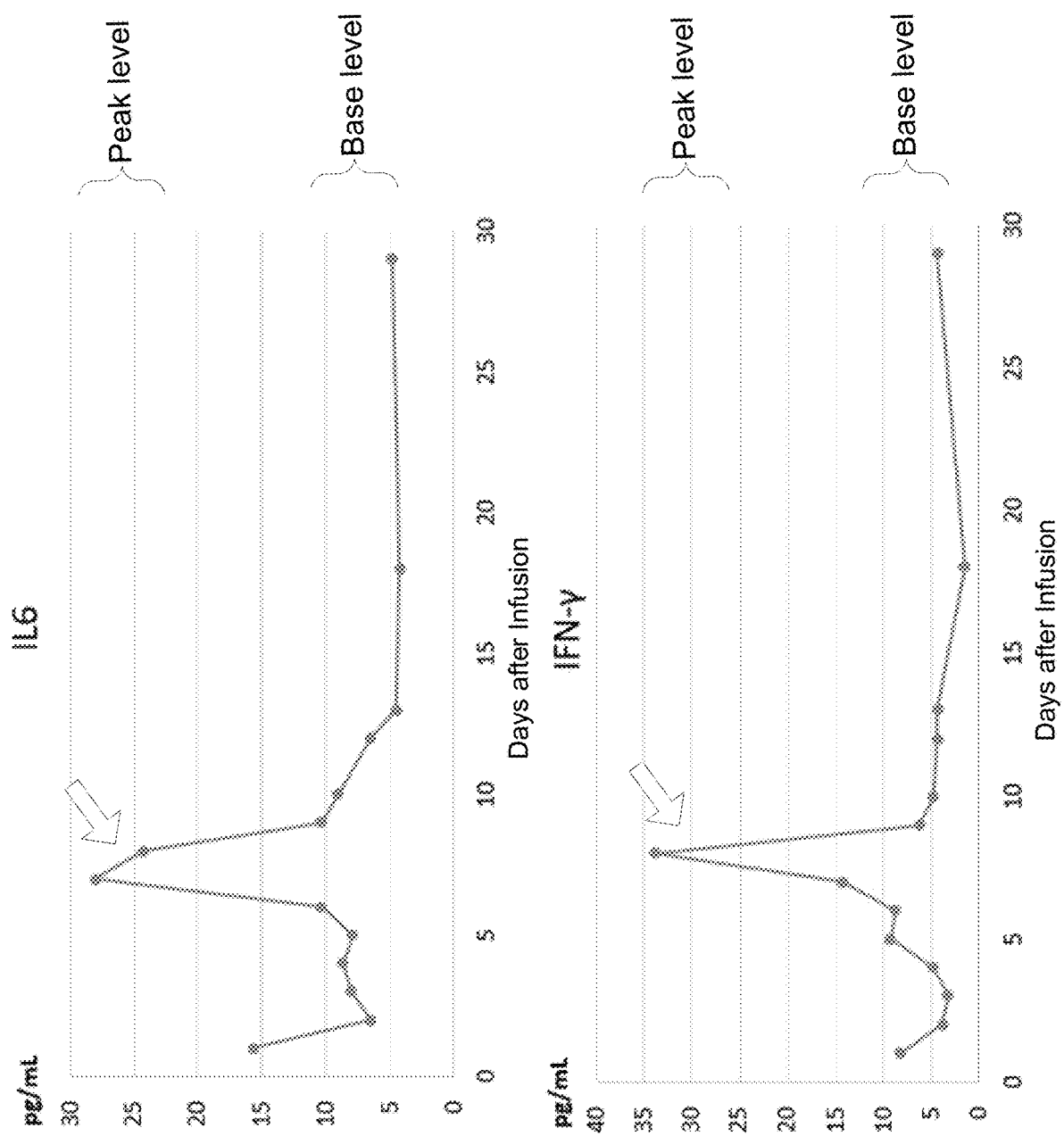
FIG. 8 shows a scheme of administering an agent (e.g., an inhibitor or inducer) in an exemplary adoptive cell therapy. Arrows indicate the time when an agent (e.g., inhibitor or inducer) is administered to a subject, for example at the peak of cytokine release.

Embodiments relate to a method of causing T cell response, treating a subject having cancer, enhancing cellular treatment on a subject having cancer, or inhibiting growth of tumor cells, the method comprising: administering an effective amount of modified cells comprising a binding molecule to the subject; and administering an effective amount of an inhibitor of an inhibitory immune checkpoint molecule or a receptor thereof in response to a predetermined condition. In embodiments, the method further comprises intruding into cells with a plurality of nucleic acid sequences encoding the binding molecule to obtain the modified cells. In embodiments, the method further comprises monitoring cytokine releases of the subject in response to the CAR infusion; and wherein the administering the effective amount of the inhibitor of the inhibitory immune checkpoint molecule or the receptor thereof in response to the predetermined condition comprises administering the effective amount of the inhibitor of the inhibitory immune checkpoint molecule or the receptor thereof in response to determination that a level of one or more cytokines increases and/or reaches a peak level. In embodiments, the method further comprises terminating the administering of the inhibitor in response to determination that the level drops to a base level. In embodiments, the cytokine may include IL6 and/or IFNγ, as shown in FIG. 8.

In embodiments, the CAR comprises an antigen binding domain, a transmembrane domain, and a co-stimulatory domain. In embodiments, the co-stimulatory domain comprises the intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or a combination thereof. In embodiments, the CAR comprises an antigen binding domain, a transmembrane domain, a co-stimulatory domain, and a CD3 zeta domain. In embodiments, the and additional antigen binding domain is a Fab or a scFv. In embodiments, the modified cell is a T cell, NK cell, or dendritic cells. In embodiments, the modified cell is a T cell.

In embodiments, the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160. In embodiments, inhibitory immune checkpoint molecule is modified PD-1. In embodiments, the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell. In embodiments, an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1. In embodiments, inhibitory immune checkpoint molecule may include a molecule related to the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160. For example, the inhibitory immune checkpoint molecule is Singlec-15. Siglec-15 is a type-I transmembrane protein consisting of: (i) two immunoglobulin (Ig)-like domains, (ii) a transmembrane domain containing a lysine residue, and (iii) a short cytoplasmic tail. Siglec-15 is expressed on macrophages and/or dendritic cells of human spleen and lymph nodes. We show that the extracellular domain of Siglec-15 preferentially recognizes the Neu5Acalpha2-6GalNAcalpha-structure. Siglec-15 associates with the activating adaptor proteins DNAX activation protein (DAP)12 and DAP10 via its lysine residue in the transmembrane domain, implying that it functions as an activating signaling molecule.

In embodiments, the modified cell is engineered to express and secrete a therapeutic agent such as a cytokine. In embodiments, the therapeutic agent that is or comprises IFN-γ. In embodiments, the therapeutic agent that is or comprises IL-6 or IFN-γ, or a combination thereof. In embodiments, the therapeutic agent that is or comprises IL-15 or IL-12, or a combination thereof. In embodiments, the small protein or the therapeutic agent is or comprises a recombinant or native cytokine. In embodiments, the therapeutic agent comprises a FC fusion protein associated with a small protein. In embodiments, the small protein is or comprises IL-12, IL-15, IL-6 or IFN-γ. In embodiments, the therapeutic agent is regulated by Hif1a, NFAT, FOXP3, and/or NFkB.

In embodiments, the modified cell is derived form a healthy donor or the subject having the cancer. In embodiments, the c modified ell has a reduced expression of endogenous TRAC gene.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:
1. A modified cell comprising a plurality of nucleic acid sequences encoding a binding molecule and a molecule associated with T cell modulation, wherein expression of the molecule associated with T cell modulation or disruption of the corresponding gene of the molecule associated with T cell modulation is regulated by an inducible gene expression system.
2. A modified cell comprising a binding molecule and a molecule associated with T cell modulation, wherein expression of the molecule associated with T cell modulation or disruption of the corresponding gene of the molecule associated with T cell modulation is regulated by an inducible gene expression system.
3. A method of preparing modified cells, the method comprising: introducing into cells a plurality of nucleic acid sequences encoding a binding molecule and a molecule associated with T cell modulation, wherein expression of the molecule associated with T cell modulation or disruption of the corresponding gene of the molecule associated with T cell modulation is regulated by an inducible gene expression system.
4. A method of causing T cell response, treating a subject having cancer, enhancing cellular treatment of a subject having cancer, or inhibiting growth of tumor cells, the method comprising: administering an effective amount of modified cells of embodiment 1 or 2 to the subject.
5. The method of embodiment 4, the method further comprising: monitoring cytokine release of the subject in response to the administration of the modified cells; and administering an effective amount of an inducer corresponding to the modified cells in response to a predetermined condition (e.g., in response to determination that a level of one or more cytokines increases and/or reaches a peak level), the inducer corresponding to the inducible gene expression system to express the inhibitory immune.
6. The method of embodiment 3 or 4, further comprising: administering an effective amount of an inducer corresponding to the modified cells in response to a predetermined condition.
7. The method of embodiment 3 or 4, further comprising: administering an effective amount of an inducer corresponding to the modified cells subsequent to or with the administration of the modified cells to the subject.
8. The modified cell or the method of any one of embodiments 1-5, wherein the molecule associated with T cell modulation is or comprises a therapeutic agent.
9. The modified cell or the method of any one of embodiments 1-5, wherein the molecule associated with T cell modulation is selected from a group consist of FBXO38, DOCK8, CDC42, Bcl6, HS-CD6, and TLR9.
10. The modified cell or the method of any one of embodiments 1-5, wherein overexpression of the molecule associated with T cell modulation on T cells enhances T cell response, reduce inhibitory effect on the T cells, increases proliferative and/or reconstitute capacities of the T cells, enhances killing functions of the T cells, enhances mobility of the T cells, or helps development of follicular helper T cells.
11. A modified cell comprising a plurality of nucleic acid sequences encoding a binding molecule and an antibody blocking an inhibitory immune checkpoint molecule or a receptor of the inhibitory immune checkpoint molecule, wherein expression of the antibody is regulated by an inducible gene expression system.
12. A modified cell comprising a plurality of nucleic acid sequences encoding a binding molecule and an antibody blocking an inhibitory immune checkpoint molecule or a receptor of the inhibitory immune checkpoint molecule, wherein expression of the antibody is regulated by an inducible gene expression system.
13. A method of preparing modified cells, the method comprising: introducing into cells a plurality of nucleic acid sequences encoding a binding molecule and an antibody blocking an inhibitory immune checkpoint molecule to obtain modified cells, wherein expression of the antibody blocking the inhibitory immune checkpoint molecule is regulated by an inducible gene expression system.
14. A method of causing T cell response, treating a subject having cancer, enhancing cellular treatment of a subject having cancer, or inhibiting growth of tumor cells, the method comprising: administering an effective amount of the modified cells of embodiment 11 or 12 to the subject.

15. The method of any one of embodiments 11-14, wherein the antibody blocking the inhibitory immune checkpoint or a receptor (e.g., PD-1 or PD-L1) of the inhibitory immune checkpoint molecule is a scFv.

16. A modified cell comprising a plurality of nucleic acid sequences encoding a binding molecule and an extracellular domain of an inhibitory immune checkpoint molecule or a receptor thereof, wherein expression of the extracellular domain is regulated by an inducible gene expression system.

17. A modified cell comprising a plurality of nucleic acid sequences encoding a binding molecule and an extracellular domain of an inhibitory immune checkpoint molecule or a receptor of the inhibitory immune checkpoint molecule, wherein expression of the extracellular domain is regulated by an inducible gene expression system.

18. A method of preparing modified cells, the method comprising: introducing into cells a plurality of nucleic acid sequences encoding a binding molecule and an extracellular domain of an inhibitory immune checkpoint molecule to obtain modified cells, wherein expression of the extracellular domain of the inhibitory immune checkpoint molecule is regulated by an inducible gene expression system.

19. A method of causing T cell response, treating a subject having cancer, enhancing cellular treatment of a subject having cancer, or inhibiting growth of tumor cells, the method comprising: administering an effective amount of modified cells of embodiment 16 or 17 to the subject.

20. The method of any one of embodiments 13, 14, 15, 18, and 19, further comprising: monitoring cytokine release of the subject in response to the administration of the modified cells; wherein administering the effective amount of the antibody blocking the inhibitory immune checkpoint molecule or the receptor of the inhibitory immune checkpoint molecule comprises administering an effective amount of an inducer corresponding to the inducible gene expression system to express the antibody blocking the inhibitory immune checkpoint molecule on the modified cells in response to determination that a level of one or more cytokines has increased and/or has reached a peak level.

21. A modified cell comprising a plurality of nucleic acid sequences encoding a binding molecule and a dominant negative form of an inhibitory immune checkpoint molecule or a receptor of the inhibitory immune checkpoint molecule, wherein expression of the dominant negative form of the inhibitory immune checkpoint molecule is regulated by an inducible gene expression system.

22. A modified cell comprising a binding molecule, and a dominant negative form of an inhibitory immune checkpoint molecule, wherein expression of the dominant negative form of the inhibitory immune checkpoint molecule is regulated by an inducible gene expression system.

23. A method of preparing modified cells, the method comprising: administering an effective amount of modified cells of embodiment 11 or 12.

24. A method of causing T cell response, treating a subject having cancer, enhancing cellular treatment of a subject having cancer, or inhibiting growth of tumor cells, the method comprising: introducing into cells with a plurality of nucleic acid sequences encoding a binding molecule and a dominant negative form of an inhibitory immune checkpoint molecule to obtain modified cells, wherein expression of the dominant negative form of the inhibitory immune checkpoint molecule is regulated by an inducible gene expression system; and administering an effective amount of the modified cells to the subject.

25. The modified cell and the method of any one of embodiments 1-24, wherein the inducible gene expression system comprises or is a lac system, a tetracycline system, or a galactose system.

26. The modified cell and the method of embodiment 25, wherein the inducible gene expression system comprises or is a tetracycline system.

27. The modified cell and the method of embodiment 26, wherein the inducible gene expression system comprises or is a tetracycline on system, and an inducer is tetracycline, doxycycline, or an analog thereof.

28. The modified cell or the method of any one of embodiments 11-27, wherein the binding molecule and the dominant negative of the inhibitory immune checkpoint molecule are expressed as gene products that are separate polypeptides.

29. The method of any one of embodiments 23-28, further comprising: introducing into cells a plurality of nucleic acid sequences encoding the binding molecule and the dominant negative form of the inhibitory immune checkpoint molecule to obtain the modified cells.

30. The method of any one of embodiments 23-28, further comprising: monitoring cytokine release of the subject in response to the administration of the modified cells; and wherein the administering the effective amount of the inhibitor of the inhibitory immune checkpoint molecule or the receptor of the inhibitory immune checkpoint molecule comprises administering the effective amount of an inducer corresponding to the inducible gene expression system to express the dominant negative form of the inhibitory immune checkpoint molecule on the modified cells in response to a predetermined condition.

31. The method of any one of embodiments 23-28, further comprising:
monitoring cytokine release of the subject in response to the administration of the modified cells; and wherein the administering the effective amount of the inhibitor of the inhibitory immune checkpoint molecule or the receptor thereof comprises administering the effective amount of an inducer corresponding to the inducible gene expression system to express the dominant negative form of the inhibitory immune checkpoint molecule on the modified cells in response to determination that a level of one or more cytokines has increased and/or has reached a peak level.

32. The method of embodiment 31, further comprising:
terminating the administering of the inducer in response to determination that the level has decreased to a base level.

33. The modified cell or the method of any one of embodiments 1-32, wherein the modified cell further comprises an additional binding molecule.

34. The modified cell or the method of embodiment 33, wherein the binding molecule is a chimeric antigen receptor (CAR) binding CD19, the additional binding molecule is a CAR binding tMUC1, and the dominant negative form of the inhibitory immune checkpoint molecule is modified PD-1 lacking a functional PD-1 intracellular domain for PD-1/PD-L1 signal transduction.

35. The modified cell or the method of embodiment 33, wherein the modified cell comprises a bispecific chimeric antigen receptor (CAR) comprising the binding molecule and the additional binding molecule, wherein the bispecific CAR and the dominant negative of the immune checkpoint molecule or the receptor of the inhibitory immune checkpoint molecule are expressed as gene products that are separate polypeptides.

36. The modified cell or the method of one of embodiments 1-32, wherein the binding molecule is a CAR.

37. The modified cell or the method of embodiment 33, wherein the binding molecule binds a surface molecule of a blood cell or a white blood cell, or the binding molecule binds an antigen of a white blood cell (WBC).

38. The modified cell or the method of embodiment 33, wherein the binding molecule binds a molecule associated with blood cells of the subject.

39. The modified cell or the method of embodiment 37 or 38, wherein the antigen of white blood cell (WBC) comprises or is CD19, CD22, CD20, BCMA, CD5, CD7, CD2, CD16, CD56, CD30, CD14, CD68, CD11b, CD18, CD169, CD1c, CD33, CD38, CD138, CD13, B7, CAIX, CD123, CD133, CD171, CD171/L1-CAM, CEA, Claudin 18.2, cMet, CS1, CSPG4, Dectin1, EGFR, EGFR vIII, EphA2, ERBB receptors, ErbB T4, ERBB2, FAP, Folate receptor 1, FITC, Folate receptor 1, FSH, GD2, GPC3, HA-1 H/HLA-A2, HER2, IL-11Rα, IL13 receptor a2, IL13R, IL13Rα2 (zetakine), Kappa, Leukemia, LewisY, Mesothelin, MUC1, NKG2D, NY-ESO-1, PSMA, ROR-1, TRAIL-receptor1, or VEGFR2.

40. The modified cell or the method of embodiment 37, wherein the WBC is a granulocyte, a monocyte, or lymphocyte.

41. The modified cell or the method of embodiment 37, wherein the WBC is a B cell.

42. The modified cell or the method of any one of embodiments 37-41, wherein the cell surface molecule of the WBC is CD19.

43. The modified cell or the method of any one of embodiments 1-42, wherein the binding molecule binds to CD19, CD22, CD20, BCMA, CD5, CD7, CD2, CD16, CD56, CD30, CD14, CD68, CD11b, CD18, CD169, CD1c, CD33, CD38, CD138, or CD13, or the cell surface molecule of the WBC is CD19, CD20, CD22, or BCMA.

44. The modified cell or the method of any one of embodiments 33-43, wherein the additional binding molecule and the binding molecule bind to different antigens.

45. The modified cell or the method of any one of embodiments 33-43, wherein the additional binding molecule binds a solid tumor antigen.

46. The modified cell or the method of embodiment 45, wherein the solid tumor antigen comprises or is PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, or EGFR.

47. The modified cell or the method of embodiment 46, wherein the solid tumor antigen comprises or is B7, CAIX, CD123, CD133, CD171, CD171/L1-CAM, CEA, Claudin 18.2, cMet, CS1, CSPG4, Dectin1, EGFR, EGFR vIII, EphA2, ERBB receptors, ErbB T4, ERBB2, FAP, Folate receptor 1, FITC, Folate receptor 1, FSH, GD2, GPC3, HA-1 H/HLA-A2, HER2, IL-11Rα, IL13 receptor a2, IL13R, IL13Rα2 (zetakine), Kappa, Leukemia, LewisY, Mesothelin, MUC1, NKG2D, NY-ESO-1, PSMA, ROR-1, TRAIL-receptor1, or VEGFR2.

48. The modified cell or the method of embodiment 46, wherein the MUC1 is a tumor form of human MUC1 (tMUC1).

49. The modified cell or the method of embodiment 46, wherein the MUC1 is a tumor-exclusive epitope of a human MUC1, and the CAR and the additional CAR are expressed as polypeptides.

50. The modified cell or the method of embodiment 33, wherein the binding molecule is a chimeric antigen receptor (CAR) and the additional binding molecule is a T Cell Receptor (TCR).

51. The modified cell or the method of embodiment 50, wherein the TCR is modified TCR.

52. The modified cell or the method of embodiment 50, wherein the TCR is derived from spontaneously occurring tumor-specific T cells in patients.

53. The modified cell or the method of embodiment 50, wherein the TCR binds a tumor antigen.

54. The modified cell or the method of embodiment 50, wherein the tumor antigen comprises CEA, gp100, MART-1, p53, MAGE-A3, or NY-ESO-1, or the TCR comprises TCRγ and TCRδ Chains or TCRα and TCRβ chains, or a combination thereof.

55. A method of causing T cell response, treating a subject having cancer, enhancing cellular treatment of a subject having cancer, or inhibiting growth of tumor cells, the method comprising: administering an effective amount of modified cells comprising a binding molecule to the subject; and administering an effective amount of an inhibitor of an inhibitory immune checkpoint molecule or a receptor of the inhibitory immune checkpoint molecule in response to a predetermined condition.

56. The method of embodiment 55, further comprising: introducing into cells a plurality of nucleic acid sequences encoding the binding molecule to obtain the modified cells.

57. The method of embodiment 55 or 56, further comprising: monitoring cytokine release of the subject in response to the administration of modified cells; and wherein administering the effective amount of the inhibitor of the inhibitory immune checkpoint molecule or the receptor of the inhibitory immune checkpoint molecule comprises administering the effective amount of the inhibitor of the inhibitory immune checkpoint molecule or the receptor thereof in response to determination that a level of one or more cytokines increases and/or reaches a peak level.

58. The method of embodiment 57, further comprising: terminating the administering of the inhibitor in response to determination that the level has decreased to a base level.

59. The modified cell or the method of one of embodiments 1-49, wherein the CAR comprises an antigen binding domain, a transmembrane domain, and a co-stimulatory domain.

60. The modified cell or the method of embodiment 59, wherein the co-stimulatory domain comprises the intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds CD83, or a combination thereof.

61. The modified cell or the method of any one of embodiments 1-51, wherein the CAR comprises an antigen binding domain, a transmembrane domain, a co-stimulatory domain, and a CD3 zeta domain.

62. The modified cell or the method of any one of embodiments 1-52, wherein the additional antigen binding domain is a Fab or a scFv.

63. The modified cell or the method of any one of embodiments 1-53, wherein the modified cell is a T cell, NK cell, or dendritic cells.

64. The modified cell or the method of any one of embodiments 1-53, wherein the modified cell is a T cell.
65. The modified cell or the method of any one of embodiments 1-55, wherein the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160.
66. The modified cell or the method of embodiment 65, wherein inhibitory immune checkpoint molecule is modified PD-1.
67. The modified cell or the method of embodiment 65, wherein the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell.
68. The modified cell or the method of embodiment 65, wherein an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1.
69. The modified cell or the method of any one of embodiments 11-59, wherein the modified cell is engineered to express and secrete a therapeutic agent such as a cytokine.
70. The modified cell or the method of embodiment 8 or 69, wherein the therapeutic agent is or comprises IFN-γ, or the therapeutic agent is or comprises IL-6 or IFN-γ, or the therapeutic agent comprises IFN-γ, IL-6, or a combination thereof.
71. The modified cell or the method of embodiment 8 or 69, wherein the therapeutic agent is or comprises IL-15, or IL-12, or a combination thereof.
72. The modified cell or the method of embodiment 8 or 69, wherein the therapeutic agent is or comprises a recombinant or native cytokine.
73. The modified cell or the method of embodiment 8 or 69, wherein the therapeutic agent comprises a FC fusion protein associated with a small protein, or the small protein is or comprises IL-12, IL-15, IL-6, or IFN-γ.
74. The modified cell or the method of embodiment 8 or 69, wherein the therapeutic agent is regulated by Hif1a, NFAT, FOXP3, and/or NFkB.
75. The modified cell or the method of any one of embodiments 1-74, wherein the modified cell comprises a first targeting vector and a second targeting vector, the first targeting vector comprising a nucleic acid sequence encoding a CAR binding a blood antigen and the therapeutic agent, and the second targeting vector comprises a nucleic acid sequence encoding a CAR binding a solid tumor antigen and a dominant negative form of the immune checkpoint molecule.
76. The modified cell or the method of any one of embodiments 1-74, wherein the modified cell comprises a first targeting vector and a second targeting vector, the first targeting vector comprising a nucleic acid sequence encoding a CAR binding CD19 and the therapeutic agent, and the second targeting vector comprises a nucleic acid sequence encoding a CAR binding tMUC1 and a dominant negative form of PD-1.
77. The modified cell or the method of any one of embodiments 1-76, wherein the modified cell is derived form a healthy donor or the subject having the cancer.
78. The modified cell or the method of any one of embodiments 1-70, wherein the modified cell has a reduced expression of endogenous TRAC gene.

EXAMPLES

Example 1. CAR T Cells

Figure 9:
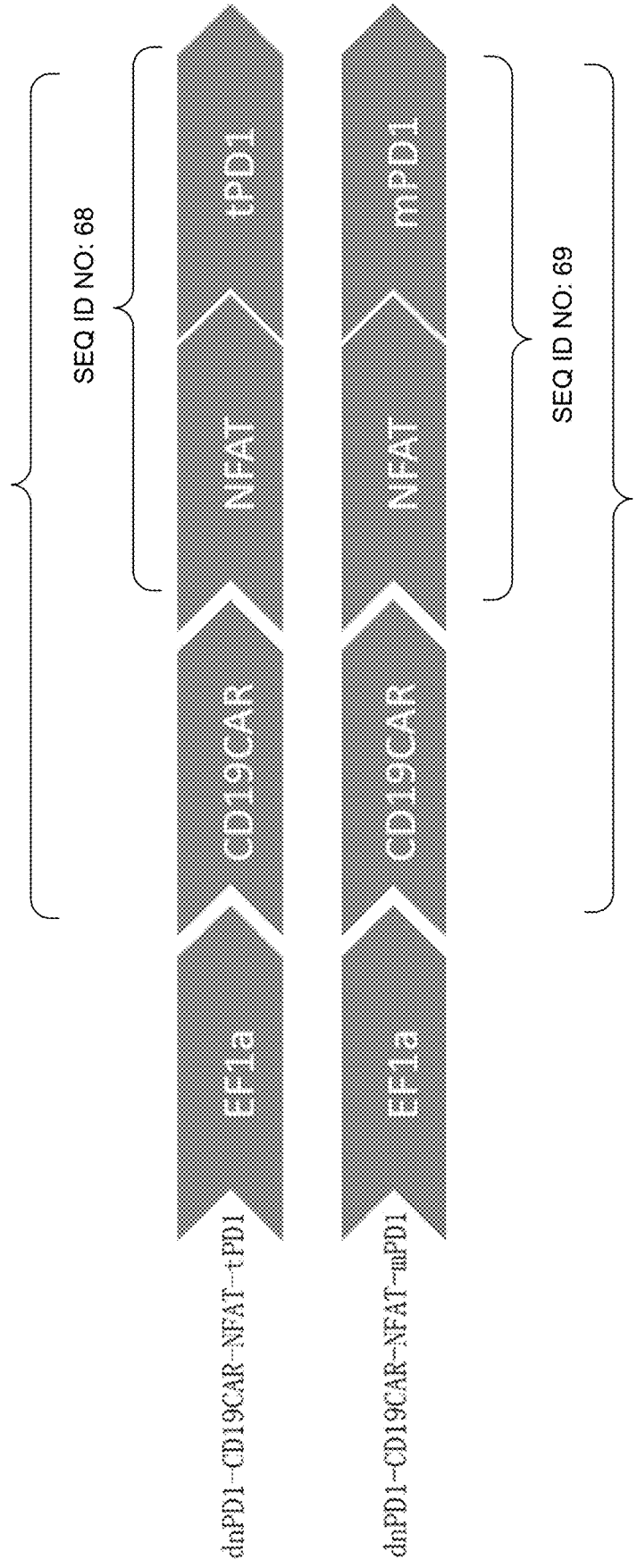
FIG. 9 shows exemplary vector structures.
Figure 10:
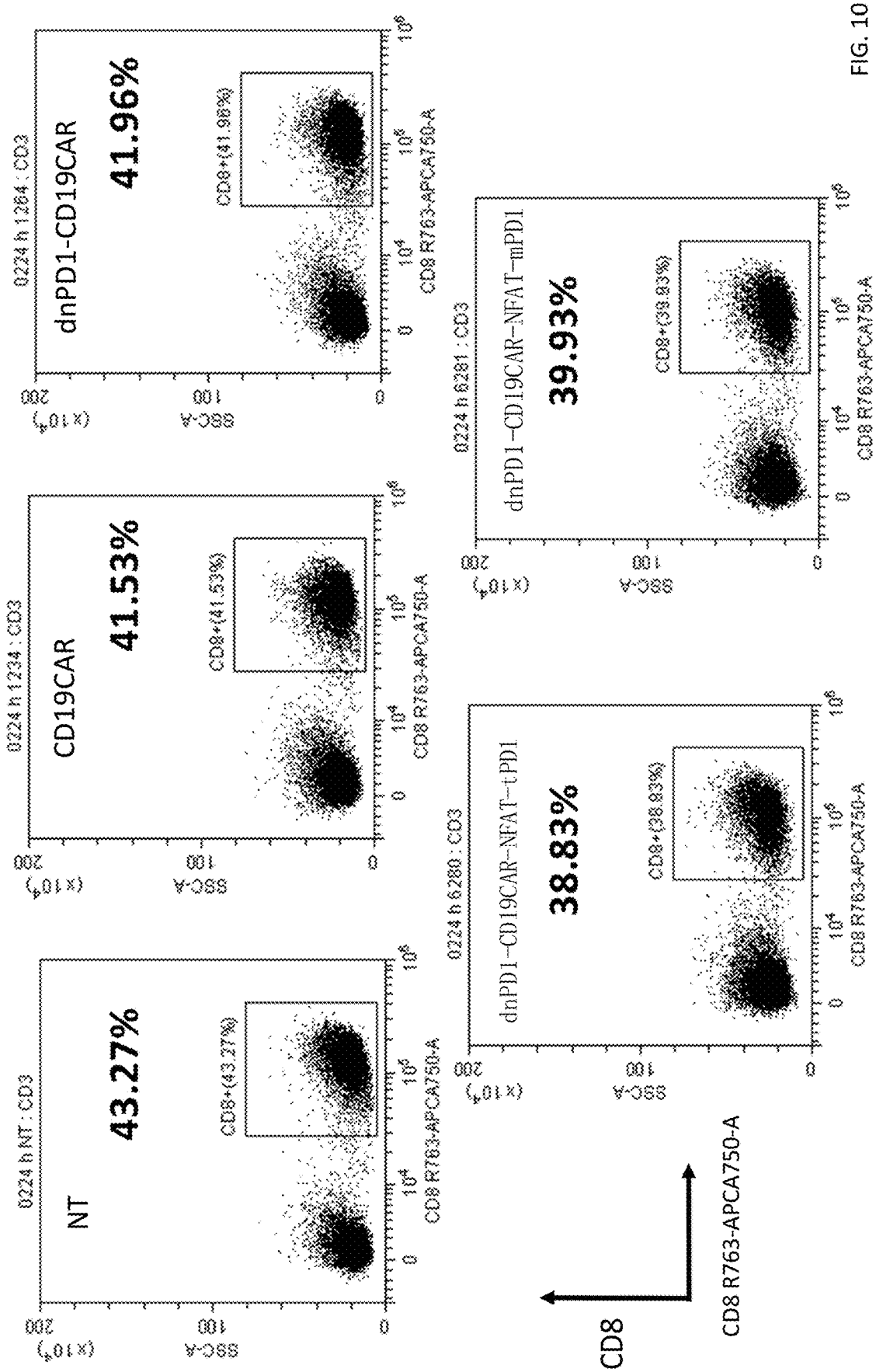
FIGS. 10, 11, and 12 show flow cytometry results of CAR T cells that have been cultured to Day 7.
Figure 11:
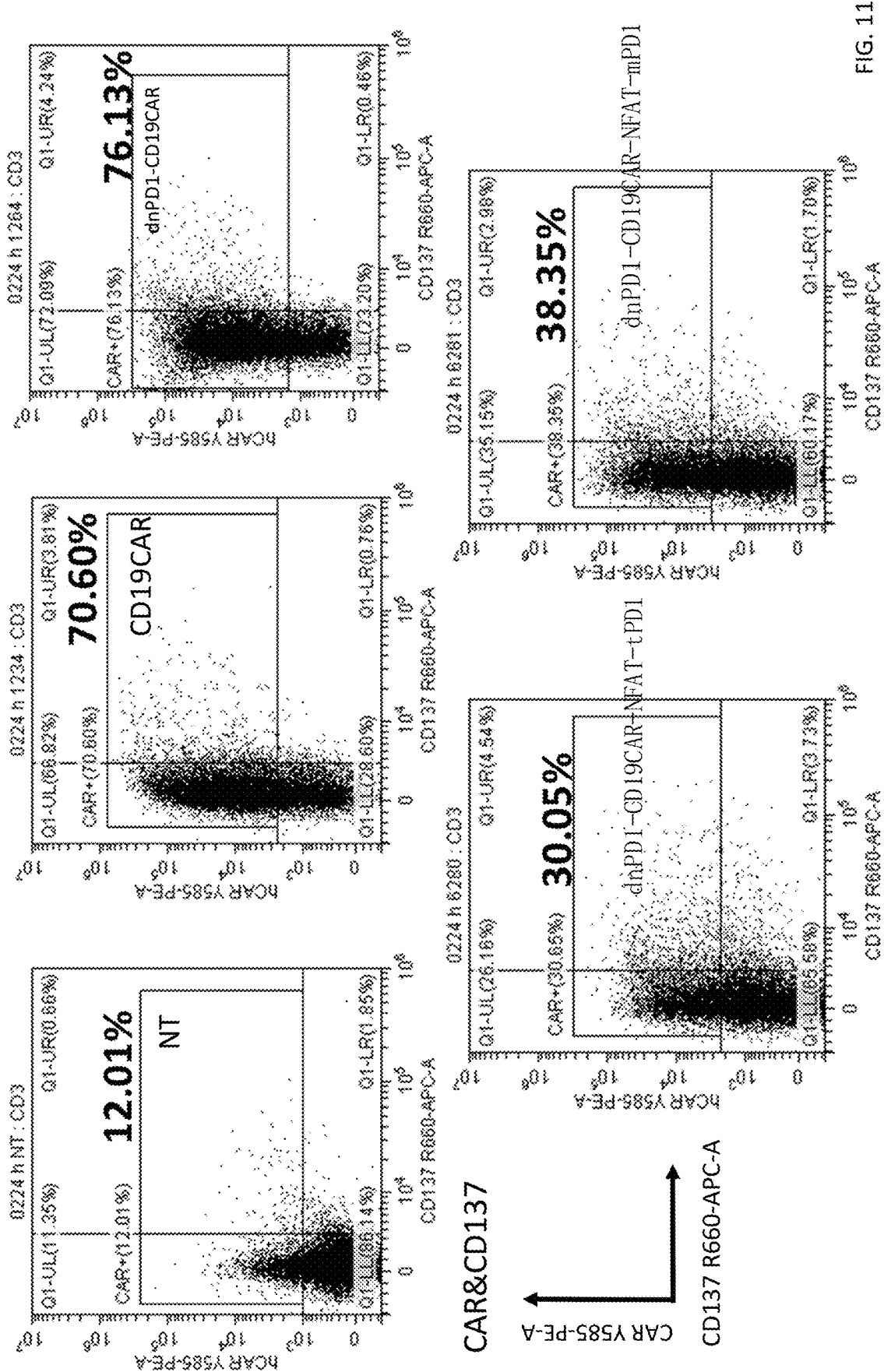
Figure 12:
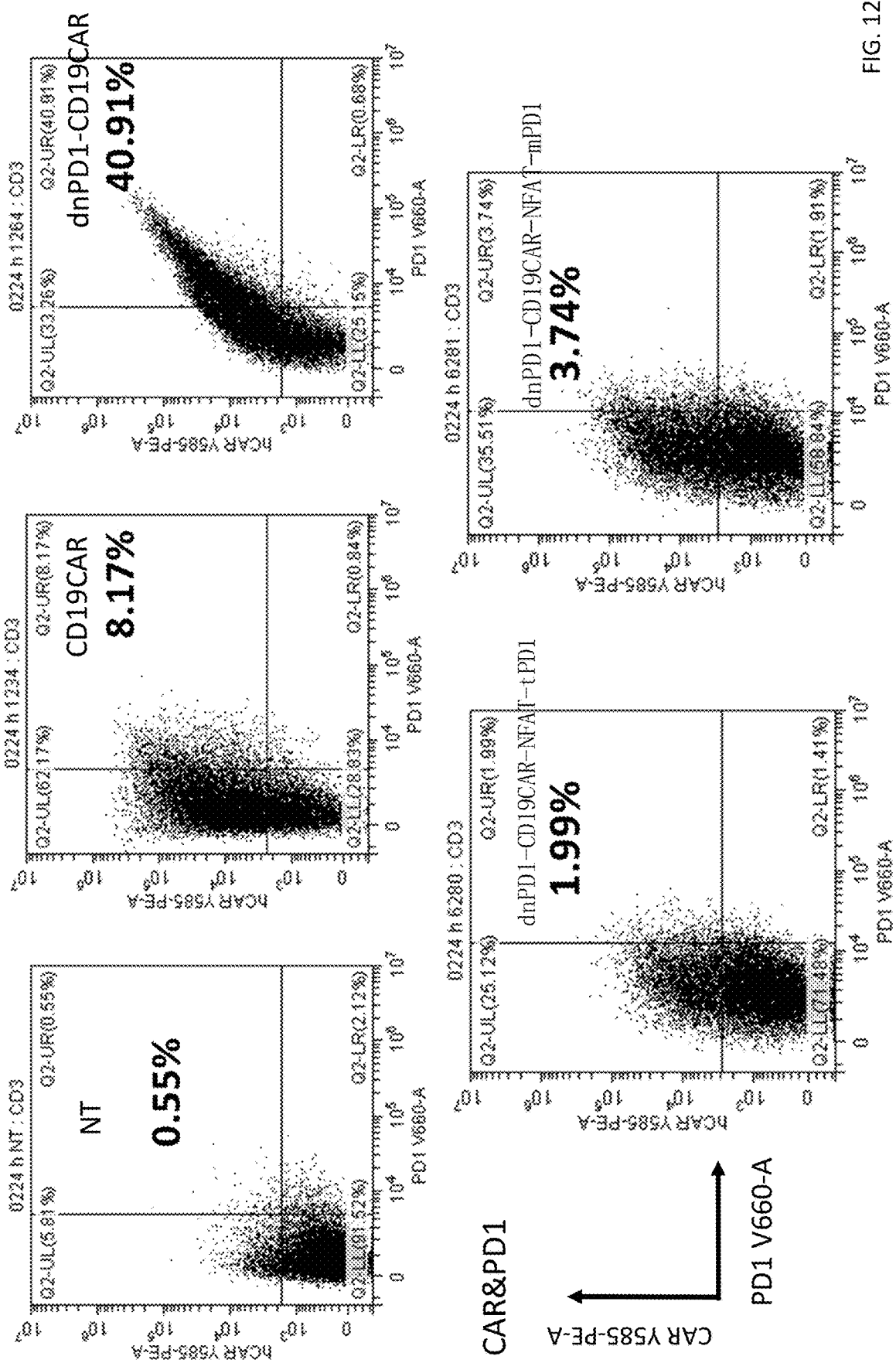

Lentiviral vectors that encode individual CAR molecules were generated and transfected into T cells, which are elaborated below. Techniques related to cell cultures, construction of cytotoxic T lymphocyte assay can be found in "Control of large, established tumor xenografts with genetically retargeted human T cells containing CD28 and CD137 domains," PNAS, Mar. 3, 2009, vol. 106 no. 9, 3360-3365 and "Chimeric Receptors Containing CD137 Signal Transduction Domains Mediate Enhanced Survival of T Cells and Increased Antileukemic Efficacy In Vivo," Molecular Therapy, August 2009, vol. 17 no. 8, 1453-1464, which are incorporated herein by reference in its entirety. FIG. 9 shows exemplary vector structures. FIGS. 10, 11, and 12 show flow cytometry results of CAR T cells that have been cultured to Day 7. On Day 7, CAR expressions were 70.60%, 76.13%, 30.05%, and 38.35%, respectively. Sequence information corresponding to various vectors in the Examples are provided in Table 7 and FIG. 9.

TABLE 7

| SEQ ID NO: | Identity |
| --- | --- |
| 1 | SP |
| 2 | Hinge & transmembrane domain |
| 3 | Co-stimulatory region |
| 4 | CD3-zeta |
| 5 | scFV Humanized CD19 |
| 6 | scFV CD19 |
| 7 | scFv FZD10 |
| 8 | scFv TSHR |
| 9 | scFv PRLR |
| 10 | scFv Muc 17 |
| 11 | scFv GUCY2C |
| 12 | scFv CD207 |
| 13 | Prolactin (ligand) |
| 14 | scFv CD3 |
| 15 | scFv CD4 |
| 16 | scFv CD4-2 |
| 17 | scFv CD5 |
| 18 | WTCD3zeta |
| 19 | WTCD3zeta-BCMACAR full length |
| 20 | BCMACAR |
| 21 | MUC1CAR |
| 22 | m19CAR-IRES-MUC1CAR |
| 23 | hCD19CAR-IRES-MUC1CAR |
| 24 | hCD22CAR-IRES-MUC1CAR |
| 25 | BCMACAR-IRES-MUC1CAR |
| 26 | mCD19CAR-2A-MUC1CAR |
| 27 | hCD19CAR-2A-MUC1CAR |
| 28 | hCD22CAR-2A-MUC1CAR |
| 29 | BCMA-2A-MUC1CAR |
| 30 | Tumor associated MUC1 scFv 1 |
| 31 | Tumor associated MUC1 scFv-1 VH |
| 32 | Tumor associated MUC1 scFv-1 VL |
| 33 | Tumor associated MUC1 scFv 2 |
| 34 | Tumor associated MUC1 scFv2 VH |
| 35 | Tumor associated MUC1 scFv2 VL |
| 36 | Modified PD-1 intracellular domain −1 |

TABLE 7-continued

| SEQ ID NO: | Identity |
|---|---|
|  | (two tyrosine kinase mutations) |
| 37 | Modified PD-1 of SEQ ID NO: 36 (extracellular, transmembrane, and intracellular domains) |
| 38 | Modified PD-1 intracellular domain −2 |
| 39 | Modified PD-1 intracellular domain −3 |
| 40 | Modified PD-1 intracellular domain −4 |
| 41 | Modified PD-1 intracellular domain −5 |
| 42 | Removed PD-1 intracellular domain −2 |
| 43 | A hinge |
| 44 | Seq1: WT |
| 45 | Seq2: Y201F |
| 46 | Seq3: Y218F |
| 47 | Seq4: Y201F Y218F |
| 48 | Seq5: Truncated (delete internal 190-223) |
| 49 | Seq6: Replace with CD8 transmembrane (delete 161-223, add CD8 transmembrane) |
| 50 | Seq7: L141A Y201F Y218F |
| 51 | Seq8: Truncated (delete internal 190-223) + L141A |
| 52 | Seq9: Replace with CD8 transmembrane + L141A |
| 53 | WT CD3 zeta aa |
| 45 | Modified PD-1 (WT) |
| 55 | Modified PD-1 (Point mutation 1) |
| 56 | Modified PD-1 (point mutations 2 sites-2) |
| 57 | Modified PD-1 (point mutations 2 sites-3) |
| 58 | PD-1-soluble |
| 59 | PD-1-CD28 |
| 60 | ef1a1 |
| 61 | Rtta |
| 62 | TRE |
| 63 | ef1a2 |
| 64 | scFv against PD-1 |
| 65 | scFv against PD-L1 |
| 66 | Singlec15 antigen |
| 67 | NFAT promoter sequence |
| 68 | NFAT promoter-T-PD-1 sequence |
| 69 | NFAT promoter-M-PD-1 sequence |
| 70 | CD19CAR + NFAT promoter + M-PD-1 sequence |
| 71 | CD19CAR + NFAT promoter + M-PD-1 sequence |

Example 2. CAR T Cells Challenged by Tumor Cells

Figure 13:
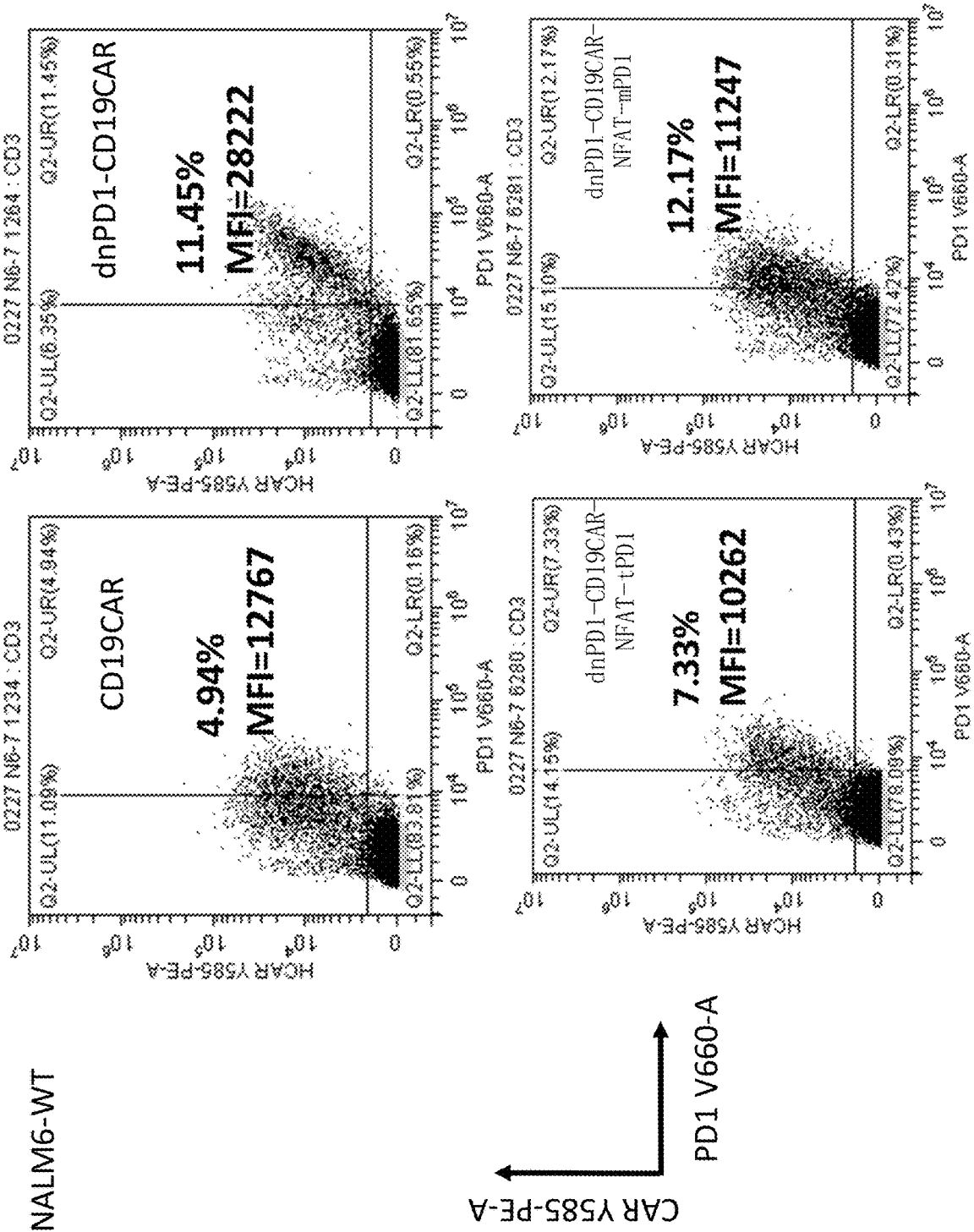
FIGS. 13 and 14 show flow cytometry results of co-culturing CAR T cells and corresponding tumor cells.
Figure 14:
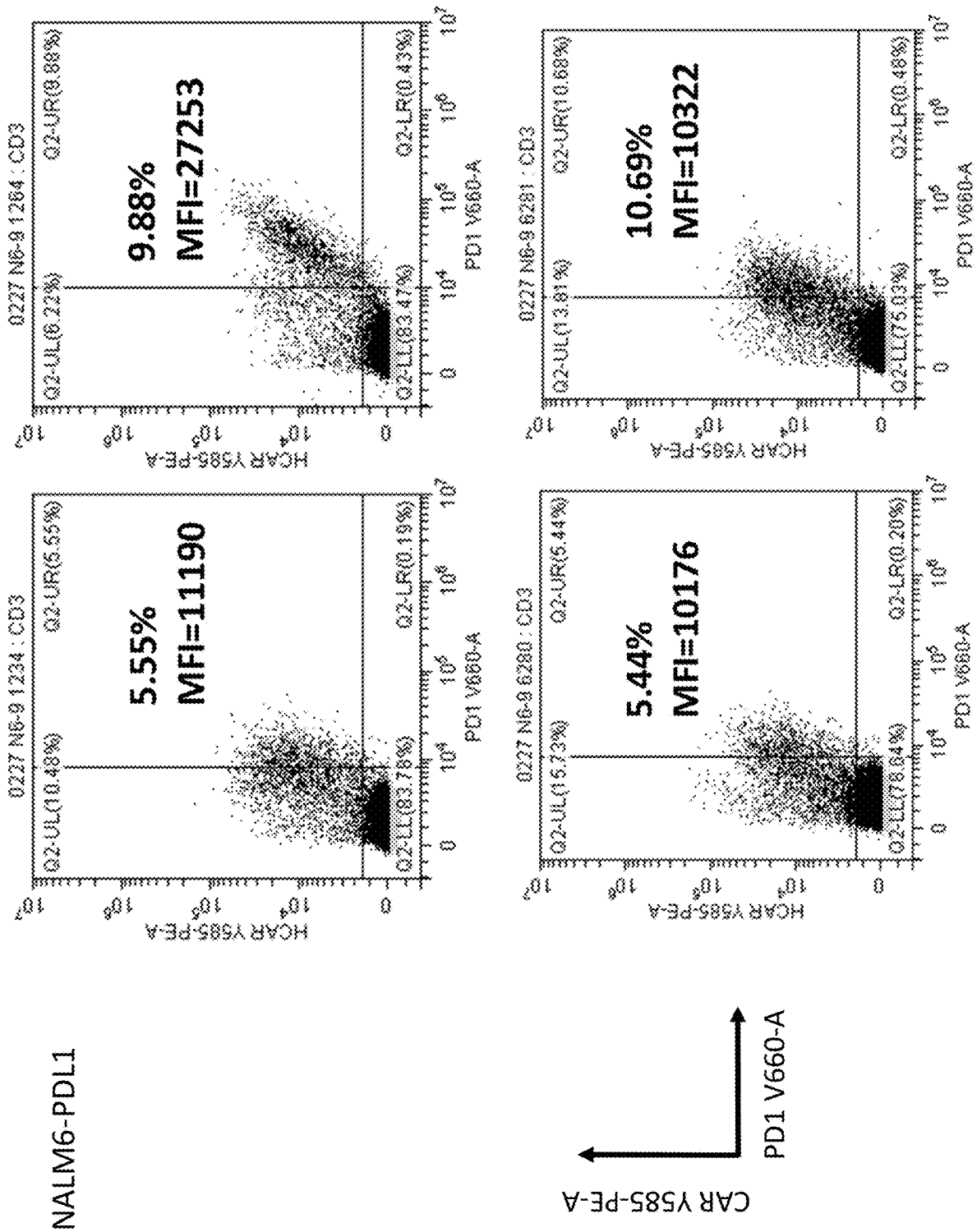
Figure 15:
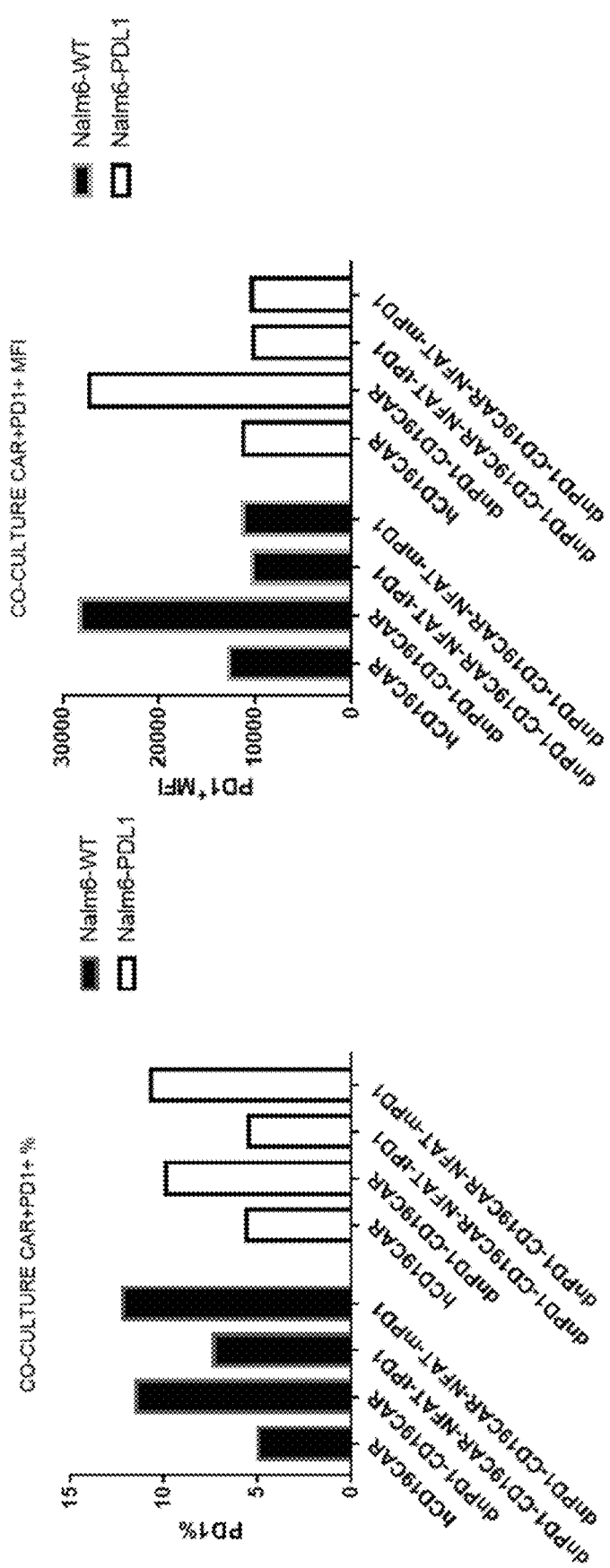
FIG. 15 shows charts corresponding to the flow cytometry results shown in FIGS. 13 and 14.

FIGS. 13 and 14 show flow cytometry results of the co-culturing of CAR T and the corresponding tumor cells. FIG. 15 shows graphs corresponding to the flow cytometry results shown in FIGS. 13 and 14. The co-culture of CAR T cells and the corresponding tumor cells started on Day 7, and CAR expression rates were adjusted to be consistent with NT (Non-transduced) during the co-culture. The CAR expression of all four CAR T cells was adjusted to 30.05%. After CAR expression was adjusted, the ratio of T cells and tumor cells was set to 3:1 (tumor cells include N6LM6-WT (CD19+) and NALM6-PD-L1 (CD19+PD-L1+)). T cells and tumor cells were added to the same culture well according to the above ratio. After co-culturing for 24 hours, the expression and phenotype of the cells were detected. After co-culturing with CD19+ tumor for 24 hours, both, PD-1 and hCD19CAR, and NFAT promoter-PD-1-CAR and 2a-dnPD-1CAR, were expressed. The stimulation of the two tumor cells did not significantly differ for CAR T cells.

Example 3. Expression of Exogenous PD-1

Figure 16:
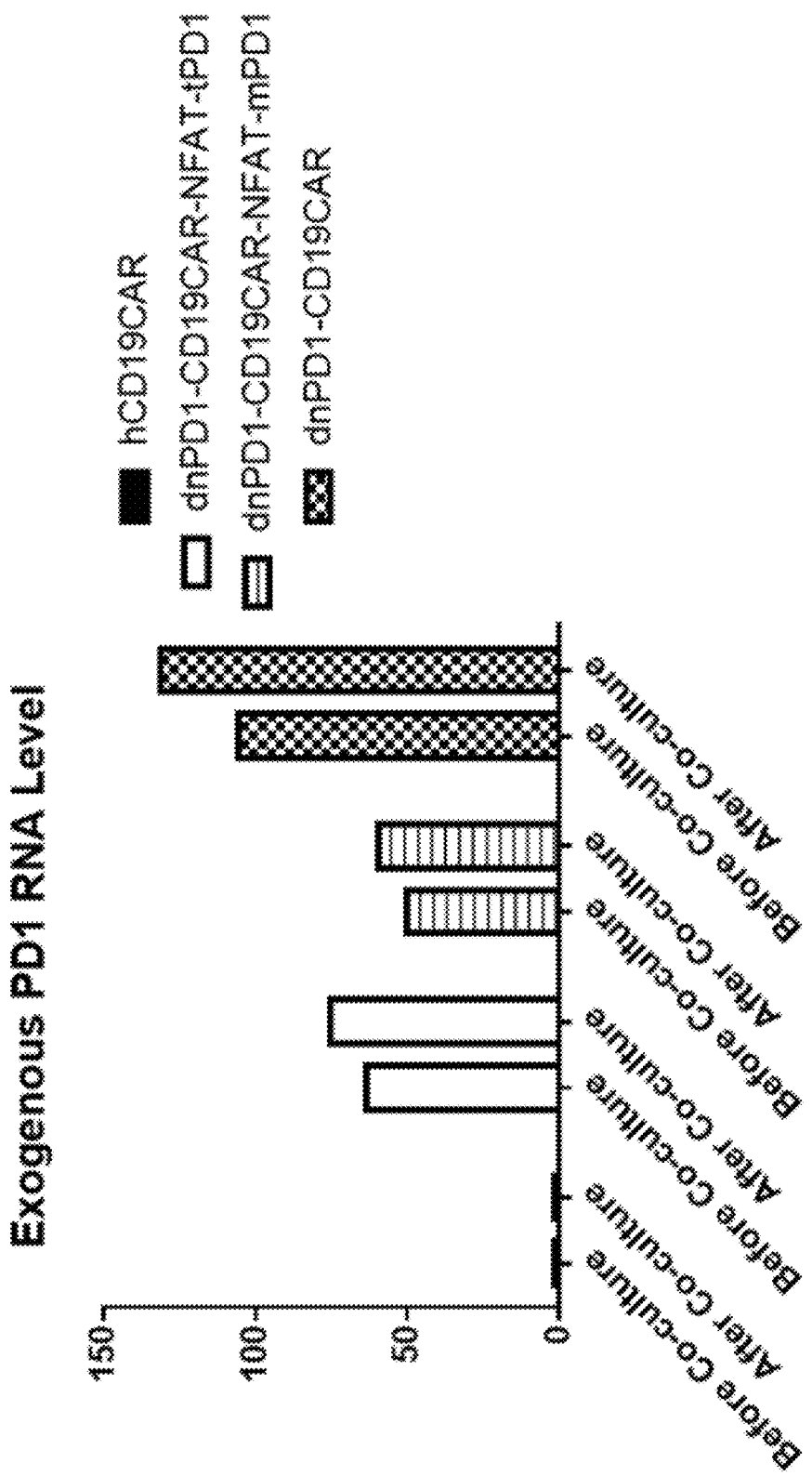
FIG. 16 shows the expression of exogenous PD-1 RNA in T cells.
Figure 17:
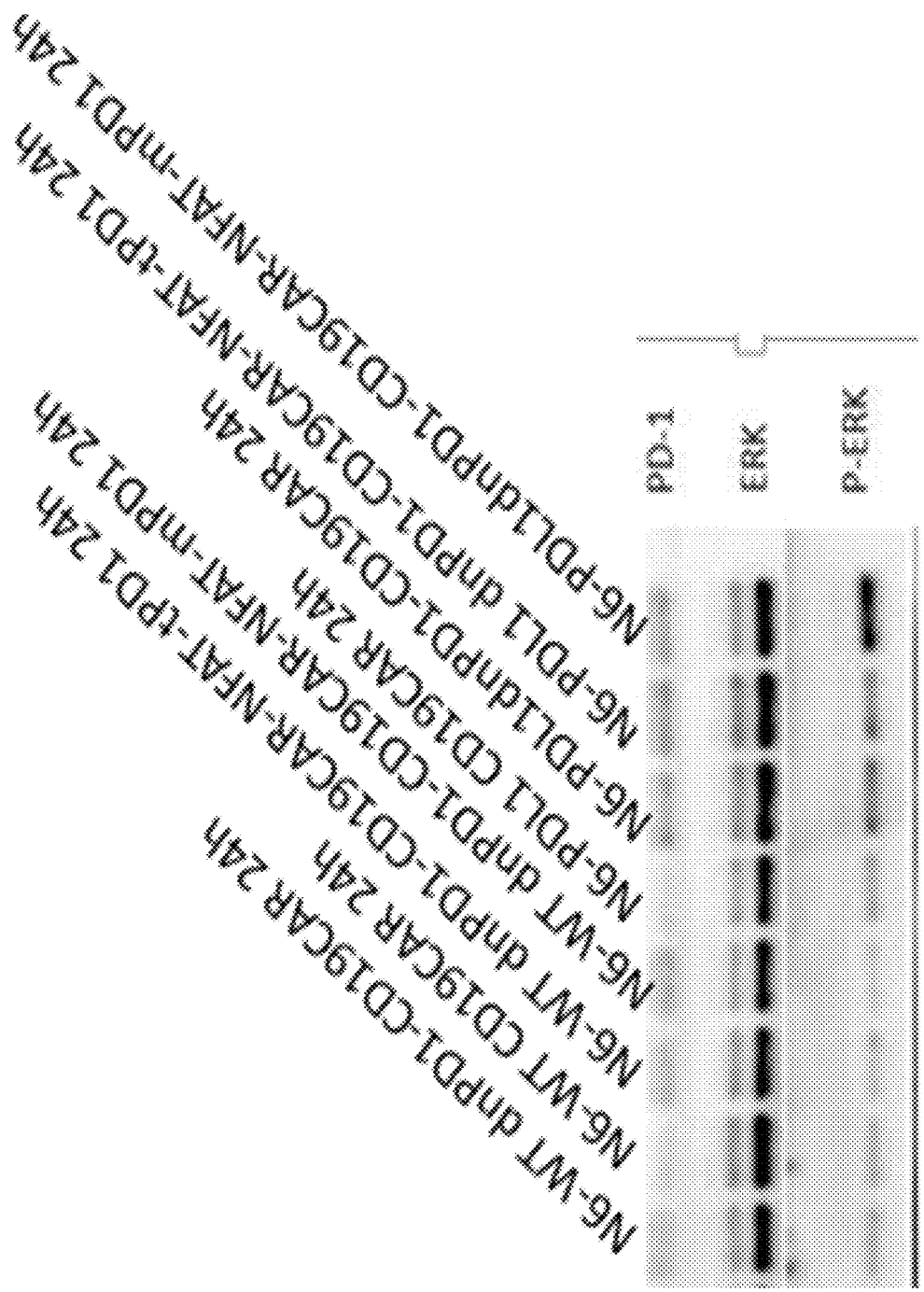
FIG. 17 shows the expression of exogenous PD-1 Western Blot in T cells.
Figure 18:
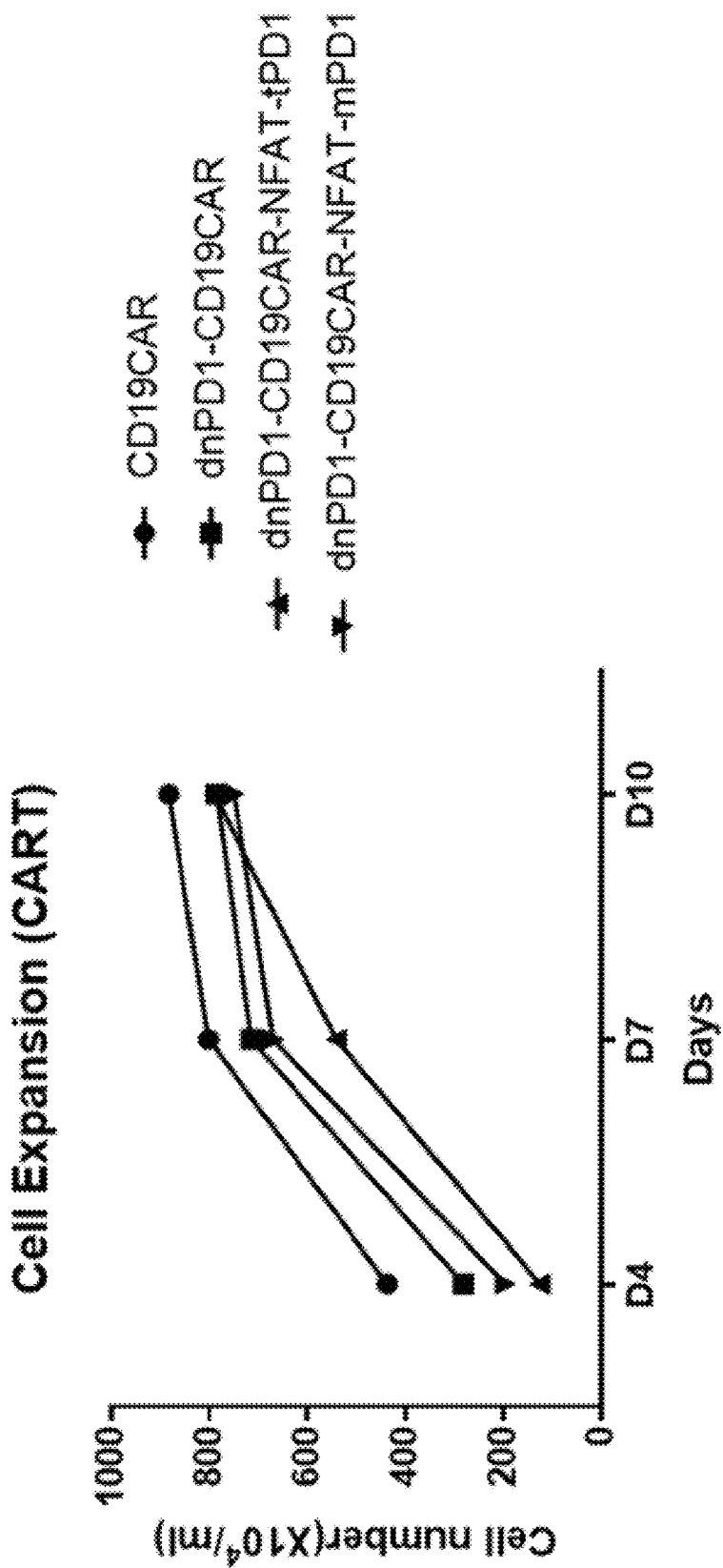
FIG. 18 shows cell expansion of various CAR T cells.

FIG. 16 shows the expression of exogenous PD1 RNA in T cells. FIG. 17 shows the expression of exogenous PD-1 Western Blot in T cells. After co-culturing CAR T cells and tumor cells for 24 hours (hrs), the expression of exogenous PD-1 was detected. Based on the RNA level measured, FIG. 17 showed that the PD-1 expression of CD19CAR was always at a low level. Exogenous PD-1 was expressed before and after the co-culture of NFAT promoter-PD-1-CAR T cells and the tumor cells, and there was an increase after the co-culture. These results showed that NFAT promoter driven dnPD-1 (NFAT promoter-dnPD-1) was expressed at the RNA level but the expression was weaker than the consistent expression of dnPD-1 (2A-dnPD-1). In Western-Blot results shown in FIG. 17, dnPD-1 was significantly up-regulated 24 hrs after co-culture with CD19+ tumor cells. The phosphorylation level of Erk of 2A-dnPD-1 was higher than that of NFAT promoter-dnPD-1 in response to PD-L1+ tumor cells. FIG. 18 shows cell expansion of various CAR T cells. Comprehensive calculation of the cell count results and the CAR expression after flow cytometry was conducted. The expansion of CAR T cells containing dnPD-1 CAR T cells was similar to that of traditional CD19CAR T cells.

Example 4. Killing Assay on CAR T Cells

Figure 19:
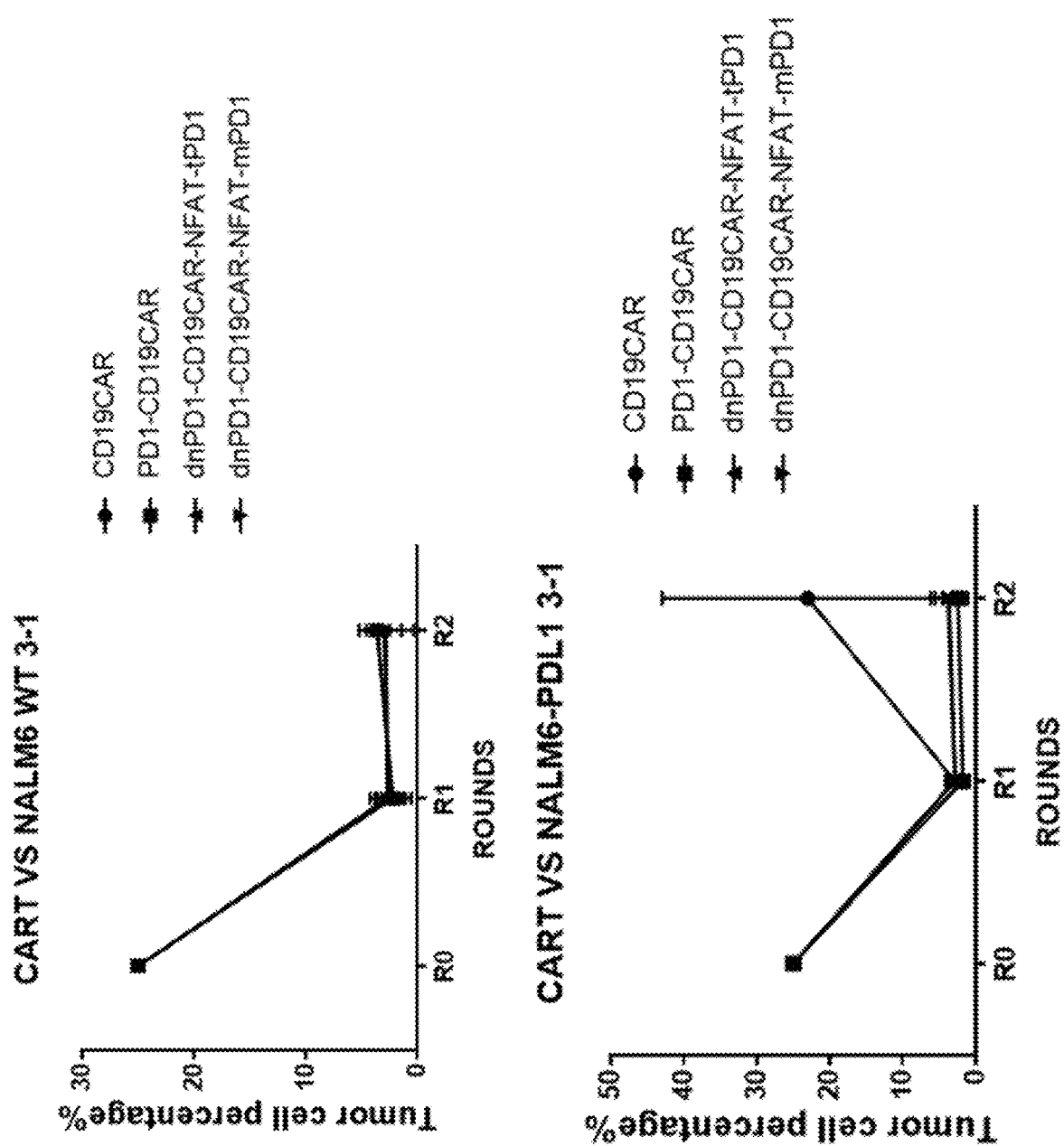
FIG. 19 shows killing assay results of CAR T cells challenged by several rounds of tumor cells.

FIG. 19 shows killing assay results of CAR T cells challenged by several rounds of tumor cells. The initial ratio of CAR T cells to tumor cells was 3:1. After killing, the ratio of tumor cells decreased. Then, tumor cells were added to the co-culture system again, and the ratio of CAR T cells to tumor cells returned to 3:1. After multiple rounds, it was observed that the killing of various CAR T cells was similar when the tumor did not express PD-L1. After tumor cells expressing PD-L1 were added, the killing of CD19 CAR T cells was similar to the other groups at the beginning. By round R2, various dnPD-1-CD19CAR T cells showed better killing functions as compared to CD19CAR T cells that does not express dnPD-1.

The invention claimed is:

1. A modified cell comprising a binding molecule, and a dominant negative form of an inhibitory immune checkpoint molecule, wherein expression of the dominant negative form of the inhibitory immune checkpoint molecule is regulated by an inducible gene expression system, wherein the modified cell comprises a polynucleotide comprising at least one of SEQ ID NOs: 68-71.

2. The modified cell of claim 1, wherein the polynucleotide encoding the binding molecule and the dominant negative form of the inhibitory immune checkpoint molecule, wherein expression of the dominant negative form of the inhibitory immune checkpoint molecule is regulated by an inducible gene expression system.

3. The modified cell of claim 1, wherein the binding molecule is a modified T cell receptor (TCR) or a chimeric antigen receptor (CAR).

4. The modified cell of claim 3, wherein the TCR is obtained from spontaneously occurring tumor-specific T cells in patients, and wherein the TCR binds to a tumor antigen that comprises CEA, gp100, MART-1, p53, MAGE-A3, or NY-ESO-1, or the TCR comprises TCRγ and TORδ chains or TCRα and TCRβ chains, or a combination thereof.

5. The modified cell of claim 3, wherein the CAR comprises an antigen binding domain, a transmembrane domain, and an intracellular domain.

6. The modified cell of claim 5, wherein the antigen binding domain binds to a tumor antigen comprising TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, Lewis Y, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, GM3, TGS5, HMWMAA, o-acetyl-GD2, Folate receptor beta, TEM1/CD248, TEM7R, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin, telomerase, PCTA-1 (Galectin 8), MelanA (MART1), Ras mutant, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase (hTERT), RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, GUCY2C, or IGLL1.

7. The modified cell of claim 5, wherein the intracellular domain comprises a co-stimulatory signaling domain, or a primary signaling domain and a co-stimulatory signaling domain, wherein the co-stimulatory signaling domain comprises a signaling domain of a protein comprising CD27, CD28, 4-1 BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11 b, ITGAX, CD11c, ITGB1, CD29, ITGB2, CD18, LFA-1, ITGB7, TNFR2, TRANCE (RANKL), DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

8. The modified cell of claim 3, wherein the modified cell is a T cell or an NK cell.

9. The modified cell of claim 1, wherein the modified cell is engineered to express and secrete a therapeutic agent.

10. The modified cell of claim 9, wherein the therapeutic agent comprises IL-12, IL-6, or IFN-γ.

11. A polynucleotide comprising SEQ ID NO: 68, 69, 70, or 71.

* * * * *

SEQUENCE LISTING

```
<160> NUMBER OF SEQ ID NOS: 71

<210> SEQ ID NO 1
<211> LENGTH: 21
<212> TYPE: PRT
<213> ORGANISM: Artificial Sequence
<220> FEATURE:
<223> OTHER INFORMATION: Synthesized

<400> SEQUENCE: 1

Met Ala Leu Pro Val Thr Ala Leu Leu Leu Pro Leu Ala Leu Leu Leu
```

His Ala Ala Arg Pro
            20

<210> SEQ ID NO 2
<211> LENGTH: 69
<212> TYPE: PRT
<213> ORGANISM: Artificial Sequence
<220> FEATURE:
<223> OTHER INFORMATION: Synthesized

<400> SEQUENCE: 2

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65

<210> SEQ ID NO 3
<211> LENGTH: 42
<212> TYPE: PRT
<213> ORGANISM: Artificial Sequence
<220> FEATURE:
<223> OTHER INFORMATION: Synthesized

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 5
<211> LENGTH: 242
<212> TYPE: PRT
<213> ORGANISM: Artificial Sequence
<220> FEATURE:
<223> OTHER INFORMATION: Synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
            165                 170                 175

Glu Thr Thr Tyr Tyr Asn Ser Ala Leu Lys Ser Arg Phe Thr Ile Ser
            180                 185                 190

Arg Asp Asn Ala Lys Asn Ser Leu Tyr Leu Gln Met Asn Ser Leu Arg
        195                 200                 205

Ala Glu Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 6
<211> LENGTH: 242
<212> TYPE: PRT
<213> ORGANISM: Artificial Sequence
<220> FEATURE:
<223> OTHER INFORMATION: Synthesized

<400> SEQUENCE: 6

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60
```

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
                195                 200                 205

Thr Asp Asp Thr Ala Ile Tyr Tyr Cys Ala Lys His Tyr Tyr Tyr Gly
            210                 215                 220

Gly Ser Tyr Ala Met Asp Tyr Trp Gly Gln Gly Thr Ser Val Thr Val
225                 230                 235                 240

Ser Ser

<210> SEQ ID NO 7
<211> LENGTH: 237
<212> TYPE: PRT
<213> ORGANISM: Artificial Sequence
<220> FEATURE:
<223> OTHER INFORMATION: Synthesized

<400> SEQUENCE: 7

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Gly Gly Gly Ser Gly Gly Gly
            100                 105                 110

Gly Ser Gly Gly Gly Gly Ser Glu Val Gln Leu Gln Gln Ser Gly Ala
            115                 120                 125

Glu Leu Val Lys Pro Gly Ala Ser Val Lys Leu Ser Cys Thr Ala Ser
130                 135                 140

Gly Phe Asn Ile Asn Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

```
Thr Lys Tyr Asp Pro Lys Phe Gln Gly Lys Ala Thr Ile Thr Ala Asp
            180                 185                 190

Thr Ser Ser Asn Thr Ala Tyr Leu Gln Leu Ser Ser Leu Thr Ser Glu
            195                 200                 205

Asp Thr Ala Val Tyr Tyr Cys Ala Arg Gly Ala Arg Gly Ser Arg Phe
            210                 215                 220

Ala Tyr Trp Gly Gln Gly Thr Leu Val Thr Val Ser Ala
225                 230                 235

<210> SEQ ID NO 8
<211> LENGTH: 244
<212> TYPE: PRT
<213> ORGANISM: Artificial Sequence
<220> FEATURE:
<223> OTHER INFORMATION: Synthesized

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
            35                  40                  45

Ile Tyr Asp Asn Asn Lys Arg Pro Ser Ala Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Gly Ser Gly Gly Gly Gly Ser Glu Val Gln
            115                 120                 125

Leu Val Gln Ser Gly Ala Glu Val Lys Lys Pro Gly Gln Ser Leu Lys
130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
            195                 200                 205

Ser Ser Leu Lys Ala Ser Asp Thr Ala Ile Tyr Tyr Cys Val Gly Leu
            210                 215                 220

Asp Trp Asn Tyr Asn Pro Leu Arg Tyr Trp Gly Pro Gly Thr Leu Val
225                 230                 235                 240

Thr Val Ser Ser

<210> SEQ ID NO 9
<211> LENGTH: 252
<212> TYPE: PRT
<213> ORGANISM: Artificial Sequence
<220> FEATURE:
<223> OTHER INFORMATION: Synthesized

<400> SEQUENCE: 9
```

```
Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Asp Ala Ala Thr Tyr Tyr Cys Gln His Ser Gly
                85                  90                  95

Glu Leu Pro Pro Ser Phe Gly Gly Thr Lys Leu Glu Ile Lys Arg
            100                 105                 110

Ala Gly Gly Gly Gly Ser Gly Gly Gly Gly Ser Gly Gly Gly Gly Ser
            115                 120                 125

Glu Val Gln Leu Val Glu Ser Gly Gly Asp Leu Val Lys Pro Gly Gly
            130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
                180                 185                 190

Lys Gly Arg Phe Thr Ile Ser Arg Asp Asn Ala Lys Asn Thr Leu Tyr
                195                 200                 205

Leu Gln Met Ser Ser Leu Lys Ser Glu Asp Ser Ala Met Tyr Tyr Cys
    210                 215                 220

Ala Arg His Arg Gly Asn Tyr Tyr Ala Thr Tyr Tyr Ala Met Asp
225                 230                 235                 240

Tyr Trp Gly Gln Gly Thr Ser Val Thr Val Ser Ser
                245                 250

<210> SEQ ID NO 10
<211> LENGTH: 243
<212> TYPE: PRT
<213> ORGANISM: Artificial Sequence
<220> FEATURE:
<223> OTHER INFORMATION: Synthesized

<400> SEQUENCE: 10

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Glu Tyr Pro Tyr
                85                  90                  95

Thr Phe Gly Gly Gly Thr Lys Leu Glu Ile Lys Gly Gly Gly Gly Ser
            100                 105                 110
```

```
Gly Gly Gly Gly Ser Gly Gly Gly Ser Gln Val Gln Leu Gln Gln
            115                 120                 125

Pro Gly Ala Glu Leu Val Arg Pro Gly Ala Ser Val Lys Leu Ser Cys
130                 135                 140

Lys Ala Ser Gly Tyr Thr Phe Thr Thr Tyr Trp Met Asn Trp Val Lys
145                 150                 155                 160

Gln Arg Pro Glu Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
                180                 185                 190

Thr Val Asp Lys Ser Ser Ser Thr Ala Tyr Met Gln Leu Ser Ser Leu
                195                 200                 205

Thr Ser Glu Asp Ser Ala Val Tyr Tyr Cys Ala Arg Gly Pro Tyr Tyr
            210                 215                 220

Gly Thr Asn Pro Trp Phe Pro Tyr Trp Gly Gln Gly Thr Leu Val Thr
225                 230                 235                 240

Val Ser Ser

<210> SEQ ID NO 11
<211> LENGTH: 241
<212> TYPE: PRT
<213> ORGANISM: Artificial Sequence
<220> FEATURE:
<223> OTHER INFORMATION: Synthesized

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
            115                 120                 125

Trp Gly Ala Gly Leu Leu Lys Pro Ser Glu Thr Leu Ser Leu Thr Cys
130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
                180                 185                 190

Val Asp Thr Ser Lys Asn Gln Phe Ala Leu Lys Leu Ser Ser Val Thr
                195                 200                 205

Ala Ala Asp Thr Ala Val Tyr Tyr Cys Ala Arg Glu Arg Gly Tyr Thr
            210                 215                 220

Tyr Gly Asn Phe Asp His Trp Gly Gln Gly Thr Leu Val Thr Val Ser
```

Ser

```
<210> SEQ ID NO 12
<211> LENGTH: 246
<212> TYPE: PRT
<213> ORGANISM: Artificial Sequence
<220> FEATURE:
<223> OTHER INFORMATION: Synthesized

<400> SEQUENCE: 12
```

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Ser Gly Gly Gly Gly
        115                 120                 125

Ser Gln Val Gln Leu Arg Gln Ser Gly Pro Glu Leu Val Lys Pro Gly
    130                 135                 140

Ala Ser Val Lys Met Ser Cys Lys Ala Ser Gly Tyr Thr Phe Thr Asp
145                 150                 155                 160

Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
            245

```
<210> SEQ ID NO 13
<211> LENGTH: 199
<212> TYPE: PRT
<213> ORGANISM: Artificial Sequence
<220> FEATURE:
<223> OTHER INFORMATION: Synthesized

<400> SEQUENCE: 13
```

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg

```
                35                  40                  45
Gly Phe Ile Thr Lys Ala Ile Asn Ser Cys His Thr Ser Ser Leu Ala
 50                  55                  60
Thr Pro Glu Asp Lys Glu Gln Ala Gln Gln Met Asn Gln Lys Asp Phe
 65                  70                  75                  80
Leu Ser Leu Ile Val Ser Ile Leu Arg Ser Trp Asn Glu Pro Leu Tyr
                 85                  90                  95
His Leu Val Thr Glu Val Arg Gly Met Gln Glu Ala Pro Glu Ala Ile
                100                 105                 110
Leu Ser Lys Ala Val Glu Ile Glu Gln Thr Lys Arg Leu Leu Glu
                115                 120                 125
Gly Met Glu Leu Ile Val Ser Gln Val His Pro Glu Thr Lys Glu Asn
130                 135                 140
Glu Ile Tyr Pro Val Trp Ser Gly Leu Pro Ser Leu Gln Met Ala Asp
145                 150                 155                 160
Glu Glu Ser Arg Leu Ser Ala Tyr Tyr Asn Leu Leu His Cys Leu Arg
                165                 170                 175
Arg Asp Ser His Lys Ile Asp Asn Tyr Leu Lys Leu Lys Cys Arg
                180                 185                 190
Ile Ile His Asn Asn Asn Cys
                195

<210> SEQ ID NO 14
<211> LENGTH: 240
<212> TYPE: PRT
<213> ORGANISM: Artificial Sequence
<220> FEATURE:
<223> OTHER INFORMATION: Synthesized

<400> SEQUENCE: 14

Asp Ile Val Met Thr Gln Ser Pro Asp Ser Leu Ala Val Ser Leu Gly
  1               5                  10                  15
Glu Arg Ala Thr Ile Asn Cys Lys Ser Ser Gln Ser Leu Leu Asn Ser
                 20                  25                  30
Arg Thr Arg Lys Asn Tyr Leu Ala Trp Tyr Gln Gln Lys Pro Gly Gln
                 35                  40                  45
Pro Pro Lys Leu Leu Ile Tyr Trp Ala Ser Thr Arg Glu Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Thr Gln
                 85                  90                  95
Ser Phe Ile Leu Arg Thr Phe Gly Gln Gly Thr Lys Val Glu Ile Lys
                100                 105                 110
Gly Gly Gly Gly Ser Gly Gly Gly Gly Ser Gly Gly Gly Gly Ser
                115                 120                 125
Asp Ile Val Met Thr Gln Ser Pro Asp Ser Leu Ala Val Ser Leu Gly
                130                 135                 140
Glu Arg Ala Thr Ile Asn Cys Lys Ser Ser Gln Ser Leu Leu Asn Ser
145                 150                 155                 160
Arg Thr Arg Lys Asn Tyr Leu Ala Trp Tyr Gln Gln Lys Pro Gly Gln
                165                 170                 175
Pro Pro Lys Leu Leu Ile Tyr Trp Ala Ser Thr Arg Glu Ser Gly Val
                180                 185                 190
Pro Asp Arg Phe Ser Gly Ser Gly Ser Gly Thr Asp Phe Thr Leu Thr
```

```
            195                 200                 205
Ile Ser Ser Leu Gln Ala Glu Asp Val Ala Val Tyr Tyr Cys Thr Gln
210                 215                 220

Ser Phe Ile Leu Arg Thr Phe Gly Gln Gly Thr Lys Val Glu Ile Lys
225                 230                 235                 240

<210> SEQ ID NO 15
<211> LENGTH: 281
<212> TYPE: PRT
<213> ORGANISM: Artificial Sequence
<220> FEATURE:
<223> OTHER INFORMATION: Synthesized

<400> SEQUENCE: 15

Met Asn Val Pro Thr Gln Leu Leu Gly Leu Leu Leu Trp Leu Thr
1               5                   10                  15

Gly Gly Lys Cys Asp Ile Gln Met Thr Gln Ser Pro Ala Ser Leu Ser
                20                  25                  30

Ala Ser Leu Glu Glu Ile Val Thr Ile Thr Cys Lys Ala Ser Gln Ala
            35                  40                  45

Ile Asp Ala Tyr Leu Ser Trp Tyr Gln Gln Lys Pro Gly Lys Ser Pro
50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys Gly
        115                 120                 125

Gly Gly Gly Gly Ser Gly Gly Gly Ser Gly Gly Gly Ser Met
130                 135                 140

Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
            180                 185                 190

Ser Asn Ser Val Ser Trp Ile Arg Gln Pro Pro Gly Lys Gly Leu Glu
        195                 200                 205

Trp Met Gly Val Ile Trp Ser Asn Gly Asp Ala Asp Tyr Asn Ser Ala
210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255

Cys Ala Ser Pro Tyr Tyr Gly Tyr Tyr Phe Pro Phe Tyr Trp Gly
            260                 265                 270

Gln Gly Val Met Val Thr Val Ser Ser
        275                 280

<210> SEQ ID NO 16
<211> LENGTH: 285
<212> TYPE: PRT
<213> ORGANISM: Artificial Sequence
<220> FEATURE:
<223> OTHER INFORMATION: Synthesized
```

<400> SEQUENCE: 16

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Asp Pro Tyr Thr Phe Gly Ala Gly Thr Lys Leu Glu
        115                 120                 125

Leu Lys Gly Gly Gly Gly Ser Gly Gly Gly Ser Gly Gly Gly
    130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
    210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
        275                 280                 285

<210> SEQ ID NO 17
<211> LENGTH: 242
<212> TYPE: PRT
<213> ORGANISM: Artificial Sequence
<220> FEATURE:
<223> OTHER INFORMATION: Synthesized

<400> SEQUENCE: 17

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
    50                  55                  60

```
Ser Gly Ser Gly Thr Asp Phe Thr Leu Thr Ile Ser Ser Leu Gln Pro
 65                  70                  75                  80

Glu Asp Ile Ala Thr Tyr Phe Cys His Gln Tyr Asn Ser Tyr Asn Thr
                 85                  90                  95

Phe Gly Ser Gly Thr Lys Leu Glu Ile Lys Gly Gly Gly Gly Ser
            100                 105                 110

Gly Gly Gly Gly Ser Gly Gly Gly Ser Gln Val Thr Leu Lys Glu
        115                 120                 125

Ser Gly Pro Val Leu Val Lys Pro Thr Glu Thr Leu Thr Leu Thr Cys
    130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Val Tyr Tyr Asn Pro Ser Leu Lys Ser Arg Leu Thr
            180                 185                 190

Ile Thr Lys Asp Ala Ser Lys Asp Gln Val Ser Leu Lys Leu Ser Ser
        195                 200                 205

Val Thr Ala Ala Asp Thr Ala Val Tyr Tyr Cys Val Arg Arg Arg Ala
    210                 215                 220

Thr Gly Thr Gly Phe Asp Tyr Trp Gly Gln Gly Thr Leu Val Thr Val
225                 230                 235                 240

Ser Ser
```

<210> SEQ ID NO 18
<211> LENGTH: 339
<212> TYPE: DNA
<213> ORGANISM: Homo sapiens

<400> SEQUENCE: 18

```
agagtgaagt tcagcaggag cgcagacgcc ccgcgtacc  agcagggcca gaaccagctc     60
tataacgagc tcaatctagg acgaagagag gagtacgatg tttttggacaa gaggcgtggc    120 cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgctaa                           339
```

<210> SEQ ID NO 19
<211> LENGTH: 1689
<212> TYPE: DNA
<213> ORGANISM: Artificial Sequence
<220> FEATURE:
<223> OTHER INFORMATION: Synthesized

<400> SEQUENCE: 19

```
cggctccggt gcccgtcagt gggcagagcg cacatcgccc acagtcccg  agaagttggg      60 gggaggggtc ggcaattgaa ccggtgccta gagaaggtgg cgcggggtaa actgggaaag    120
tgatgtcgtg tactggctcc gccttttttcc cgagggtggg ggagaaccgt atataagtgc    180
agtagtcgcc gtgaacgttc tttttcgcaa cgggtttgcc gccagaacac aggatccgcc    240
accatggcct accagtgac  cgccttgctc ctgccgctgg ccttgctgct ccacgccgcc    300
aggccggaca tccagctcac ccagtccccg agctcgctgt ccgcctccgt gggagatcgg    360
gtcaccatca cgtgccgcgc cagccagtcg atttcctcct acctgaactg gtaccaacag    420
```

| | |
|---|---|
| aagcccggaa aagcccccgaa gcttctcatc tacgccgcct cgagcctgca gtcaggagtg | 480 |
| ccctcacggt tctccggctc cggttccggt actgatttca ccctgaccat ttcctccctg | 540 |
| caaccggagg acttcgctac ttactactgc cagcagtcgt actccacccc ctacactttc | 600 |
| ggacaaggca ccaaggtcga aatcaagggt ggcggtggct cgggcggtgg tgggtcgggt | 660 |
| ggcggcggat ctgaagtgca attggtggaa tcaggggag gacttgtgca gcctggagga | 720 |
| tcgctgagac tgtcatgtgc cgtgtccggc tttgccctgt ccaaccacgg gatgtcctgg | 780 |
| gtccgccgcg cgcctggaaa gggcctcgaa tgggtgtcgg gtattgtgta cagcggtagc | 840 |
| acctactatg ccgcatccgt gaaggggaga ttcaccatca gccgggacaa ctccaggaac | 900 |
| actctgtacc tccaaatgaa ttcgctgagg ccagaggaca ctgccatcta ctactgctcc | 960 |
| gcgcatggcg gagagtccga cgtctgggga caggggacca ccgtgaccgt gtctagcacc | 1020 |
| acgacgccag cgccgcgacc accaacaccg gcgcccacca tcgcgtcgca gcccctgtcc | 1080 |
| ctgcgcccag aggcgtgccg gccagcggcg ggggcgcag tgcacacgag ggggctggac | 1140 |
| ttcgcctgtg atatctacat ctgggcgccc ttggccggga cttgtggggt ccttctcctg | 1200 |
| tcactggtta tcacccttta ctgcaaacgg ggcagaaaga aactcctgta tatattcaaa | 1260 |
| caaccattta tgagaccagt acaaactact caagaggaag atggctgtag ctgccgattt | 1320 |
| ccagaagaag aagaaggagg atgtgaactg agagtgaagt tcagcaggag cgcagacgcc | 1380 |
| cccgcgtacc agcagggcca gaaccagctc tataacgagc tcaatctagg acgaagagag | 1440 |
| gagtacgatg ttttggacaa gaggcgtggc cgggaccctg agatgggggg aaagccgaga | 1500 |
| aggaagaacc ctcaggaagg cctgtacaat gaactgcaga agataagat ggcggaggcc | 1560 |
| tacagtgaga ttgggatgaa aggcgagcgc cggaggggca aggggcacga tggcctttac | 1620 |
| cagggtctca gtacagccac caaggacacc tacgacgccc ttcacatgca ggccctgccc | 1680 |
| cctcgctaa | 1689 |

<210> SEQ ID NO 20
<211> LENGTH: 1446
<212> TYPE: DNA
<213> ORGANISM: Artificial Sequence
<220> FEATURE:
<223> OTHER INFORMATION: Synthesized

<400> SEQUENCE: 20

| | |
|---|---|
| atggccttac cagtgaccgc cttgctcctg ccgctggcct tgctgctcca cgccgccagg | 60 |
| ccggacatcc agctcaccca gtccccgagc tcgctgtccg cctccgtggg agatcgggtc | 120 |
| accatcacgt gccgcgccag ccagtcgatt tcctcctacc tgaactggta ccaacagaag | 180 |
| cccggaaaag ccccgaagct tctcatctac gccgcctcga gcctgcagtc aggagtgccc | 240 |
| tcacggttct ccggctccgg ttccggtact gatttcaccc tgaccatttc ctccctgcaa | 300 |
| ccggaggact tcgctactta ctactgccag cagtcgtact ccacccccta cactttcgga | 360 |
| caaggcacca aggtcgaaat caaggtggc ggtggctcgg cggtggtgg gtcgggtggc | 420 |
| ggcggatctg aagtgcaatt ggtggaatca gggggaggac ttgtgcagcc tggaggatcg | 480 |
| ctgagactgt catgtgccgt gtccggcttt gccctgtcca accacgggat gtcctgggtc | 540 |
| cgccgcgcgc ctggaaaggg cctcgaatgg gtgtcgggta ttgtgtacag cggtagcacc | 600 |
| tactatgccg catccgtgaa ggggagatc accatcagcc gggacaactc caggaacact | 660 |
| ctgtacctcc aaatgaattc gctgaggcca gaggacactg ccatctacta ctgctccgcg | 720 |
| catggcggag agtccgacgt ctggggacag gggaccaccg tgaccgtgtc tagcaccacg | 780 |

| | |
|---|---|
| acgccagcgc cgcgaccacc aacaccggcg cccaccatcg cgtcgcagcc cctgtccctg | 840 |
| cgcccagagg cgtgccggcc agcggcgggg ggcgcagtgc acacgagggg gctggacttc | 900 |
| gcctgtgata tctacatctg ggcgcccttg gccgggactt gtggggtcct tctcctgtca | 960 |
| ctggttatca ccctttactg caaacggggc agaaagaaac tcctgtatat attcaaacaa | 1020 |
| ccatttatga gaccagtaca aactactcaa gaggaagatg gctgtagctg ccgatttcca | 1080 |
| gaagaagaag aaggaggatg tgaactgaga gtgaagttca gcaggagcgc agacgccccc | 1140 |
| gcgtacaagc agggccagaa ccagctctat aacgagctca atctaggacg aagagaggag | 1200 |
| tacgatgttt tggacaagag gcgtggccgg gaccctgaga tggggggaaa gccgagaagg | 1260 |
| aagaaccctc aggaaggcct gtacaatgaa ctgcagaaag ataagatggc ggaggcctac | 1320 |
| agtgagattg ggatgaaagg cgagcgccgg aggggcaagg ggcacgatgg cctttaccag | 1380 |
| ggtctcagta cagccaccaa ggacacctac gacgcccttc acatgcaggc cctgccccct | 1440 |
| cgctaa | 1446 |

<210> SEQ ID NO 21
<211> LENGTH: 1467
<212> TYPE: DNA
<213> ORGANISM: Artificial Sequence
<220> FEATURE:
<223> OTHER INFORMATION: Synthesized

<400> SEQUENCE: 21

| | |
|---|---|
| atggccttac cagtgaccgc cttgctcctg ccgctggcct tgctgctcca cgccgccagg | 60 |
| ccggacatcg tgatgaccca gtccccctcc agcctgacag tgacagccgg cgagaaggtg | 120 |
| acaatgatct gtaagtccag ccagagcctg ctgaacagcg gcgaccagaa gaactacctg | 180 |
| acctggtacc agcagaagcc tggccagccc cccaagctgc tgatcttctg gccagcaca | 240 |
| agggagagcg gcgtgcccga cagattcaca ggcagcggca gcggcaccga cttcacactg | 300 |
| accatttcct ccgtgcaggc cgaggacctc gccgtgtact actgccagaa cgactactcc | 360 |
| taccccctga cattcggcgc cggcaccaaa ctggagctga agggtggcgg tggctcgggc | 420 |
| ggtggtgggt cgggtggcgg cggatctcag gtgcagctcc agcagtccga tgccgagctg | 480 |
| gtgaagcccg gaagcagcgt caagatcagc tgtaaggcct ccggctacac cttcacagac | 540 |
| cacgccatcc actgggtgaa gcagaagccc gagcagggcc tggagtggat cggccacttt | 600 |
| agccccggaa acaccgacat caagtacaac gacaagttca agggcaaggc caccctgacc | 660 |
| gtggacagga gcagcagcac cgcctacatg cagctgaaca gcctgacaag cgaggacagc | 720 |
| gccgtgtact tctgcaagac ctccaccttc ttcttcgact actggggcca gggaaccacc | 780 |
| ctgacagtgt ccagcaccac gacgccagcg ccgcgaccac caacaccggc gcccaccatc | 840 |
| gcgtcgcagc cctgtccct gcgcccagag gcgtgccggc cagcggcggg gggcgcagtg | 900 |
| cacacgaggg gctggactt cgcctgtgat atctacatct gggcgccctt ggccgggact | 960 |
| tgtgggtcc ttctcctgtc actggttatc acccttact gcaaacgggg cagaaagaaa | 1020 |
| ctcctgtata tattcaaaca accatttatg agaccagtac aaactactca agaggaagat | 1080 |
| ggctgtagct gccgatttcc agaagaagaa gaaggaggat gtgaactgag agtgaagttc | 1140 |
| agcaggagcg cagacgcccc cgcgtacaag cagggccaga accagctcta taacgagctc | 1200 |
| aatctaggac gaagagagga gtacgatgtt ttggacaaga ggcgtggccg ggaccctgag | 1260 |
| atgggggaa agccgagaag gaagaaccct caggaaggcc tgtacaatga actgcagaaa | 1320 |

| | |
|---|---|
| gataagatgg cggaggccta cagtgagatt gggatgaaag gcgagcgccg gaggggcaag | 1380 |
| gggcacgatg gcctttacca gggtctcagt acagccacca aggacaccta cgacgccctt | 1440 |
| cacatgcagg ccctgccccc tcgctaa | 1467 |

<210> SEQ ID NO 22
<211> LENGTH: 3533
<212> TYPE: DNA
<213> ORGANISM: Artificial Sequence
<220> FEATURE:
<223> OTHER INFORMATION: Synthesized

<400> SEQUENCE: 22

| | |
|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |
| accatcagtt gcagggcaag tcaggacatt agtaaatatt taaattggta tcagcagaaa | 180 |
| ccagatggaa ctgttaaact cctgatctac catacatcaa gattacactc aggagtccca | 240 |
| tcaaggttca gtggcagtgg gtctggaaca gattattctc tcaccattag caacctggag | 300 |
| caagaagata ttgccactta ctttttgcca caggtaata cgcttccgta cacgttcgga | 360 |
| gggggaccaa gctggagat acaggtggc ggtggctcgg cgtggtgg gtcgggtggc | 420 |
| ggcggatctg aggtgaaact gcaggagtca ggacctggcc tggtggcgcc ctcacagagc | 480 |
| ctgtccgtca catgcactgt ctcaggggtc tcattacccg actatggtgt aagctggatt | 540 |
| cgccagcctc cacgaaaggg tctggagtgg ctgggagtaa tatggggtag tgaaaccaca | 600 |
| tactataatt cagctctcaa atccagactg accatcatca aggacaactc caagagccaa | 660 |
| gttttcttaa aaatgaacag tctgcaaact gatgacacag ccatttacta ctgtgccaaa | 720 |
| cattattact acggtggtag ctatgctatg gactactggg gccaaggaac ctcagtcacc | 780 |
| gtctcctcaa ccacgacgcc agcgccgcga ccaccaacac cggcgcccac catcgcgtcg | 840 |
| cagcccctgt ccctgcgccc agaggcgtgc cggccagcgg cggggggcgc agtgcacacg | 900 |
| aggggggctgg acttcgcctg tgatatctac atctgggcgc ccttggccgg acttgtggg | 960 |
| gtccttctcc tgtcactggt tatcacccctt tactgcaaac ggggcagaaa gaaactcctg | 1020 |
| tatatattca acaaccatt tatgagacca gtacaaacta ctcaagagga gatggctgt | 1080 |
| agctgccgat ttccagaaga agaagaagga ggatgtgaac tgagagtgaa gttcagcagg | 1140 |
| agcgcagacg cccccgcgta caagcagggc cagaaccagc tctataacga gctcaatcta | 1200 |
| ggacgaagag aggagtacga tgttttggac aagaggcgtg gccgggaccc tgagatgggg | 1260 |
| ggaaagccga aaggaagaa ccctcaggaa ggcctgtaca atgaactgca gaaagataag | 1320 |
| atggcgagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc ccctcgcta atctagaggc gcgcccctct cctccccccc ccctaacgt | 1500 |
| tactggccga agccgcttgg aataaggccg gtgtgcgttt gtctatatgt tattttccac | 1560 |
| catattgccg tcttttggca atgtgagggc ccggaaacct ggccctgtct tcttgacgag | 1620 |
| cattcctagg ggtctttccc ctctcgccaa aggaatgcaa gtctgttga atgtcgtgaa | 1680 |
| ggaagcagtt cctctggaag cttcttgaag acaaacaacg tctgtagcga ccctttgcag | 1740 |
| gcagcggaac cccccacctg gcgacaggtg cctctgcggc caaaagccac gtgtataaga | 1800 |
| tacacctgca aaggcggcac aaccccagtg ccacgttgtg agttggatag ttgtggaaag | 1860 |
| agtcaaatgg ctctcctcaa gcgtattcaa caaggggctg aaggatgccc agaaggtacc | 1920 |

```
ccattgtatg ggatctgatc tggggcctcg gtacacatgc tttacatgtg tttagtcgag    1980
gttaaaaaaa cgtctaggcc ccccgaacca cggggacgtg gttttccttt gaaaaacacg    2040
atgataatat ggccacaacc catatgatgg ccttaccagt gaccgccttg ctcctgccgc    2100
tggccttgct gctccacgcc gccaggccgg acatcgtgat gacccagtcc ccctccagcc    2160
tgacagtgac agccggcgag aaggtgacaa tgatctgtaa gtccagccag agcctgctga    2220
acagcggcga ccagaagaac tacctgacct ggtaccagca gaagcctggc cagcccccca    2280
agctgctgat cttctgggcc agcacaaggg agagcggcgt gcccgacaga ttcacaggca    2340
gcggcagcgg caccgacttc acactgacca tttcctccgt gcaggccgag gacctcgccg    2400
tgtactactg ccagaacgac tactcctacc ccctgacatt cggcgccggc accaaactgg    2460
agctgaaggg tggcggtggc tcgggcggtg gtgggtcggg tggcggcgga tctcaggtgc    2520
agctccagca gtccgatgcc gagctggtga agcccggaag cagcgtcaag atcagctgta    2580
aggcctccgg ctacaccttc acagaccacg ccatccactg ggtgaagcag aagcccgagc    2640
agggcctgga gtggatcggc cactttagcc ccggaaacac cgacatcaag tacaacgaca    2700
agttcaaggg caaggccacc ctgaccgtgg acaggagcag cagcaccgcc tacatgcagc    2760
tgaacagcct gacaagcgag gacagcgccg tgtacttctg caagacctcc accttcttct    2820
tcgactactg gggccaggga accaccctga cagtgtccag caccacgacg ccagcgccgc    2880
gaccaccaac accggcgccc accatcgcgt cgcagcccct gtccctgcgc ccagaggcgt    2940
gccggccagc ggcgggggc gcagtgcaca cgagggggct ggacttcgcc tgtgatatct    3000
acatctgggc gcccttggcc gggacttgtg gggtccttct cctgtcactg gttatcaccc    3060
tttactgcaa acggggcaga aagaaactcc tgtatatatt caaacaacca tttatgagac    3120
cagtacaaac tactcaagag gaagatggct gtagctgccg atttccagaa gaagaagaag    3180
gaggatgtga actgagagtg aagttcagca ggagcgcaga cgcccccgcg tacaagcagg    3240
gccagaacca gctctataac gagctcaatc taggacgaag agaggagtac gatgttttgg    3300
acaagaggcg tggccgggac cctgagatgg ggggaaagcc gagaaggaag aaccctcagg    3360
aaggcctgta caatgaactg cagaaagata agatggcgga ggcctacagt gagattggga    3420
tgaaaggcga gcgccggagg ggcaaggggc acgatggcct ttaccagggt ctcagtacag    3480
ccaccaagga cacctacgac gcccttcaca tgcaggcccc gccccctcgc taa          3533
```

<210> SEQ ID NO 23
<211> LENGTH: 3533
<212> TYPE: DNA
<213> ORGANISM: Artificial Sequence
<220> FEATURE:
<223> OTHER INFORMATION: Synthesized

<400> SEQUENCE: 23

```
atggccttac cagtgaccgc cttgctcctg ccgctggcct tgctgctcca cgccgccagg      60
ccggatatcc agatgaccca gagcccgagc agcctgagcg cgagcgtggg tgatcgcgtg     120
accattacct gcagggcaag tcaggacatt agtaaatatt taaattggta tcagcagaaa     180
ccgggtaaag cgccgaaact gttaatttat catacatcaa gattacactc aggcgtgccg     240
tcgcgtttta gcggctcggg ttcgggcacc gattttaccc tgaccatctc gagcttgcag     300
ccggaggact cgccaccta ctattgccaa caggtaata cgcttccgta cacgttcggt      360
cagggcacca aagtggagat caaaggtggc ggtggctcgg gcggtggtgg gtcgggtggc     420
```

| | |
|---|---|
| ggcggatctg aggtgcagct ggtggagtct gggggaggct tggtacagcc tgggggggtcc | 480 |
| ctgagactct cctgtgcagc ctctggagtg tccctgcctg attatggcgt gtcctgggtc | 540 |
| cgccaggctc cagggaaggg gctggagtgg gtttcagtga tctggggcag cgagacaacc | 600 |
| tactacaaca cgcccctgaa gtcccgattc accatctcca gagacaatgc caagaactca | 660 |
| ctgtatctgc aaatgaacag cctgagagcc gaggacacgg ctgtgtatta ctgtgcgaag | 720 |
| cactactact acggcggcag ctacgctatg gactactggg gccaaggaac cctggtcacc | 780 |
| gtgtcctcaa ccacgacgcc agcgccgcga ccaccaacac cggcgcccac catcgcgtcg | 840 |
| cagcccctgt ccctgcgccc agaggcgtgc cggccagcgg cggggggcgc agtgcacacg | 900 |
| aggggggctgg acttcgcctg tgatatctac atctgggcgc ccttggccgg gacttgtggg | 960 |
| gtccttctcc tgtcactggt tatcaccctt tactgcaaac ggggcagaaa gaaactcctg | 1020 |
| tatatattca acaaccatt tatgagacca gtacaaacta ctcaagagga gatggctgt | 1080 |
| agctgccgat ttccagaaga agaagaagga ggatgtgaac tgagagtgaa gttcagcagg | 1140 |
| agcgcagacg cccccgcgta caagcagggc cagaaccagc tctataacga gctcaatcta | 1200 |
| ggacgaagag aggagtacga tgttttggac aagaggcgtg gccgggaccc tgagatgggg | 1260 |
| ggaaagccga aaggaagaa ccctcaggaa ggcctgtaca tgaactgca gaaagataag | 1320 |
| atggcggagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc cccctcgcta atctagaggc gcgcccctct ccctcccccc ccctaacgt | 1500 |
| tactggccga agccgcttgg aataaggccg gtgtgcgttt gtctatatgt tatttccac | 1560 |
| catattgccg tcttttggca atgtgagggc ccggaaacct ggccctgtct tcttgacgag | 1620 |
| cattcctagg ggtctttccc ctctcgccaa aggaatgcaa ggtctgttga atgtcgtgaa | 1680 |
| ggaagcagtt cctctggaag cttcttgaag acaaacaacg tctgtagcga ccctttgcag | 1740 |
| gcagcggaac cccccacctg cgacaggtg cctctgcggc caaaagccac gtgtataaga | 1800 |
| tacacctgca aaggcggcac aaccccagtg ccacgttgtg agttggatag ttgtggaaag | 1860 |
| agtcaaatgg ctctcctcaa gcgtattcaa caaggggctg aaggatgccc agaaggtacc | 1920 |
| ccattgtatg ggatctgatc tggggcctcg gtacacatgc tttacatgtg tttagtcgag | 1980 |
| gttaaaaaaa cgtctaggcc ccccgaacca cggggacgtg gttttccttt gaaaaacacg | 2040 |
| atgataatat ggccacaacc catatgatgg ccttaccagt gaccgccttg ctcctgccgc | 2100 |
| tggccttgct gctccacgcc gccaggccgg acatcgtgat gacccagtcc ccctccagcc | 2160 |
| tgacagtgac agccggcgag aaggtgacaa tgatctgtaa gtccagccag agcctgctga | 2220 |
| acagcggcga ccagaagaac tacctgacct ggtaccagca gaagcctggc cagccccca | 2280 |
| agctgctgat cttctgggcc agcacaaggg agagcggcgt gcccgacaga ttcacaggca | 2340 |
| gcggcagcgg caccgacttc acactgacca tttcctccgt gcaggccgag gacctcgccg | 2400 |
| tgtactactg ccagaacgac tactcctacc ccctgacatt cggcgccggc accaaactgg | 2460 |
| agctgaaggg tggcggtggc tcgggcggtg gtgggtcggg tggcggcgga tctcaggtgc | 2520 |
| agctccagca gtccgatgcc gagctggtga gcccggaag cagcgtcaag atcagctgta | 2580 |
| aggcctccgg ctacaccttc acagaccacg ccatccactg ggtgaagcag aagcccgagc | 2640 |
| agggcctgga gtggatcggc cactttagcc ccggaaacac cgacatcaag tacaacgaca | 2700 |
| agttcaaggg caaggccacc ctgaccgtgg acaggagcag cagcaccgcc tacatgcagc | 2760 |
| tgaacagcct gacaagcgag gacagcgccg tgtacttctg caagacctcc accttcttct | 2820 |

| | |
|---|---|
| tcgactactg gggccaggga accaccctga cagtgtccag caccacgacg ccagcgccgc | 2880 |
| gaccaccaac accggcgccc accatcgcgt cgcagcccct gtccctgcgc ccagaggcgt | 2940 |
| gccggccagc ggcgggggc gcagtgcaca cgagggggct ggacttcgcc tgtgatatct | 3000 |
| acatctgggc gcccttggcc gggacttgtg gggtccttct cctgtcactg gttatcaccc | 3060 |
| tttactgcaa acggggcaga aagaaactcc tgtatatatt caaacaacca tttatgagac | 3120 |
| cagtacaaac tactcaagag gaagatggct gtagctgccg atttccagaa gaagaagaag | 3180 |
| gaggatgtga actgagagtg aagttcagca ggagcgcaga cgcccccgcg tacaagcagg | 3240 |
| gccagaacca gctctataac gagctcaatc taggacgaag agaggagtac gatgttttgg | 3300 |
| acaagaggcg tggccgggac cctgagatgg ggggaaagcc gagaaggaag aaccctcagg | 3360 |
| aaggcctgta caatgaactg cagaaagata agatggcgga ggcctacagt gagattggga | 3420 |
| tgaaaggcga gcgccggagg ggcaaggggc acgatggcct ttaccagggt ctcagtacag | 3480 |
| ccaccaagga cacctacgac gcccttcaca tgcaggccct gccccctcgc taa | 3533 |

<210> SEQ ID NO 24
<211> LENGTH: 3545
<212> TYPE: DNA
<213> ORGANISM: Artificial Sequence
<220> FEATURE:
<223> OTHER INFORMATION: Synthesized

<400> SEQUENCE: 24

| | |
|---|---|
| atggccttac cagtgaccgc cttgctcctg ccgctggcct tgctgctcca cgccgccagg | 60 |
| ccggatatcc agatgaccca gagcccaagc tccctgtccg cctctgtggg cgacagggtg | 120 |
| accatcacat gccgcgccag ccagacaatc tggtcctacc tgaactggta tcagcagaga | 180 |
| cccggcaagg cccctaatct gctgatctac gcagcatcta gcctgcagtc tggagtgccc | 240 |
| tcccggttct ctggaagagg atccggaacc gacttcaccc tgacaatctc ctctctgcag | 300 |
| gccgaggact tcgccacata ctattgccag cagagctatt ccatccctca gacctttggc | 360 |
| cagggcacaa agctggagat caagggcggc ggcggctctg gaggaggagg aagcggagga | 420 |
| ggaggatccc aggtgcagct gcagcagagc ggaccaggac tggtgaagcc ctcccagacc | 480 |
| ctgtctctga catgtgccat cagcggcgat tccgtgagct ccaacagcgc cgcctggaat | 540 |
| tggatccggc agtctcccag cagaggactg gagtggctgg aaggacctac ctatcgctcc | 600 |
| aagtggtaca cgattatgc cgtgtctgtg aagagccgga tcaccatcaa ccctgacaca | 660 |
| tctaagaatc agttcagcct gcagctgaat tccgtgaccc cagaggacac agccgtgtac | 720 |
| tattgtgcaa gggaggtgac cggcgacctg gaggatgcct ttgacatctg gggccagggc | 780 |
| accatggtga cagtgtctag caccacgacg ccagcgccgc gaccaccaac accggcgccc | 840 |
| accatcgcgt cgcagcccct gtccctgcgc ccagaggcgt gccggccagc ggcgggggc | 900 |
| gcagtgcaca cgagggggct ggacttcgcc tgtgatatct acatctgggc gcccttggcc | 960 |
| gggacttgtg gggtccttct cctgtcactg gttatcaccc tttactgcaa acggggcaga | 1020 |
| aagaaactcc tgtatatatt caaacaacca tttatgagac cagtacaaac tactcaagag | 1080 |
| gaagatggct gtagctgccg atttccagaa gaagaagaag gaggatgtga actgagagtg | 1140 |
| aagttcagca ggagcgcaga cgcccccgcg tacaagcagg gccagaacca gctctataac | 1200 |
| gagctcaatc taggacgaag agaggagtac gatgttttgg acaagaggcg tggccgggac | 1260 |
| cctgagatgg ggggaaagcc gagaaggaag aaccctcagg aaggcctgta caatgaactg | 1320 |

```
cagaaagata agatggcgga ggcctacagt gagattggga tgaaaggcga gcgccggagg   1380
ggcaaggggc acgatggcct ttaccagggt ctcagtacag ccaccaagga cacctacgac   1440
gcccttcaca tgcaggccct gcccctcgc taatctagag gcgcgcccct ctcctcccc    1500 ccccctaac gttactggcc gaagccgctt ggaataaggc cggtgtgcgt ttgtctatat   1560
gttattttcc accatattgc cgtcttttgg caatgtgagg gcccggaaac ctggccctgt   1620
cttcttgacg agcattccta ggggtctttc ccctctcgcc aaaggaatgc aaggtctgtt   1680
gaatgtcgtg aaggaagcag ttcctctgga agcttcttga agacaaacaa cgtctgtagc   1740
gaccctttgc aggcagcgga accccccacc tggcgacagg tgcctctgcg gccaaaagcc   1800
acgtgtataa gatacacctg caaaggcggc acaaccccag tgccacgttg tgagttggat   1860
agttgtggaa agagtcaaat ggctctcctc aagcgtattc aacaaggggc tgaaggatgc   1920
ccagaaggta ccccattgta tgggatctga tctggggcct cggtacacat gctttacatg   1980
tgtttagtcg aggttaaaaa aacgtctagg ccccccgaac cacggggacg tggttttcct   2040
ttgaaaaaca cgatgataat atggccacaa cccatatgat ggccttacca gtgaccgcct   2100
tgctcctgcc gctggccttg ctgctccacg ccgccaggcc ggacatcgtg atgacccagt   2160 cccccctccag cctgacagtg acagccgcg agaaggtgac aatgatctgt aagtccagcc   2220
agagcctgct gaacagcggc gaccagaaga actacctgac ctggtaccag cagaagcctg   2280
gccagccccc caagctgctg atcttctggg ccagcacaag ggagagcggc gtgcccgaca   2340
gattcacagg cagcggcagc ggcaccgact tcacactgac catttcctcc gtgcaggccg   2400
aggacctcgc cgtgtactac tgccagaacg actactccta cccctgaca ttcggcgccg   2460 gcaccaaact ggagctgaag ggtggcggtg gctcgggcgg tggtgggtcg ggtggcggcg   2520
gatctcaggt gcagctccag cagtccgatg ccgagctggt gaagcccgga agcagcgtca   2580
agatcagctg taaggcctcc ggctacacct tcacagacca cgccatccac tgggtgaagc   2640
agaagcccga gcagggcctg gagtggatcg gccactttag ccccggaaac accgacatca   2700
agtacaacga caagttcaag ggcaaggcca ccctgaccgt ggacaggagc agcagcaccg   2760
cctacatgca gctgaacagc ctgacaagcg aggacagcgc cgtgtacttc tgcaagacct   2820
ccaccttctt cttcgactac tggggccagg gaaccaccct gacagtgtcc agcaccacga   2880
cgccagcgcc gcgaccacca caccggcgc ccaccatcgc gtcgcagccc ctgtccctgc   2940
gcccagaggc gtgccggcca gcggcgggg gcgcagtgca cacgaggggg ctggacttcg   3000
cctgtgatat ctacatctgg gcgcccttgg ccgggacttg tggggtcctt ctcctgtcac   3060
tggttatcac ccttactgc aaacggggca gaaagaaact cctgtatata ttcaaacaac   3120
catttatgag accagtacaa actactcaag aggaagatgg ctgtagctgc cgatttccag   3180
aagaagaaga aggaggatgt gaactgagag tgaagttcag caggagcgca gacgcccccg   3240
cgtacaagca gggccagaac cagctctata cgagctcaa tctaggacga agagaggagt   3300
acgatgtttt ggacaagagg cgtggccggg accctgagat gggggaaag ccgagaagga   3360 agaaccctca ggaaggcctg tacaatgaac tgcagaaaga taagatggcg gaggcctaca   3420
gtgagattgg gatgaaaggc gagcgccgga ggggcaaggg gcacgatggc ctttaccagg   3480
gtctcagtac agccaccaag gacacctacg acgcccttca catgcaggcc ctgcccctc    3540 gctaa                                                              3545

<210> SEQ ID NO 25
<211> LENGTH: 3518
```

<212> TYPE: DNA
<213> ORGANISM: Artificial Sequence
<220> FEATURE:
<223> OTHER INFORMATION: Synthesized

<400> SEQUENCE: 25

```
atggccttac cagtgaccgc cttgctcctg ccgctggcct tgctgctcca cgccgccagg      60
ccggacatcc agctcaccca gtccccgagc tcgctgtccg cctccgtggg agatcgggtc     120
accatcacgt gccgcgccag ccagtcgatt tcctcctacc tgaactggta ccaacagaag     180
cccggaaaag ccccgaagct tctcatctac gccgcctcga gcctgcagtc aggagtgccc     240
tcacggttct ccggctccgg ttccggtact gatttcaccc tgaccatttc ctccctgcaa     300
ccggaggact cgctactta ctactgccag cagtcgtact ccacccccta cactttcgga     360
caaggcacca aggtcgaaat caaggtggc ggtggctcgg gcggtggtgg gtcgggtggc     420
ggcggatctg aagtgcaatt ggtggaatca gggggaggac ttgtgcagcc tggaggatcg     480
ctgagactgt catgtgccgt gtccggcttt gccctgtcca accacgggat gtcctgggtc     540
cgccgcgcgc ctggaaaggg cctcgaatgg gtgtcgggta ttgtgtacag cggtagcacc     600
tactatgccg catccgtgaa ggggagattc accatcagcc gggacaactc caggaacact     660
ctgtacctcc aaatgaattc gctgaggcca gaggacactg ccatctacta ctgctccgcg     720
catggcggag agtccgacgt ctggggacag gggaccaccg tgaccgtgtc tagcaccacg     780
acgccagcgc cgcgaccacc aacaccggcg cccaccatcg cgtcgcagcc cctgtccctg     840
cgcccagagg cgtgccggcc agcggcgggg gcgcagtgc acgaggggg ctggacttc     900
gcctgtgata tctacatctg ggcgcccttg gccgggactt gtggggtcct tctcctgtca     960
ctggttatca ccctttactg caacggggc agaaagaaac tcctgtatat attcaaacaa    1020
ccatttatga gaccagtaca aactactcaa gaggaagatg gctgtagctg ccgatttcca    1080
gaagaagaag aaggaggatg tgaactgaga gtgaagttca gcaggagcgc agacgccccc    1140
gcgtacaagc agggccagaa ccagctctat aacgagctca atctaggacg aagagaggag    1200
tacgatgttt tggacaagag gcgtggccgg gaccctgaga tggggggaaa gccgagaagg    1260
aagaacctc aggaaggcct gtacaatgaa ctgcagaaag ataagatggc ggaggcctac    1320
agtgagattg ggatgaaagg cgagcgccgg aggggcaagg ggcacgatgg cctttaccag    1380
ggtctcagta cagccaccaa ggacacctac gacgcccttc acatgcaggc cctgccccct    1440
cgctaatcta gaggcgcgcc cctctccctc cccccccct aacgttactg gccgaagccg    1500
cttggaataa ggccggtgtg cgtttgtcta tatgttattt tccaccatat tgccgtcttt    1560
tggcaatgtg agggcccgga aacctggccc tgtcttcttg acgagcattc ctagggtct    1620
ttcccctctc gccaaaggaa tgcaaggtct gttgaatgtc gtgaaggaag cagttcctct    1680
ggaagcttct tgaagacaaa caacgtctgt agcgaccctt gcaggcagc ggaaccccc    1740
acctggcgac aggtgcctct gcggccaaaa gccacgtgta agatacac ctgcaaggc     1800
ggcacaaccc cagtgccacg ttgtgagttg gatagttgtg gaaagagtca atggctctc     1860
ctcaagcgta ttcaacaagg ggctgaagga tgcccagaag gtaccccatt gtatgggatc    1920
tgatctgggg cctcggtaca catgctttac atgtgtttag tcgaggttaa aaaaacgtct    1980
aggcccccg aaccacgggg acgtggtttt cctttgaaaa acacgatgat aatatggcca    2040
caacccatat gatggcctta ccagtgaccg ccttgctcct gccgctggcc ttgctgctcc    2100
acgccgccag gccggacatc gtgatgaccc agtccccctc cagcctgaca gtgacagccg    2160
```

```
gcgagaaggt gacaatgatc tgtaagtcca gccagagcct gctgaacagc ggcgaccaga    2220
agaactacct gacctggtac cagcagaagc ctggccagcc ccccaagctg ctgatcttct    2280
gggccagcac aagggagagc ggcgtgcccg acagattcac aggcagcggc agcggcaccg    2340
acttcacact gaccatttcc tccgtgcagg ccgaggacct cgccgtgtac tactgccaga    2400
acgactactc ctaccccctg acattcggcg ccggcaccaa actggagctg aagggtggcg    2460
gtggctcggg cggtggtggg tcgggtggcg cggatctca ggtgcagctc cagcagtccg    2520
atgccgagct ggtgaagccc ggaagcagcg tcaagatcag ctgtaaggcc tccggctaca    2580
ccttcacaga ccacgccatc cactgggtga agcagaagcc cgagcagggc ctggagtgga    2640
tcggccactt tagccccgga aacaccgaca tcaagtacaa cgacaagttc aagggcaagg    2700
ccaccctgac cgtggacagg agcagcagca ccgcctacat gcagctgaac agcctgacaa    2760
gcgaggacag cgccgtgtac ttctgcaaga cctccacctt cttcttcgac tactggggcc    2820
agggaaccac cctgacagtg tccagcacca cgacgccagc gccgcgacca ccaacaccgg    2880
cgcccaccat cgcgtcgcag cccctgtccc tgcgcccaga ggcgtgccgg ccagcggcgg    2940
ggggcgcagt gcacacgagg gggctggact tcgcctgtga tatctacatc tgggcgccct    3000
tggccgggac ttgtggggtc cttctcctgt cactggttat cacccttac tgcaaacggg     3060 gcagaaagaa actcctgtat atattcaaac aaccatttat gagaccagta caaactactc    3120
aagaggaaga tggctgtagc tgccgatttc cagaagaaga agaaggagga gtgaactga    3180 gagtgaagtt cagcaggagc gcagacgccc ccgcgtacaa gcagggccag aaccagctct    3240
ataacgagct caatctagga cgaagagagg agtacgatgt tttggacaag aggcgtggcc    3300
gggaccctga gatggggga agccgagaa ggaagaaccc tcaggaaggc ctgtacaatg    3360
aactgcagaa agataagatg gcggaggcct acagtgagat tgggatgaaa ggcgagcgcc    3420
ggaggggcaa ggggcacgat ggcctttacc agggtctcag tacagccacc aaggacacct    3480
acgacgccct tcacatgcag gccctgcccc ctcgctaa                           3518
```

<210> SEQ ID NO 26
<211> LENGTH: 2994
<212> TYPE: DNA
<213> ORGANISM: Artificial Sequence
<220> FEATURE:
<223> OTHER INFORMATION: Synthesized

<400> SEQUENCE: 26

```
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360
ggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaagggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
```

```
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cgggggggcgc agtgcacacg   900 aggggggctgg acttcgcctg tgatatctac atctgggcgc ccttggccgg gacttgtggg   960
gtccttctcc tgtcactggt tatcaccctt tactgcaaac ggggcagaaa gaaactcctg   1020
tatatattca acaaccatt tatgagacca gtacaaacta ctcaagagga gatggctgt    1080 agctgccgat ttccagaaga agaagaagga ggatgtgaac tgagagtgaa gttcagcagg   1140
agcgcagacg ccccgcgta caagcagggc cagaaccagc tctataacga gctcaatcta   1200
ggacgaagag aggagtacga tgttttggac aagaggcgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgctc tagagccacg aacttctctc tgttaaagca agcaggagac   1500
gtggaagaaa accccggtcc tcatatgatg gccttaccag tgaccgcctt gctcctgccg   1560
ctggccttgc tgctccacgc cgccaggccg gacatcgtga tgacccagtc ccctccagc   1620 ctgacagtga cagccggcga aaggtgacaa tgatctgta agtccagcca gagcctgctg   1680
aacagcggcg accagaagaa ctacctgacc tggtaccagc agaagcctgg ccagccccc    1740 aagctgctga tcttctgggc cagcacaagg gagagcggcg tgcccgacag attcacaggc   1800
agcggcagcg gcaccgactt cacactgacc atttcctccg tgcaggccga ggacctcgcc   1860
gtgtactact gccagaacga ctactcctac cccctgacat tcggcgccgg caccaaactg   1920
gagctgaagg gtggcggtgg ctcgggcggt ggtgggtcgg gtgcggcgg atctcaggtg   1980 cagctccagc agtccgatgc cgagctggtg aagcccggaa gcagcgtcaa gatcagctgt   2040
aaggcctccg gctacacctt cacagaccac gccatccact gggtgaagca gaagcccgag   2100
cagggcctgg agtggatcgg ccactttagc cccggaaaca ccgacatcaa gtacaacgac   2160
aagttcaagg gcaaggccac cctgaccgtg gacaggagca gcagcaccgc ctacatgcag   2220
ctgaacagcc tgacaagcga ggacagcgcc gtgtacttct gcaagacctc caccttcttc   2280
ttcgactact ggggccaggg aaccaccctg acagtgtcca gcaccacgac gccagcgccg   2340
cgaccaccaa caccggcgcc caccatcgcg tcgcagcccc tgtccctgcg cccagaggcg   2400
tgccggccag cggcgggggg cgcagtgcac acgagggggg tggacttcgc ctgtgatatc   2460
tacatctggg cgcccttggc cgggacttgt ggggtccttc tcctgtcact ggttatcacc   2520
ctttactgca aacggggcag aaagaaactc tgtatatat tcaaacaacc atttatgaga   2580
ccagtacaaa ctactcaaga ggaagatggc tgtagctgcc gatttccaga agaagaagaa   2640
ggaggatgtg aactgagagt gaagttcagc aggagcgcag acgccccgc gtacaagcag   2700 ggccagaacc agctctataa cgagctcaat ctaggacgaa gagaggagta cgatgttttg   2760
gacaagaggc gtggccggga ccctgagatg ggggaaagc cgagaaggaa gaaccctcag   2820
gaaggcctgt acaatgaact gcagaaagat aagatggcgg aggcctacag tgagattggg   2880
atgaaaggcg agcgccggag gggcaagggg cacgatggcc tttaccaggg tctcagtaca   2940
gccaccaagg acacctacga cgcccttcac atgcaggccc tgccccctcg ctaa          2994
```

<210> SEQ ID NO 27

<211> LENGTH: 2994
<212> TYPE: DNA
<213> ORGANISM: Artificial Sequence
<220> FEATURE:
<223> OTHER INFORMATION: Synthesized

<400> SEQUENCE: 27

| | |
|---|---|
| atggccttac cagtgaccgc cttgctcctg ccgctggcct tgctgctcca cgccgccagg | 60 |
| ccggatatcc agatgaccca gagcccgagc agcctgagcg cgagcgtggg tgatcgcgtg | 120 |
| accattacct gcagggcaag tcaggacatt agtaaatatt taaattggta tcagcagaaa | 180 |
| ccgggtaaag cgccgaaact gttaatttat catacatcaa gattacactc aggcgtgccg | 240 |
| tcgcgttttta gcggctcggg ttcgggcacc gattttaccc tgaccatctc gagcttgcag | 300 |
| ccggaggact tcgccaccta ctattgccaa caggtaata cgcttccgta cacgttcggt | 360 |
| cagggcacca aagtggagat caaaggtggc ggtggctcgg gcggtggtgg gtcgggtggc | 420 |
| ggcggatctg aggtgcagct ggtggagtct gggggaggct tggtacagcc tgggggtcc | 480 |
| ctgagactct cctgtgcagc ctctggagtg tccctgcctg attatggcgt gtcctgggtc | 540 |
| cgccaggctc cagggaaggg gctggagtgg gtttcagtga tctggggcag cgagacaacc | 600 |
| tactacaaca gcgccctgaa gtcccgattc accatctcca gagacaatgc caagaactca | 660 |
| ctgtatctgc aaatgaacag cctgagagcc gaggacacgg ctgtgtatta ctgtgcgaag | 720 |
| cactactact acggcggcag ctacgctatg gactactggg gccaaggaac cctggtcacc | 780 |
| gtgtcctcaa ccacgacgcc agcgccgcga ccaccaacac cggcgcccac catcgcgtcg | 840 |
| cagcccctgt ccctgcgccc agaggcgtgc cggccagcgg cggggggcgc agtgcacacg | 900 |
| aggggggctgg acttcgcctg tgatatctac atctgggcgc ccttggccgg gacttgtggg | 960 |
| gtccttctcc tgtcactggt tatcaccctt tactgcaaac ggggcagaaa gaaactcctg | 1020 |
| tatatattca acaaccatt tatgagacca gtacaaacta ctcaagagga gatggctgt | 1080 |
| agctgccgat ttccagaaga agaagaagga ggatgtgaac tgagagtgaa gttcagcagg | 1140 |
| agcgcagacg cccccgcgta caagcagggc cagaaccagc tctataacga gctcaatcta | 1200 |
| ggacgaagag aggagtacga tgtttttggac aagaggcgtg gccgggaccc tgagatgggg | 1260 |
| ggaaagccga aaggaagaa ccctcaggaa ggcctgtaca atgaactgca gaaagataag | 1320 |
| atggcggagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc ccctcgctc tagagccacg aacttctctc tgttaaagca agcaggagac | 1500 |
| gtggaagaaa accccggtcc tcatatgatg gccttaccag tgaccgcctt gctcctgccg | 1560 |
| ctggccttgc tgctccacgc cgccaggccg gacatcgtga tgacccagtc ccctccagc | 1620 |
| ctgacagtga cagccggcga aaggtgaca atgatctgta agtccagcca gagcctgctg | 1680 |
| aacagcggcg accagaagaa ctacctgacc tggtaccagc agaagcctgg ccagcccccc | 1740 |
| aagctgctga tcttctgggc cagcacaagg gagagcggcg tgcccgacag attcacaggc | 1800 |
| agcggcagcg gcaccgactt cacactgacc atttcctccg tgcaggccga ggacctcgcc | 1860 |
| gtgtactact gccagaacga ctactcctac ccctgacat cggcgccgg caccaaactg | 1920 |
| gagctgaagg gtggcggtgg ctcggccggt ggtgggtcgg gtgcggcgg atctcaggtg | 1980 |
| cagctccagc agtccgatgc cgagctggtg aagcccggaa gcagcgtcaa gatcagctgt | 2040 |
| aaggcctccg gctacacctt cacagaccac gccatccact gggtgaagca gaagcccgag | 2100 |
| cagggcctgg agtggatcgg ccactttagc cccggaaaca ccgacatcaa gtacaacgac | 2160 |

```
aagttcaagg gcaaggccac cctgaccgtg gacaggagca gcagcaccgc ctacatgcag    2220
ctgaacagcc tgacaagcga ggacagcgcc gtgtacttct gcaagacctc caccttcttc    2280
ttcgactact ggggccaggg aaccaccctg acagtgtcca gcaccacgac gccagcgccg    2340
cgaccaccaa caccggcgcc caccatcgcg tcgcagcccc tgtccctgcg cccagaggcg    2400
tgccggccag cggcgggggg cgcagtgcac acgaggggc tggacttcgc ctgtgatatc      2460
tacatctggg cgcccttggc cgggacttgt ggggtccttc tcctgtcact ggttatcacc    2520
ctttactgca aacggggcag aaagaaactc ctgtatatat tcaaacaacc atttatgaga    2580
ccagtacaaa ctactcaaga ggaagatggc tgtagctgcc gatttccaga agaagaagaa    2640
ggaggatgtg aactgagagt gaagttcagc aggagcgcag acgccccgc gtacaagcag      2700 ggccagaacc agctctataa cgagctcaat ctaggacgaa gagaggagta cgatgttttg    2760
gacaagaggc gtggccggga ccctgagatg gggggaaagc cgagaaggaa gaaccctcag    2820
gaaggcctgt acaatgaact gcagaaagat aagatggcgg aggcctacag tgagattggg    2880
atgaaaggcg agcgccggag gggcaagggg cacgatggcc tttaccaggg tctcagtaca    2940
gccaccaagg acacctacga cgcccttcac atgcaggccc tgcccctcg ctaa            2994

<210> SEQ ID NO 28
<211> LENGTH: 3009
<212> TYPE: DNA
<213> ORGANISM: Artificial Sequence
<220> FEATURE:
<223> OTHER INFORMATION: Synthesized

<400> SEQUENCE: 28
atggccttac cagtgaccgc cttgctcctg ccgctggcct tgctgctcca cgccgccagg      60
ccggatatcc agatgaccca gagcccaagc tccctgtccg cctctgtggg cgacagggtg    120
accatcacat gccgcgccag ccagacaatc tggtcctacc tgaactggta tcagcagaga    180
cccggcaagg cccctaatct gctgatctac gcagcatcta gcctgcagtc tggagtgccc    240
tcccggttct ctggaagagg atccggaacc gacttcaccc tgacaatctc ctctctgcag    300
gccgaggact tcgccacata ctattgccag cagagctatt ccatccctca gacctttggc    360
cagggcacaa agctggagat caagggcggc ggcggctctg gaggaggagg aagcggagga    420
ggaggatccc aggtgcagct gcagcagagc ggaccaggac tggtgaagcc ctcccagacc    480
ctgtctctga catgtgccat cagcggcgat tccgtgagct ccaacagcgc cgcctggaat    540
tggatccggc agtctcccag cagaggactg gagtggctgg aaggacctac ctatcgctcc    600
aagtggtaca cgattatgc cgtgtctgtg aagagccgga tcaccatcaa ccctgacaca    660
tctaagaatc agttcagcct gcagctgaat tccgtgaccc cagaggacac agccgtgtac    720
tattgtgcaa gggaggtgac cggcgacctg gaggatgcct ttgacatctg gggccagggc    780
accatggtga cagtgtctag caccacgacg ccagcgccgc gaccaccaac accggcgccc    840
accatcgcgt cgcagcccct gtccctgcgc ccagaggcgt gccggccagc ggcggggggc    900
gcagtgcaca cgagggggct ggacttcgcc tgtgatatct acatctgggc gcccttggcc    960
gggacttgtg gggtccttct cctgtcactg gttatcaccc tttactgcaa acggggcaga    1020
aagaaactcc tgtatatatt caaacaacca tttatgagac cagtacaaac tactcaagag    1080
gaagatggct gtagctgccg atttccagaa gaagaagaag aggatgtga actgagagtg    1140 aagttcagca ggagcgcaga cgccccccgcg tacaagcagg ccagaaccca gctctataac    1200
```

| | |
|---|---|
| gagctcaatc taggacgaag agaggagtac gatgttttgg acaagaggcg tggccgggac | 1260 |
| cctgagatgg ggggaaagcc gagaaggaag aaccctcagg aaggcctgta caatgaactg | 1320 |
| cagaaagata agatggcgga ggcctacagt gagattggga tgaaaggcga gcgccggagg | 1380 |
| ggcaaggggc acgatggcct ttaccagggt ctcagtacag ccaccaagga cacctacgac | 1440 |
| gcccttcaca tgcaggccct gcccctcgc taatctagag ccacgaactt ctctctgtta | 1500 |
| aagcaagcag gagacgtgga agaaaacccc ggtcctcata tgatggcctt accagtgacc | 1560 |
| gccttgctcc tgccgctggc cttgctgctc cacgccgcca ggccggacat cgtgatgacc | 1620 |
| cagtccccct ccagcctgac agtgacagcc ggcgagaagg tgacaatgat ctgtaagtcc | 1680 |
| agccagagcc tgctgaacag cggcgaccag aagaactacc tgacctggta ccagcagaag | 1740 |
| cctggccagc cccccaagct gctgatcttc tgggccagca aagggagag cggcgtgccc | 1800 |
| gacagattca caggcagcgg cagcggcacc gacttcacac tgaccatttc ctccgtgcag | 1860 |
| gccgaggacc tcgccgtgta ctactgccag aacgactact cctacccct gacattcggc | 1920 |
| gccggcacca aactggagct gaaggtggc ggtggctcgg gcgtggtgg gtcgggtggc | 1980 |
| ggcggatctc aggtgcagct ccagcagtcc gatgccgagc tggtgaagcc cggaagcagc | 2040 |
| gtcaagatca gctgtaaggc ctccggctac accttcacag accacgccat ccactgggtg | 2100 |
| aagcagaagc ccgagcaggg cctggagtgg atcggccact ttagccccgg aaacaccgac | 2160 |
| atcaagtaca cgacaagtt caagggcaag gccacctga ccgtggacag gagcagcagc | 2220 |
| accgcctaca tgcagctgaa cagcctgaca agcgaggaca gcgccgtgta cttctgcaag | 2280 |
| acctccacct tcttcttcga ctactggggc cagggaacca ccctgacagt gtccagcacc | 2340 |
| acgacgccag cgccgcgacc accaacaccg gcgcccacca tcgcgtcgca gccctgtcc | 2400 |
| ctgcgcccag aggcgtgccg gccagcggcg ggggcgcag tgcacacgag ggggctggac | 2460 |
| ttcgcctgtg atatctacat ctgggcgccc ttggccggga cttgtggggt ccttctcctg | 2520 |
| tcactggtta tcacccttta ctgcaaacgg ggcagaaaga aactcctgta tatattcaaa | 2580 |
| caaccattta tgagaccagt acaaactact caagaggaag atggctgtag ctgccgatt | 2640 |
| ccagaagaag aagaaggagg atgtgaactg agagtgaagt tcagcaggag cgcagacgcc | 2700 |
| cccgcgtaca gcagggcca gaaccagctc tataacgagc tcaatctagg acgaagagag | 2760 |
| gagtacgatg ttttggacaa gaggcgtggc cgggaccctg agatgggggg aaagccgaga | 2820 |
| aggaagaacc ctcaggaagg cctgtacaat gaactgcaga agataagat ggcggaggcc | 2880 |
| tacagtgaga ttgggatgaa aggcgagcgc cggaggggca aggggcacga tggcctttac | 2940 |
| cagggtctca gtacagccac caaggacacc tacgacgccc ttcacatgca ggccctgccc | 3000 |
| cctcgctaa | 3009 |

<210> SEQ ID NO 29
<211> LENGTH: 2982
<212> TYPE: DNA
<213> ORGANISM: Artificial Sequence
<220> FEATURE:
<223> OTHER INFORMATION: Synthesized

<400> SEQUENCE: 29

| | |
|---|---|
| atggccttac cagtgaccgc cttgctcctg ccgctggcct tgctgctcca cgccgccagg | 60 |
| ccggacatcc agctcaccca gtccccgagc tcgctgtccg cctccgtggg agatcgggtc | 120 |
| accatcacgt gccgcgccag ccagtcgatt tcctcctacc tgaactggta ccaacagaag | 180 |
| cccggaaaag ccccgaagct tctcatctac gccgcctcga gcctgcagtc aggagtgccc | 240 |

```
tcacggttct ccggctccgg ttccggtact gatttcaccc tgaccatttc ctccctgcaa      300
ccggaggact tcgctactta ctactgccag cagtcgtact ccacccccta cactttcgga      360
caaggcacca aggtcgaaat caagggtggc ggtggctcgg gcggtggtgg gtcgggtggc      420
ggcggatctg aagtgcaatt ggtggaatca ggggggaggac ttgtgcagcc tggaggatcg      480
```

```
ctgagactgt catgtgccgt gtccggcttt gccctgtcca accacgggat gtcctgggtc      540
cgccgcgcgc ctggaaaggg cctcgaatgg gtgtcgggta ttgtgtacag cggtagcacc      600
tactatgccg catccgtgaa ggggagattc accatcagcc gggacaactc caggaacact      660
ctgtacctcc aaatgaattc gctgaggcca gaggacactg ccatctacta ctgctccgcg      720
catggcggag agtccgacgt ctggggacag gggaccaccg tgaccgtgtc tagcaccacg      780
acgccagcgc cgcgaccacc aacaccggcg cccaccatcg cgtcgcagcc cctgtccctg      840
cgcccagagg cgtgccggcc agcggcgggg ggcgcagtgc acacgagggg gctggacttc      900
gcctgtgata tctacatctg ggcgcccttg gccgggactt gtgggtcct  tctcctgtca      960 ctggttatca ccctttactg caaacggggc agaagaaaac tcctgtatat attcaaacaa     1020
ccatttatga gaccagtaca aactactcaa gaggaagatg ctgtagctg  ccgatttcca     1080 gaagaagaag aaggaggatg tgaactgaga gtgaagttca gcaggagcgc agacgccccc     1140
gcgtacaagc agggccagaa ccagctctat aacgagctca atctaggacg aagagaggag     1200
tacgatgttt tggacaagag gcgtggccgg gaccctgaga tgggggaaa  gccgagaagg     1260 aagaaccctc aggaaggcct gtacaatgaa ctgcagaaag ataagatggc ggaggcctac     1320
agtgagattg ggatgaaagg cgagcgccgg aggggcaagg ggcacgatgg cctttaccag     1380
ggtctcagta cagccaccaa ggacacctac gacgcccttc acatgcaggc cctgcccccct     1440 cgctaatcta gagccacgaa cttctctctg ttaaagcaag caggagacgt ggaagaaaac     1500
cccggtcctc atatgatggc cttaccagtg accgccttgc tcctgccgct ggccttgctg     1560
ctccacgccg ccaggccgga catcgtgatg acccagtccc cctccagcct gacagtgaca     1620
gccggcgaga aggtgacaat gatctgtaag tccagccaga gcctgctgaa cagcggcgac     1680
cagaagaact acctgacctg gtaccagcag aagcctggcc agccccccaa gctgctgatc     1740
ttctgggcca gcacaaggga gagcggcgtg cccgacagat tcacaggcag cggcagcggc     1800
accgacttca cactgaccat ttcctccgtg caggccgagg acctcgccgt gtactactgc     1860
cagaacgact actcctaccc cctgacattc ggcgccggca ccaaactgga gctgaagggt     1920
ggcggtggct cgggcggtgg tgggtcgggt ggcggcggat ctcaggtgca gctccagcag     1980
tccgatgccg agctggtgaa gcccggaagc agcgtcaaga tcagctgtaa ggcctccggc     2040
tacaccttca cagaccacgc catccactgg gtgaagcaga gcccgagca  gggcctggag     2100 tggatcggcc actttagccc cggaaacacc gacatcaagt acaacgacaa gttcaagggc     2160
aaggccaccc tgaccgtgga caggagcagc agcaccgcct acatgcagct gaacagcctg     2220
acaagcgagg acagcgccgt gtacttctgc aagacctcca ccttcttctt cgactactgg     2280
ggccagggaa ccaccctgac agtgtccagc accacgacgc cagcgccgcg accaccaaca     2340
ccggcgccca ccatcgcgtc gcagcccctg tcctgcgcc  cagaggcgtg ccggccagcg     2400
gcggggggcg cagtgcacac gagggggctg gacttcgcct gtgatatcta catctgggcg     2460
cccttggccg ggacttgtgg ggtccttctc ctgtcactgg ttatcaccct ttactgcaaa     2520
cggggcagaa agaaactcct gtatatattc aaacaaccat ttatgagacc agtacaaact     2580
```

```
actcaagagg aagatggctg tagctgccga tttccagaag aagaagaagg aggatgtgaa    2640
ctgagagtga agttcagcag gagcgcagac gcccccgcgt acaagcaggg ccagaaccag    2700
ctctataacg agctcaatct aggacgaaga gaggagtacg atgttttgga caagaggcgt    2760
ggccgggacc ctgagatggg gggaaagccg agaaggaaga accctcagga aggcctgtac    2820
aatgaactgc agaaagataa gatggcggag gcctacagtg agattgggat gaaaggcgag    2880
cgccggaggg gcaaggggca cgatggcctt taccagggtc tcagtacagc caccaaggac    2940
acctacgacg cccttcacat gcaggccctg ccccctcgct aa                      2982
```

<210> SEQ ID NO 30
<211> LENGTH: 244
<212> TYPE: PRT
<213> ORGANISM: Artificial Sequence
<220> FEATURE:
<223> OTHER INFORMATION: Synthesized

<400> SEQUENCE: 30

Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Gln Val Gln Leu Gln Gln Ser Asp Ala Glu Leu Val Lys Pro Gly Ser
    130                 135                 140

Ser Val Lys Ile Ser Cys Lys Ala Ser Gly Tyr Thr Phe Thr Asp His
145                 150                 155                 160

Ala Ile His Trp Val Lys Gln Lys Pro Glu Gln Gly Leu Glu Trp Ile
                165                 170                 175

Gly His Phe Ser Pro Gly Asn Thr Asp Ile Lys Tyr Asn Asp Lys Phe
            180                 185                 190

Lys Gly Lys Ala Thr Leu Thr Val Asp Arg Ser Ser Ser Thr Ala Tyr
        195                 200                 205

Met Gln Leu Asn Ser Leu Thr Ser Glu Asp Ser Ala Val Tyr Phe Cys
    210                 215                 220

Lys Thr Ser Thr Phe Phe Phe Asp Tyr Trp Gly Gln Gly Thr Thr Leu
225                 230                 235                 240

Thr Val Ser Ser

<210> SEQ ID NO 31
<211> LENGTH: 116
<212> TYPE: PRT
<213> ORGANISM: Artificial Sequence
<220> FEATURE:
<223> OTHER INFORMATION: Synthesized

<400> SEQUENCE: 31

Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Thr Ser Thr Phe Phe Phe Asp Tyr Trp Gly Gln Gly Thr Thr Leu
            100                 105                 110

Thr Val Ser Ser
        115

<210> SEQ ID NO 32
<211> LENGTH: 113
<212> TYPE: PRT
<213> ORGANISM: Artificial Sequence
<220> FEATURE:
<223> OTHER INFORMATION: Synthesized

<400> SEQUENCE: 32

Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 33
<211> LENGTH: 246
<212> TYPE: PRT
<213> ORGANISM: Artificial Sequence
<220> FEATURE:
<223> OTHER INFORMATION: Synthesized

<400> SEQUENCE: 33

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro

```
                    50                  55                  60
Asp Arg Phe Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Pro Thr Phe Gly Gly Gly Thr Lys Leu Glu Ile Lys
            100                 105                 110

Arg Ala Gly Gly Gly Ser Gly Gly Gly Ser Gly Gly Gly Gly
        115                 120                 125

Ser Glu Val Lys Leu Val Glu Ser Gly Gly Leu Val Gln Pro Gly
    130                 135                 140

Gly Ser Met Lys Leu Ser Cys Val Ala Ser Gly Phe Thr Phe Ser Asn
145                 150                 155                 160

Tyr Trp Met Asn Trp Val Arg Gln Ser Pro Glu Lys Gly Leu Glu Trp
                165                 170                 175

Val Ala Glu Ile Arg Leu Lys Ser Asn Asn Tyr Thr Thr His Tyr Ala
            180                 185                 190

Glu Ser Val Lys Gly Arg Phe Thr Ile Ser Arg Asp Asp Ser Lys Ser
        195                 200                 205

Ser Val Ser Leu Gln Met Asn Asn Leu Arg Val Glu Asp Thr Gly Ile
    210                 215                 220

Tyr Tyr Cys Thr Arg His Tyr Tyr Phe Asp Tyr Trp Gly Gln Gly Thr
225                 230                 235                 240

Thr Leu Thr Val Ser Ser
                245

<210> SEQ ID NO 34
<211> LENGTH: 117
<212> TYPE: PRT
<213> ORGANISM: Artificial Sequence
<220> FEATURE:
<223> OTHER INFORMATION: Synthesized

<400> SEQUENCE: 34

Glu Val Lys Leu Val Glu Ser Gly Gly Leu Val Gln Pro Gly Gly
 1                5                  10                  15

Ser Met Lys Leu Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
             35                  40                  45

Ala Glu Ile Arg Leu Lys Ser Asn Asn Tyr Thr Thr His Tyr Ala Glu
         50                  55                  60

Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
            100                 105                 110

Leu Thr Val Ser Ser
        115

<210> SEQ ID NO 35
<211> LENGTH: 114
<212> TYPE: PRT
<213> ORGANISM: Artificial Sequence
<220> FEATURE:
<223> OTHER INFORMATION: Synthesized
```

<400> SEQUENCE: 35

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Ala

<210> SEQ ID NO 36
<211> LENGTH: 97
<212> TYPE: PRT
<213> ORGANISM: Artificial Sequence
<220> FEATURE:
<223> OTHER INFORMATION: Synthesized

<400> SEQUENCE: 36

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Ala
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Ala Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu

<210> SEQ ID NO 37
<211> LENGTH: 288
<212> TYPE: PRT
<213> ORGANISM: Artificial Sequence
<220> FEATURE:
<223> OTHER INFORMATION: Synthesized

<400> SEQUENCE: 37

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala

```
                65                  70                  75                  80
Ala Phe Pro Glu Asp Arg Ser Gln Pro Gly Gln Asp Cys Arg Phe Arg
                    85                  90                  95

Val Thr Gln Leu Pro Asn Gly Arg Asp Phe His Met Ser Val Val Arg
                    100                 105                 110

Ala Arg Arg Asn Asp Ser Gly Thr Tyr Leu Cys Gly Ala Ile Ser Leu
                    115                 120                 125

Ala Pro Lys Ala Gln Ile Lys Glu Ser Leu Arg Ala Glu Leu Arg Val
                    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
                    180                 185                 190

Ser Arg Ala Ala Arg Gly Thr Ile Gly Ala Arg Arg Thr Gly Gln Pro
                    195                 200                 205

Leu Lys Glu Asp Pro Ser Ala Val Pro Val Phe Ser Val Asp Ala Gly
                    210                 215                 220

Glu Leu Asp Phe Gln Trp Arg Glu Lys Thr Pro Glu Pro Pro Val Pro
225                 230                 235                 240

Cys Val Pro Glu Gln Thr Glu Ala Ala Thr Ile Val Phe Pro Ser Gly
                    245                 250                 255

Met Gly Thr Ser Ser Pro Ala Arg Arg Gly Ser Ala Asp Gly Pro Arg
                    260                 265                 270

Ser Ala Gln Pro Leu Arg Pro Glu Asp Gly His Cys Ser Trp Pro Leu
                    275                 280                 285

<210> SEQ ID NO 38
<211> LENGTH: 17
<212> TYPE: PRT
<213> ORGANISM: Artificial Sequence
<220> FEATURE:
<223> OTHER INFORMATION: Synthesized

<400> SEQUENCE: 38

Cys Ser Arg Ala Ala Arg Gly Thr Ile Asp Gly His Cys Ser Trp Pro
1               5                   10                  15

Leu

<210> SEQ ID NO 39
<211> LENGTH: 21
<212> TYPE: PRT
<213> ORGANISM: Artificial Sequence
<220> FEATURE:
<223> OTHER INFORMATION: Synthesized

<400> SEQUENCE: 39

Val Gly Val Val Gly Gly Leu Leu Gly Ser Leu Val Leu Leu Val Trp
1               5                   10                  15

Val Leu Ala Val Ile
                20

<210> SEQ ID NO 40
<211> LENGTH: 18
<212> TYPE: PRT
<213> ORGANISM: Artificial Sequence
<220> FEATURE:
<223> OTHER INFORMATION: Synthesized
```

```
<400> SEQUENCE: 40

Gly Asn Ile Leu Asn Val Ser Ile Lys Ile Cys Leu Thr Leu Ser Pro
1               5                   10                  15

Ser Thr

<210> SEQ ID NO 41
<211> LENGTH: 9
<212> TYPE: PRT
<213> ORGANISM: Artificial Sequence
<220> FEATURE:
<223> OTHER INFORMATION: Synthesized

<400> SEQUENCE: 41

Cys Ser Arg Ala Ala Arg Gly Thr Ile
1               5

<210> SEQ ID NO 42
<211> LENGTH: 80
<212> TYPE: PRT
<213> ORGANISM: Artificial Sequence
<220> FEATURE:
<223> OTHER INFORMATION: Synthesized

<400> SEQUENCE: 42

Gly Ala Arg Arg Thr Gly Gln Pro Leu Lys Glu Asp Pro Ser Ala Val
1               5                   10                  15

Pro Val Phe Ser Val Asp Tyr Gly Glu Leu Asp Phe Gln Trp Arg Glu
                20                  25                  30

Lys Thr Pro Glu Pro Pro Val Pro Cys Val Pro Glu Gln Thr Glu Tyr
            35                  40                  45

Ala Thr Ile Val Phe Pro Ser Gly Met Gly Thr Ser Ser Pro Ala Arg
        50                  55                  60

Arg Gly Ser Ala Asp Gly Pro Arg Ser Ala Gln Pro Leu Arg Pro Glu
65                  70                  75                  80

<210> SEQ ID NO 43
<211> LENGTH: 69
<212> TYPE: PRT
<213> ORGANISM: Artificial Sequence
<220> FEATURE:
<223> OTHER INFORMATION: Synthesized

<400> SEQUENCE: 43

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 44
<211> LENGTH: 223
<212> TYPE: PRT
<213> ORGANISM: Homo sapiens

<400> SEQUENCE: 44
```

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
            165                 170                 175

Tyr Ser Phe Leu Leu Thr Ala Val Ser Leu Ser Lys Met Leu Lys Lys
        180                 185                 190

Arg Ser Pro Leu Thr Thr Gly Val Tyr Val Lys Met Pro Pro Thr Glu
    195                 200                 205

Pro Glu Cys Glu Lys Gln Phe Gln Pro Tyr Phe Ile Pro Ile Asn
210                 215                 220
```

<210> SEQ ID NO 45
<211> LENGTH: 223
<212> TYPE: PRT
<213> ORGANISM: Artificial Sequence
<220> FEATURE:
<223> OTHER INFORMATION: Synthesized

<400> SEQUENCE: 45

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140
```

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Phe Val Lys Met Pro Thr Glu
                195                 200                 205

Pro Glu Cys Glu Lys Gln Phe Gln Pro Tyr Phe Ile Pro Ile Asn
    210                 215                 220

<210> SEQ ID NO 46
<211> LENGTH: 223
<212> TYPE: PRT
<213> ORGANISM: Artificial Sequence
<220> FEATURE:
<223> OTHER INFORMATION: Synthesized

<400> SEQUENCE: 46

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
                115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Phe Phe Ile Pro Ile Asn
    210                 215                 220

<210> SEQ ID NO 47
<211> LENGTH: 223
<212> TYPE: PRT
<213> ORGANISM: Artificial Sequence
<220> FEATURE:
<223> OTHER INFORMATION: Synthesized

<400> SEQUENCE: 47

Met Ala Cys Leu Gly Phe Gln Arg His Lys Ala Gln Leu Asn Leu Ala
1               5                   10                  15

```
Thr Arg Thr Trp Pro Cys Thr Leu Leu Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Phe Val Lys Met Pro Pro Thr Glu
        195                 200                 205

Pro Glu Cys Glu Lys Gln Phe Gln Pro Phe Phe Ile Pro Ile Asn
    210                 215                 220

<210> SEQ ID NO 48
<211> LENGTH: 189
<212> TYPE: PRT
<213> ORGANISM: Artificial Sequence
<220> FEATURE:
<223> OTHER INFORMATION: Synthesized

<400> SEQUENCE: 48

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160
```

```
Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met
            180                 185

<210> SEQ ID NO 49
<211> LENGTH: 240
<212> TYPE: PRT
<213> ORGANISM: Artificial Sequence
<220> FEATURE:
<223> OTHER INFORMATION: Synthesized

<400> SEQUENCE: 49

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Ala Ala Ala Pro Thr Thr Thr Pro Ala Pro Arg Pro Pro Thr Pro
                165                 170                 175

Ala Pro Thr Ile Ala Ser Gln Pro Leu Ser Leu Arg Pro Glu Ala Cys
            180                 185                 190

Arg Pro Ala Ala Gly Gly Ala Val His Thr Arg Gly Leu Asp Phe Ala
        195                 200                 205

Cys Asp Ile Tyr Ile Trp Ala Pro Leu Ala Gly Thr Cys Gly Val Leu
    210                 215                 220

Leu Leu Ser Leu Val Ile Thr Leu Tyr Cys Asn His Arg Arg Ile Gln
225                 230                 235                 240

<210> SEQ ID NO 50
<211> LENGTH: 223
<212> TYPE: PRT
<213> ORGANISM: Artificial Sequence
<220> FEATURE:
<223> OTHER INFORMATION: Synthesized

<400> SEQUENCE: 50

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
```

```
                    35                  40                  45

Ser Ser Arg Gly Ile Ala Ser Phe Val Cys Glu Tyr Ala Ser Pro Gly
 50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                 85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Ala Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Phe Val Lys Met Pro Pro Thr Glu
            195                 200                 205

Pro Glu Cys Glu Lys Gln Phe Gln Pro Phe Phe Ile Pro Ile Asn
210                 215                 220

<210> SEQ ID NO 51
<211> LENGTH: 189
<212> TYPE: PRT
<213> ORGANISM: Artificial Sequence
<220> FEATURE:
<223> OTHER INFORMATION: Synthesized

<400> SEQUENCE: 51

Met Ala Cys Leu Gly Phe Gln Arg His Lys Ala Gln Leu Asn Leu Ala
 1               5                  10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
             35                  40                  45

Ser Ser Arg Gly Ile Ala Ser Phe Val Cys Glu Tyr Ala Ser Pro Gly
 50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                 85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Ala Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met
```

180                 185

<210> SEQ ID NO 52
<211> LENGTH: 240
<212> TYPE: PRT
<213> ORGANISM: Artificial Sequence
<220> FEATURE:
<223> OTHER INFORMATION: Synthesized

<400> SEQUENCE: 52

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Ala Gly Ile Gly
    130                 135                 140

Asn Gly Thr Gln Ile Tyr Val Ile Asp Pro Glu Pro Cys Pro Asp Ser
145                 150                 155                 160

Asp Ala Ala Ala Pro Thr Thr Thr Pro Ala Pro Arg Pro Pro Thr Pro
                165                 170                 175

Ala Pro Thr Ile Ala Ser Gln Pro Leu Ser Leu Arg Pro Glu Ala Cys
            180                 185                 190

Arg Pro Ala Ala Gly Gly Ala Val His Thr Arg Gly Leu Asp Phe Ala
        195                 200                 205

Cys Asp Ile Tyr Ile Trp Ala Pro Leu Ala Gly Thr Cys Gly Val Leu
    210                 215                 220

Leu Leu Ser Leu Val Ile Thr Leu Tyr Cys Asn His Arg Arg Ile Gln
225                 230                 235                 240

<210> SEQ ID NO 53
<211> LENGTH: 112
<212> TYPE: PRT
<213> ORGANISM: Homo sapiens

<400> SEQUENCE: 53

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 54
<211> LENGTH: 288
<212> TYPE: PRT
<213> ORGANISM: Homo sapiens

<400> SEQUENCE: 54

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 55
<211> LENGTH: 288
<212> TYPE: PRT
<213> ORGANISM: Artificial Sequence
<220> FEATURE:
<223> OTHER INFORMATION: Synthesized

<400> SEQUENCE: 55

```
Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Ser Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285
```

<210> SEQ ID NO 56
<211> LENGTH: 288
<212> TYPE: PRT
<213> ORGANISM: Artificial Sequence
<220> FEATURE:
<223> OTHER INFORMATION: Synthesized

<400> SEQUENCE: 56

```
Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
    50                  55                  60

Leu Asn Trp Tyr Arg Ile Ser Pro Ser Asn Gln Thr Asp Lys Leu Ala
65                  70                  75                  80
```

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Ser Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 57
<211> LENGTH: 288
<212> TYPE: PRT
<213> ORGANISM: Artificial Sequence
<220> FEATURE:
<223> OTHER INFORMATION: Synthesized

<400> SEQUENCE: 57

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Val Lys Leu Ala
65                  70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Ser Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 58
<211> LENGTH: 513
<212> TYPE: DNA
<213> ORGANISM: Artificial Sequence
<220> FEATURE:
<223> OTHER INFORMATION: Synthesized

<400> SEQUENCE: 58

| | | |
|---|---|---|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc caacacatcg | 180 |
| gagagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcagggccc ggcgcaatga cagcggcacc | 360 |
| tacctctgtg gggccatctc cctggccccc aaggcgcaga tcaaagagag cctgcgggca | 420 |
| gagctcaggg tgacagagag aagggcagaa gtgcccacag cccaccccag cccctcaccc | 480 |
| aggccagccg gccagttcca aaccctggtg tga | 513 |

<210> SEQ ID NO 59
<211> LENGTH: 717
<212> TYPE: DNA
<213> ORGANISM: Artificial Sequence
<220> FEATURE:
<223> OTHER INFORMATION: Synthesized

<400> SEQUENCE: 59

| | | |
|---|---|---|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc caacacatcg | 180 |
| gagagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcagggccc ggcgcaatga cagcggcacc | 360 |
| tacctctgtg gggccatctc cctggccccc aaggcgcaga tcaaagagag cctgcgggca | 420 |
| gagctcaggg tgacagagag aagggcagaa gtgcccacag cccaccccag cccctcaccc | 480 |
| aggccagccg gccagttcca aaccctggtg ttttgggtgc tggtggtggt tggtggagtc | 540 |

```
ctggcttgct atagcttgct agtaacagtg gcctttatta ttttctgggt gaggagtaag    600
aggagcaggc tcctgcacag tgactacatg aacatgactc cccgccgccc gggcccacc    660 cgcaagcatt accagcccta tgccccacca cgcgacttcg cagcctatcg ctcctga      717
```

<210> SEQ ID NO 60
<211> LENGTH: 237
<212> TYPE: DNA
<213> ORGANISM: Artificial Sequence
<220> FEATURE:
<223> OTHER INFORMATION: Synthesized

<400> SEQUENCE: 60

```
cggctccggt gcccgtcagt gggcagagcg cacatcgccc acagtccccg agaagttggg    60
gggaggggtc ggcaattgaa ccggtgccta gagaaggtgg cgcggggtaa actgggaaag   120
tgatgtcgtg tactggctcc gccttttttcc cgagggtggg ggagaaccgt atataagtgc   180
agtagtcgcc gtgaacgttc tttttcgcaa cgggtttgcc gccagaacac aggatcc      237
```

<210> SEQ ID NO 61
<211> LENGTH: 1008
<212> TYPE: DNA
<213> ORGANISM: Artificial Sequence
<220> FEATURE:
<223> OTHER INFORMATION: Synthesized

<400> SEQUENCE: 61

```
atgtctagat tagataaaag taaagtgatt aacagcgcat tagagctgct taatgaggtc    60
ggaatcgaag gtttaacaac ccgtaaactc gcccagaagc ttggtgtaga gcagcctaca   120
ctgtattggc atgtaaaaaa taagcgggct ttgctcgacg ccttagccat tgagatgtta   180
gataggcacc atactcactt tgcccttta aaaggggaaa gctggcaaga ttttttacgc    240
aataacgcta aaagttttag atgtgcttta ctaagtcatc gcaatggagc aaaagtacat   300
tcagatacac ggcctacaga aaaacagtat gaaactctcg aaaatcaatt agccttttta   360
tgccaacaag ttttttcact agagaacgcg ttatatgcac tcagcgctgt ggggcatttt   420
actttaggtt gcgtattgga agatcaagag catcaagtcg ctaaagaaga aagggaaaca   480
cctactactg atagtatgcc gccattatta cgacaagcta tcgaattatt tgatcaccaa   540
ggtgcagagc cagccttctt attcggcctt gaattgatca tatgcggatt agaaaaacaa   600
cttaaatgtg aaagtgggtc cgcgtacagc cgcgcgcgta cgaaaaacaa ttacgggtct   660
accatcgagg gcctgctcga tctcccggac gacgacgccc ccgaagaggc ggggctggcg   720
gctccgcgcc tgtcctttct ccccgcggga cacacgcgca gactgtcgac ggccccccccg   780 accgatgtca gctgggggga cgagctccac ttagacggcg aggacgtggc gatggcgcat   840
gccgacgcgc tagacgattt cgatctggac atgttggggg acggggattc cccgggtccg   900
ggatttaccc cccacgactc cgcccccctac ggcgctctgg atatggccga cttcgagttt   960
gagcagatgt ttaccgatgc ccttggaatt gacgagtacg gtgggtag              1008
```

<210> SEQ ID NO 62
<211> LENGTH: 438
<212> TYPE: DNA
<213> ORGANISM: Artificial Sequence
<220> FEATURE:
<223> OTHER INFORMATION: Synthesized

<400> SEQUENCE: 62

```
ctcgagttta ccactcccta tcagtgatag agaaaagtga agtcgagtt taccactccc    60 tatcagtgat agagaaaagt gaaagtcgag tttaccactc cctatcagtg atagagaaaa   120
gtgaaagtcg agtttaccac tccctatcag tgatagagaa aagtgaaagt cgagtttacc   180
actccctatc agtgatagag aaaagtgaaa gtcgagttta ccactcccta tcagtgatag   240
agaaaagtga agtcgagtt taccactccc tatcagtgat agagaaaagt gaaagtcgag   300
ctcggtaccc gggtcgagta ggcgtgtacg gtgggaggcc tatataagca gagctcgttt   360
agtgaaccgt cagatcgcct ggagacgcca tccacgctgt tttgacctcc atagaagaca   420
ccgggaccga tccagcct                                                 438
```

<210> SEQ ID NO 63
<211> LENGTH: 1178
<212> TYPE: DNA
<213> ORGANISM: Artificial Sequence
<220> FEATURE:
<223> OTHER INFORMATION: Synthesized
<400> SEQUENCE: 63

```
ggctccggtg cccgtcagtg ggcagagcgc acatcgccca cagtccccga gaagttgggg    60
ggaggggtcg gcaattgaac cggtgcctag agaaggtggc gcggggtaaa ctgggaaagt   120
gatgtcgtgt actggctccg ccttttcc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acgggttatg gcccttgcgt gccttgaatt   300
acttccactg gctgcagtac gtgattcttg atcccgagct tcgggttgga agtgggtggg   360
agagttcgag gccttgcgct taaggagccc cttcgcctcg tgcttgagtt gaggcctggc   420
ctgggcgctg ggccgccgc gtgcgaatct ggtggcacct tcgcgcctgt ctcgctgctt   480
tcgataagtc tctagccatt taaaattttt gatgacctgc tgcgacgctt ttttctggc    540 aagatagtct tgtaaatgcg ggccaagatc tgcacactgg tatttcggtt tttggggccg   600
cgggcggcga cggggcccgt gcgtcccagc gcacatgttc ggcgaggcgg ggcctgcgag   660
cgcggccacc gagaatcgga cggggtagt ctcaagctgg ccggcctgct ctggtgcctg   720
gcctcgcgcc gccgtgtatc gccccgccct gggcggcaag gctggcccgg tcggcaccag   780
ttgcgtgagc ggaaagatgg ccgcttcccg gccctgctgc agggagctca aaatggagga   840
cgcggcgctc gggagagcgg gcgggtgagt cacccacaca aaggaaaagg gcctttccgt   900
cctcagccgt cgcttcatgt gactccacgg agtaccgggc gccgtccagg cacctcgatt   960
agttctcgag cttttggagt acgtcgtctt taggttgggg ggaggggttt tatgcgatgg  1020 agtttccca cactgagtgg gtggagactg aagttaggcc agcttggcac ttgatgtaat  1080
tctccttgga atttgccctt tttgagtttg gatcttggtt cattctcaag cctcagacag  1140
tggttcaaag ttttttcttt ccatttcagg tgtcgtga                          1178
```

<210> SEQ ID NO 64
<211> LENGTH: 365
<212> TYPE: PRT
<213> ORGANISM: Artificial Sequence
<220> FEATURE:
<223> OTHER INFORMATION: Synthesized
<400> SEQUENCE: 64

```
Pro Gly Trp Phe Leu Asp Ser Pro Asp Arg Pro Trp Asn Pro Pro Thr
  1               5                  10                  15
```

```
Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
         35                  40                  45

Arg Met Ser Pro Ser Asn Gln Thr Asp Lys Leu Ala Ala Phe Pro Glu
     50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
                180                 185                 190

Pro Ser Ala Val Pro Val Phe Ser Val Asp Tyr Gly Glu Leu Asp Phe
            195                 200                 205

Gln Trp Arg Glu Lys Thr Pro Glu Pro Pro Val Pro Cys Val Pro Glu
210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu Cys Ser Arg Ala
            260                 265                 270

Ala Arg Gly Thr Ile Gly Ala Arg Arg Thr Gly Gln Pro Leu Lys Glu
            275                 280                 285

Asp Pro Ser Ala Val Pro Val Phe Ser Val Asp Tyr Gly Glu Leu Asp
            290                 295                 300

Phe Gln Trp Arg Glu Lys Thr Pro Glu Pro Pro Val Pro Cys Val Pro
305                 310                 315                 320

Glu Gln Thr Glu Tyr Ala Thr Ile Val Phe Pro Ser Gly Met Gly Thr
                325                 330                 335

Ser Ser Pro Ala Arg Arg Gly Ser Ala Asp Gly Pro Arg Ser Ala Gln
            340                 345                 350

Pro Leu Arg Pro Glu Asp Gly His Cys Ser Trp Pro Leu
            355                 360                 365

<210> SEQ ID NO 65
<211> LENGTH: 271
<212> TYPE: PRT
<213> ORGANISM: Artificial Sequence
<220> FEATURE:
<223> OTHER INFORMATION: Synthesized

<400> SEQUENCE: 65

Thr Val Thr Val Pro Lys Asp Leu Tyr Val Val Glu Tyr Gly Ser Asn
1               5                   10                  15
```

Met Thr Ile Glu Cys Lys Phe Pro Val Glu Lys Gln Leu Asp Leu Ala
        20                  25                  30

Ala Leu Ile Val Tyr Trp Glu Met Glu Asp Lys Asn Ile Ile Gln Phe
            35                  40                  45

Val His Gly Glu Glu Asp Leu Lys Val Gln His Ser Ser Tyr Arg Gln
        50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125

Thr Ser Glu His Glu Leu Thr Cys Gln Ala Glu Gly Tyr Pro Lys Ala
130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Lys Leu Phe Asn Val Thr Ser
                165                 170                 175

Thr Leu Arg Ile Asn Thr Thr Asn Glu Ile Phe Tyr Cys Thr Phe
            180                 185                 190

Arg Arg Leu Asp Pro Glu Glu Asn His Thr Ala Glu Leu Val Ile Pro
        195                 200                 205

Glu Leu Pro Leu Ala His Pro Pro Asn Glu Arg Thr His Leu Val Ile
    210                 215                 220

Leu Gly Ala Ile Leu Leu Cys Leu Gly Val Ala Leu Thr Phe Ile Phe
225                 230                 235                 240

Arg Leu Arg Lys Gly Arg Met Met Asp Val Lys Lys Cys Gly Ile Gln
                245                 250                 255

Asp Thr Asn Ser Lys Lys Gln Ser Asp Thr His Leu Glu Glu Thr
            260                 265                 270

<210> SEQ ID NO 66
<211> LENGTH: 750
<212> TYPE: DNA
<213> ORGANISM: Homo sapiens

<400> SEQUENCE: 66
gacatcgtga tgacccagtc ccctctgtct ttacccgtta cacccggtga acccgccagc     60
attagctgta ggtccaccaa gtctttactg cacagcaacg gcaacaccta tttatactgg    120
ttcttacaga agcccggcca atccccccag ctgctgatct atcgtatgag caatttagct    180
agcggcgtgc ccgacagatt cagcggcagc ggctccggaa ccgacttcac tttaaagatc    240
tccagagtgg aggccgagga cgtgggcgtt tactactgca tgcagcattt agagtacccc    300
ttcaccttcg gcggcggcac caaggtggag atcaaggggtg cggcggcag cggcggcggt    360 ggcagcggag gcggaggcag cgagatccag ctgcagcaaa gcggcgccga ggtgaaaaag    420
cccggcagca gcgtcaaggt gagctgcaag gccagcggct acaccttcac cgattacgac    480
atgcactggg tgagacaagc tcccggtcaa ggtttagagt ggatcggcac aatcgacccc    540
gagaccggcg gcacagccta caaccagaag tttaagggtc gtgccacttt aacagccgat    600
cgttccacca gcaccgccta catggagctg agctctttaa ggtccgagga caccgctgtg    660
tactattgca ccagcttcta ttacacctac agcaactacg acgtgggctt tgcctactgg    720

```
ggccaaggta ccctcgtgac agtcagcagc                                      750

<210> SEQ ID NO 67
<211> LENGTH: 390
<212> TYPE: DNA
<213> ORGANISM: Artificial Sequence
<220> FEATURE:
<223> OTHER INFORMATION: Synthesized

<400> SEQUENCE: 67
tcgaggtcga cggtatcgat aagcttgata tcgaattagg aggaaaaact gtttcataca     60
gaaggcgtca attaggagga aaaactgttt catacagaag gcgtcaatta ggaggaaaaa    120
ctgtttcata cagaaggcgt caattggtcc catcgaatta ggaggaaaaa ctgtttcata    180
cagaaggcgt caattaggag gaaaaactgt ttcatacaga aggcgtcaat taggaggaaa    240
aactgtttca tacagaaggc gtcaattggt cccgggacat tttgacaccc ccataatatt    300
tttccagaat taacagtata aattgcatct cttgttcaag agttccctat cactctcttt    360
aatcactact cacagtaacc tcaactcctg                                      390

<210> SEQ ID NO 68
<211> LENGTH: 999
<212> TYPE: DNA
<213> ORGANISM: Artificial Sequence
<220> FEATURE:
<223> OTHER INFORMATION: Synthesized

<400> SEQUENCE: 68
tcgaggtcga cggtatcgat aagcttgata tcgaattagg aggaaaaact gtttcataca     60
gaaggcgtca attaggagga aaaactgttt catacagaag gcgtcaatta ggaggaaaaa    120
ctgtttcata cagaaggcgt caattggtcc catcgaatta ggaggaaaaa ctgtttcata    180
cagaaggcgt caattaggag gaaaaactgt ttcatacaga aggcgtcaat taggaggaaa    240
aactgtttca tacagaaggc gtcaattggt cccgggacat tttgacaccc ccataatatt    300
tttccagaat taacagtata aattgcatct cttgttcaag agttccctat cactctcttt    360
aatcactact cacagtaacc tcaactcctg gccaccatgc agatcccaca ggcgccctgg    420
ccagtcgtct gggcggtgct acaactgggc tggcggccag gatggttctt agactcccca    480
gacaggcccc tggaaccccc caccttctcc ccagccctgc tcgtggtgac cgaagggggac   540 aacgccacct tcacctgcag cttctccaac acatcggaga gcttcgtgct aaactggtac    600
cgcatgagcc ccagcaacca gacggacaag ctggccgcct cccccgagga ccgcagccag    660
cccggccagg actgccgctt ccgtgtcaca caactgccca cgggcgtga cttccacatg     720 agcgtggtca gggcccggcg caatgacagc ggcacctacc tctgtggggc catctccctg    780 gccccccaagg cgcagatcaa agagagcctg cgggcagagc tcagggtgac agagagaagg    840
gcagaagtgc ccacagccca ccccagcccc tcacccaggc cagccggcca gttccaaacc    900
ctggtggttg gtgtcgtggg cggcctgctg ggcagcctgg tgctgctagt ctgggtcctg    960
gccgtcatct gctcccgggc cgcacgaggg acaatataa                            999

<210> SEQ ID NO 69
<211> LENGTH: 1263
<212> TYPE: DNA
<213> ORGANISM: Artificial Sequence
<220> FEATURE:
<223> OTHER INFORMATION: Synthesized
```

<400> SEQUENCE: 69

```
tcgaggtcga cggtatcgat aagcttgata tcgaattagg aggaaaaact gtttcataca      60
gaaggcgtca attaggagga aaaactgttt catacagaag gcgtcaatta ggaggaaaaa     120
ctgtttcata cagaaggcgt caattggtcc catcgaatta ggaggaaaaa ctgtttcata     180
cagaaggcgt caattaggag gaaaaactgt ttcatacaga aggcgtcaat taggaggaaa     240
aactgtttca tacagaaggc gtcaattggt cccgggacat tttgacaccc ccataatatt     300
tttccagaat taacagtata aattgcatct cttgttcaag agttccctat cactctcttt     360
aatcactact cacagtaacc tcaactcctg gccaccatgc agatcccaca ggcgccctgg     420
ccagtcgtct gggcggtgct acaactgggc tggcggccag gatggttctt agactcccca     480
gacaggccct ggaacccccc caccttctcc ccagccctgc tcgtggtgac cgaaggggac     540
aacgccacct tcacctgcag cttctccaac acatcggaga gcttcgtgct aaactggtac     600
cgcatgagcc ccagcaacca gacgacaaag ctggccgcct tccccgagga ccgcagccag     660
cccggccagg actgccgctt ccgtgtcaca caactgccca cgggcgtgac cttccacatg     720
agcgtggtca gggcccggcg caatgacagc ggcacctacc tctgtggggc catctccctg     780
gcccccaagg cgcagatcaa agagagcctg cgggcagagc tcagggtgac agagagaagg     840
gcagaagtgc ccacagccca ccccagcccc tcacccaggc cagccggcca gttccaaacc     900
ctggtggttg gtgtcgtggg cggcctgctg ggcagcctgg tgctgctagt ctgggtcctg     960
gccgtcatct gctcccgggc cgcacgaggg acaataggag ccaggcgcac cggccagccc    1020
ctgaaggagg acccctcagc cgtgcctgtg ttctctgtgg acgccgggga gctggatttc    1080
cagtggcgag agaagacccc ggagcccccc gtgccctgtg tccctgagca acggaggcc     1140
gccaccattg tctttcctag cggaatgggc acctcatccc ccgcccgcag gggctcagct    1200
gacggccctc ggagtgccca gccactgagg cctgaggatg acactgctc ttggcccctc     1260
tga                                                                   1263
```

<210> SEQ ID NO 70
<211> LENGTH: 2683
<212> TYPE: DNA
<213> ORGANISM: Artificial Sequence
<220> FEATURE:
<223> OTHER INFORMATION: Synthesized

<400> SEQUENCE: 70

```
gggcagagcg cacatcgccc acagtccccg agaagttggg gggaggggtc ggcaattgaa      60
ccggtgccta gagaaggtgg cgcggggtaa actgggaaag tgatgtcgtg tactggctcc     120
gccttttcc cgagggtggg ggagaaccgt atataagtgc agtagtcgcc gtgaacgttc      180
tttttcgcaa cgggtttgcc gccagaacac aggatccgcc accatggcct accagtgac     240
cgccttgctc ctgccgctgg ccttgctgct ccacgccgcc aggccggata tccagatgac     300
ccagagcccg agcagcctga gcgcgagcgt gggtgatcgc gtgaccatta cctgcagggc     360
aagtcaggac attagtaaat atttaaattg gtatcagcag aaaccgggta agcgccgaa      420
actgttaatt tatcatacat caagattaca ctcaggcgtg ccgtcgcgtt ttagcggctc     480
gggttcgggc accgatttta ccctgaccat ctcgagcttg cagccggagg acttcgccac    540
ctactattgc caacagggta atacgcttcc gtacacgttc ggtcagggca ccaaagtgga     600
gatcaaaggt ggcggtggct cgggcggtgg tgggtcgggt ggcggcggat ctgaggtgca     660
gctggtggag tctgggggag gcttggtaca gcctgggggg tccctgagac tctcctgtgc    720
```

```
agcctctgga gtgtccctgc ctgattatgg cgtgtcctgg gtccgccagg ctccagggaa      780
ggggctggag tgggtttcag tgatctgggg cagcgagaca acctactaca acagcgccct      840
gaagtcccga ttcaccatct ccagagacaa tgccaagaac tcactgtatc tgcaaatgaa      900
cagcctgaga gccgaggaca cggctgtgta ttactgtgcg aagcactact actacggcgg      960
cagctacgct atggactact ggggccaagg aaccctggtc accgtgtcct caaccacgac     1020
gccagcgccg cgaccaccaa caccggcgcc accatcgcg tcgcagcccc tgtccctgcg      1080
cccagaggcg tgccggccag cggcgggggg cgcagtgcac acgaggggc tggacttcgc      1140 ctgtgatatc tacatctggg cgcccttggc cgggacttgt ggggtccttc tcctgtcact     1200
ggttatcacc ctttactgca acgggcag aaagaaactc ctgtatatat tcaaacaacc       1260
atttatgaga ccagtacaaa ctactcaaga ggaagatggc tgtagctgcc gatttccaga     1320
agaagaagaa ggaggatgtg aactgagagt gaagttcagc aggagcgcag acgcccccgc     1380
gtaccagcag ggccagaacc agctctataa cgagctcaat ctaggacgaa gagaggagta     1440
cgatgttttg gacaagaggc gtggccggga ccctgagatg gggggaaagc cgagaaggaa     1500
gaaccctcag gaaggcctgt acaatgaact gcagaaagat aagatggcgg aggcctacag     1560
tgagattggg atgaaaggcg agcgccggag gggcaagggg cacgatggcc tttaccaggg     1620
tctcagtaca gccaccaagg acacctacga cgcccttcac atgcaggccc tgccccctcg     1680
ctaatcgagg tcgacggtat cgataagctt gatatcgaat taggaggaaa aactgtttca     1740
tacagaaggc gtcaattagg aggaaaaact gtttcataca gaaggcgtca attaggagga     1800
aaaactgttt catacagaag gcgtcaattg gtcccatcga attaggagga aaaactgttt     1860
catacagaag gcgtcaatta ggaggaaaaa ctgtttcata cagaaggcgt caattaggag     1920
gaaaaactgt ttcatacaga aggcgtcaat tggtcccggg acattttgac accccataa      1980 tatttttcca gaattaacag tataaattgc atctcttgtt caagagttcc ctatcactct     2040
ctttaatcac tactcacagt aacctcaact cctggccacc atgcagatcc acaggcgcc      2100 ctggccagtc gtctgggcgg tgctacaact gggctggcgg ccaggatggt tcttagactc     2160
cccagacagg ccctggaacc ccccaccctt ctccccagcc ctgctcgtgg tgaccgaagg     2220
ggacaacgcc accttcacct gcagcttctc caacacatcg gagagcttcg tgctaaactg     2280
gtaccgcatg agcccagca accagacgga caagctggcc gccttccccg aggaccgcag      2340
ccagcccggc caggactgcc gcttccgtgt cacacaactg cccaacgggc gtgacttcca     2400
catgagcgtg gtcagggccc ggcgcaatga cagcggcacc tacctctgtg ggccatctc      2460 cctggccccc aaggcgcaga tcaaagagag cctgcgggca gagctcaggg tgacagagag     2520
aagggcagaa gtgcccacag cccacccag ccccctcaccc aggccagccg gccagttcca     2580
aaccctggtg gttggtgtcg tgggcggcct gctgggcagc ctggtgctgc tagtctgggt     2640
cctggccgtc atctgctccc gggccgcacg agggacaata taa                      2683
```

<210> SEQ ID NO 71
<211> LENGTH: 2947
<212> TYPE: DNA
<213> ORGANISM: Artificial Sequence
<220> FEATURE:
<223> OTHER INFORMATION: Synthesized

<400> SEQUENCE: 71

```
gggcagagcg cacatcgccc acagtccccg agaagttggg gggaggggtc ggcaattgaa       60
```

```
ccggtgccta gagaaggtgg cgcggggtaa actgggaaag tgatgtcgtg tactggctcc    120
gccttttttcc cgagggtggg ggagaaccgt atataagtgc agtagtcgcc gtgaacgttc   180
tttttcgcaa cgggtttgcc gccagaacac aggatccgcc accatggcct accagtgac    240
cgccttgctc ctgccgctgg ccttgctgct ccacgccgcc aggccggata tccagatgac    300
ccagagcccg agcagcctga gcgcgagcgt gggtgatcgc gtgaccatta cctgcagggc    360
aagtcaggac attagtaaat atttaaattg gtatcagcag aaaccgggta aagcgccgaa    420
actgttaatt tatcatacat caagattaca ctcaggcgtg ccgtcgcgtt ttagcggctc    480
gggttcgggc accgatttta ccctgaccat ctcgagcttg cagccggagg acttcgccac    540
ctactattgc caacagggta atacgcttcc gtacacgttc ggtcagggca ccaaagtgga    600
gatcaaaggt ggcggtggct cgggcggtgg tgggtcgggt ggcggcggat ctgaggtgca    660
gctggtggag tctgggggag gcttggtaca gcctgggggg tccctgagac tctcctgtgc    720
agcctctgga gtgtccctgc ctgattatgg cgtgtcctgg gtccgccagg ctccagggaa    780
ggggctggag tgggtttcag tgatcctggg cagcgagaca acctactaca acagcgccct    840
gaagtcccga ttcaccatct ccagagacaa tgccaagaac tcactgtatc tgcaaatgaa    900
cagcctgaga gccgaggaca cggctgtgta ttactgtgcg aagcactact actacggcgg    960
cagctacgct atggactact ggggccaagg aaccctggtc accgtgtcct caaccacgac    1020
gccagcgccg cgaccaccaa caccggcgcc caccatcgcg tcgcagcccc tgtccctgcg    1080
cccagaggcg tgccggccag cggcgggggg cgcagtgcac acgaggggc tggacttcgc    1140
ctgtgatatc tacatctggg cgcccttggc cgggacttgt ggggtccttc tcctgtcact    1200
ggttatcacc ctttactgca acggggcag aaagaaactc ctgtatatat tcaaacaacc    1260
atttatgaga ccagtacaaa ctactcaaga ggaagatggc tgtagctgcc gatttccaga    1320
agaagaagaa ggaggatgtg aactgagagt gaagttcagc aggagcgcag acgcccccgc    1380
gtaccagcag ggccagaacc agctctataa cgagctcaat ctaggacgaa gagaggagta    1440
cgatgttttg gacaagaggc gtggccggga ccctgagatg ggggaaagc cgagaaggaa    1500
gaaccctcag gaaggcctgt acaatgaact gcagaaagat aagatggcgg aggcctacag    1560
tgagattggg atgaaaggcg agcgccggag gggcaagggg cacgatggcc tttaccaggg    1620
tctcagtaca gccaccaagg acacctacga cgcccttcac atgcaggccc tgccccctcg    1680
ctaatcgagg tcgacggtat cgataagctt gatatcgaat taggaggaa aactgtttca    1740
tacagaaggc gtcaattagg aggaaaaact gtttcataca gaaggcgtca attaggagga    1800
aaactgtttc atacagaag gcgtcaattg gtcccatcga attaggagga aaaactgttt    1860
catacagaag gcgtcaatta ggaggaaaaa ctgtttcata cagaaggcgt caattaggag    1920
gaaaaactgt tcatacaga aggcgtcaat tggtcccggg acattttgac accccataa     1980
tattttccca gaattaacag tataaattgc atctcttgtt caagagttcc ctatcactct    2040
ctttaatcac tactcacagt aacctcaact cctggccacc atgcagatcc acaggcgcc    2100
ctggccagtc gtctgggcgg tgctacaact gggctggcgg ccaggatggt tcttagactc    2160
cccagacagg ccctggaacc cccccacctt ctccccagcc ctgctcgtgg tgaccgaagg    2220
ggacaacgcc accttcacct gcagcttctc caacacatcg gagagcttcg tgctaaactg    2280
gtaccgcatg agcccagca accagacgga caagctggcc gcttccccg aggaccgcag    2340
ccagcccggc caggactgcc gcttccgtgt cacacaactg cccaacgggc gtgacttcca    2400
catgagcgtg gtcagggccc ggcgcaatga cagcggcacc tacctctgtg gggccatctc    2460
```

```
cctggccccc aaggcgcaga tcaaagagag cctgcgggca gagctcaggg tgacagagag    2520
aagggcagaa gtgcccacag cccacccag ccctcaccc aggccagccg gccagttcca     2580
aaccctggtg gttggtgtcg tgggcggcct gctgggcagc ctggtgctgc tagtctgggt   2640
cctggccgtc atctgctccc gggccgcacg agggacaata ggagccaggc gcaccggcca   2700 gccctgaag gaggacccct cagccgtgcc tgtgttctct gtggacgccg gggagctgga    2760
tttccagtgg cgagagaaga ccccggagcc ccccgtgccc tgtgtccctg agcagacgga   2820
ggccgccacc attgtctttc ctagcggaat gggcacctca tcccccgccc gcaggggctc   2880
agctgacggc cctcggagtg cccagccact gaggcctgag gatggacact gctcttggcc   2940
cctctga                                                              2947
```